(12) United States Patent
Faustman

(10) Patent No.: US 11,266,730 B2
(45) Date of Patent: Mar. 8, 2022

(54) METHODS OF TREATING AND DIAGNOSING DISEASE USING BIOMARKERS FOR BCG THERAPY

(71) Applicant: The General Hospital Corporation, Boston, MA (US)

(72) Inventor: Denise L. Faustman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 498 days.

(21) Appl. No.: 15/763,967

(22) PCT Filed: Sep. 29, 2016

(86) PCT No.: PCT/US2016/054535
§ 371 (c)(1),
(2) Date: Mar. 28, 2018

(87) PCT Pub. No.: WO2017/059132
PCT Pub. Date: Apr. 6, 2017

(65) Prior Publication Data
US 2018/0296658 A1 Oct. 18, 2018

Related U.S. Application Data

(60) Provisional application No. 62/234,428, filed on Sep. 29, 2015.

(51) Int. Cl.
*A01N 63/00* (2020.01)
*A61K 39/04* (2006.01)
*C12Q 1/6883* (2018.01)
*G01N 33/48* (2006.01)
*G01N 33/66* (2006.01)
*G01N 33/92* (2006.01)
*A61P 3/06* (2006.01)
*A61K 31/397* (2006.01)
*A61K 45/06* (2006.01)

(52) U.S. Cl.
CPC ............ *A61K 39/04* (2013.01); *A61K 31/397* (2013.01); *A61K 45/06* (2013.01); *A61P 3/06* (2018.01); *C12Q 1/6883* (2013.01); *G01N 33/48* (2013.01); *G01N 33/66* (2013.01); *G01N 33/92* (2013.01); *C12Q 2600/106* (2013.01); *C12Q 2600/118* (2013.01); *C12Q 2600/154* (2013.01); *C12Q 2600/158* (2013.01); *G01N 2800/52* (2013.01)

(58) Field of Classification Search
CPC ................................................... A61K 39/04
See application file for complete search history.

(56) References Cited

U.S. PATENT DOCUMENTS

| | | | |
|---|---|---|---|
| 4,309,418 A | 1/1982 | Green | |
| 4,457,916 A | 7/1984 | Hayashi et al. | |
| 4,495,282 A | 1/1985 | Ohnishi et al. | |
| 4,677,063 A | 6/1987 | Mark et al. | |
| 4,677,064 A | 6/1987 | Mark et al. | |
| 4,681,760 A | 7/1987 | Fathman | |
| 4,791,101 A | 12/1988 | Adolf | |
| 4,816,567 A | 3/1989 | Cabilly et al. | |
| 4,879,226 A | 11/1989 | Wallace et al. | |
| 4,963,354 A | 10/1990 | Shepard et al. | |
| 4,985,241 A | 1/1991 | Zimmerman et al. | |
| 5,002,876 A | 3/1991 | Sreekrishna et al. | |
| 5,059,530 A | 10/1991 | Oshima et al. | |
| 5,139,481 A | 8/1992 | Faustman et al. | |
| 5,166,142 A | 11/1992 | Moss et al. | |
| 5,215,743 A | 6/1993 | Singh et al. | |
| 5,283,058 A | 2/1994 | Faustman | |
| 5,288,852 A | 2/1994 | Yamada et al. | |
| 5,370,870 A | 12/1994 | Wong | |
| 5,487,984 A | 1/1996 | Allet et al. | |
| 5,538,854 A | 7/1996 | Faustman | |
| 5,560,908 A | 10/1996 | Satoh et al. | |
| 5,593,698 A | 1/1997 | Weiner et al. | |
| 5,783,216 A | 7/1998 | Faustman | |
| 5,821,337 A | 10/1998 | Carter et al. | |
| 5,843,425 A | 12/1998 | Sachs et al. | |
| 5,843,452 A | 12/1998 | Wiedmann et al. | |
| 5,874,306 A | 2/1999 | Beattie et al. | |
| 5,919,452 A | 7/1999 | Le et al. | |
| 6,046,031 A | 4/2000 | Ni et al. | |

(Continued)

FOREIGN PATENT DOCUMENTS

| | | |
|---|---|---|
| EP | 0612529 A2 | 8/1994 |
| EP | 2295588 A1 | 3/2011 |

(Continued)

OTHER PUBLICATIONS

Gylling et al (Diabetes vol. 53, pp. 2217-2222) (Year: 2004).*
Canas et al (Pediatric Diabetes vol. 16, No. 2, pp. 79-89) (Year: 2015).*
Navarro (Boletin Med Univ Autonoma Guadalajara vol. 3, No. 2, pp. 24-31) (Year: 1963).*
Waters et al (International Journal of Leprosy and Other Mycobacterial Diseases, vol. 61, No. 4 Suppl., pp. 103A-104A) (Year: 1993 ).*
Nwosu et al (Journal of Medical Investigation and Practice, vol. 2, pp. 5-10) (Year: 2001).*

(Continued)

*Primary Examiner* — Albert M Navarro
(74) *Attorney, Agent, or Firm* — Clark & Elbing LLP

(57) ABSTRACT

The invention provides methods of treating disease, such as hypercholesterolemia (e.g., by modulating serum lipids, such as cholesterol, low-density lipoproteins, high-density lipoproteins, and triglycerides) and hyperglycemia by administering Bacillus Calmette-Guerin (BCG). Methods of the invention also encompass the use of genomic, proteomic, and metabolomic analyses for determining the likelihood that a patient has disease or will respond to treatment (e.g., with BCG therapy), as well as for determining whether a patient previously administered BCG would benefit from BCG redosing.

20 Claims, 18 Drawing Sheets

(56) References Cited

U.S. PATENT DOCUMENTS

| | | | |
|---|---|---|---|
| 6,056,952 A | 5/2000 | Rosenberg | |
| 6,110,206 A | 8/2000 | Stone | |
| 6,159,461 A | 12/2000 | Besmer et al. | |
| 6,165,737 A | 12/2000 | Wang et al. | |
| 6,177,076 B1 | 1/2001 | Lattime et al. | |
| 6,284,879 B1 | 9/2001 | Faustman | |
| 6,414,218 B1 | 7/2002 | Faustman et al. | |
| 6,420,139 B1 | 7/2002 | Classen | |
| 6,491,908 B1 | 12/2002 | Rosenberg | |
| 6,599,710 B1 | 7/2003 | Faustman | |
| 6,617,171 B2 | 9/2003 | Faustman et al. | |
| 6,660,487 B2 | 12/2003 | Faustman | |
| 6,773,705 B1 | 8/2004 | Faustman et al. | |
| 6,844,011 B1 | 1/2005 | Faustman | |
| 6,866,843 B2 | 3/2005 | Habener et al. | |
| 6,923,959 B2 | 8/2005 | Habener et al. | |
| 6,984,380 B1 | 1/2006 | Faustman | |
| 7,015,037 B1 | 3/2006 | Furcht et al. | |
| 7,438,902 B2 | 10/2008 | Habener et al. | |
| 7,485,293 B1 | 2/2009 | Faustman | |
| 7,510,877 B2 | 3/2009 | Yilmaz et al. | |
| 7,537,756 B2 | 5/2009 | Habener et al. | |
| 7,582,313 B2 | 9/2009 | Faustman | |
| 7,628,988 B2 | 12/2009 | Faustman | |
| RE41,887 E * | 10/2010 | Faustman | A61K 38/191 435/7.2 |
| 7,867,765 B2 | 1/2011 | Faustman et al. | |
| 8,017,392 B2 | 9/2011 | Faustman | |
| 8,021,693 B2 | 9/2011 | Faustman | |
| 8,173,129 B2 | 5/2012 | Faustman | |
| 8,187,886 B2 | 5/2012 | Faustman et al. | |
| RE43,467 E | 6/2012 | Faustman | |
| 8,697,077 B2 | 4/2014 | Faustman | |
| 8,753,888 B2 | 6/2014 | Faustman et al. | |
| 8,969,015 B2 | 3/2015 | Faustman | |
| 9,410,144 B2 | 8/2016 | Faustman et al. | |
| 2002/0106689 A1 | 8/2002 | Faustman et al. | |
| 2002/0123472 A1 | 9/2002 | Faustman | |
| 2002/0187548 A1 | 12/2002 | Keller et al. | |
| 2003/0005469 A1 | 1/2003 | Faustman et al. | |
| 2003/0031657 A1 | 2/2003 | Habener et al. | |
| 2004/0028658 A1 | 2/2004 | Faustman | |
| 2004/0031066 A9 | 2/2004 | Faustman et al. | |
| 2004/0229785 A1 | 11/2004 | Faustman | |
| 2004/0235160 A1 | 11/2004 | Nishikawa et al. | |
| 2005/0080239 A1 | 4/2005 | Ditzel et al. | |
| 2005/0158288 A1 | 7/2005 | Faustman | |
| 2005/0158302 A1 | 7/2005 | Faustman et al. | |
| 2005/0181502 A1 | 8/2005 | Furcht et al. | |
| 2005/0244386 A1 | 11/2005 | Habener et al. | |
| 2006/0062769 A1 | 3/2006 | Habener et al. | |
| 2006/0069161 A1 | 3/2006 | Lee et al. | |
| 2007/0116688 A1 | 5/2007 | Faustman | |
| 2007/0238649 A1 | 10/2007 | Kadowaki et al. | |
| 2008/0102054 A1 | 5/2008 | Faustman | |
| 2008/0175830 A1 | 7/2008 | Steinman et al. | |
| 2008/0233149 A1* | 9/2008 | Mittelman | A61K 38/1816 424/209.1 |
| 2009/0054358 A1 | 2/2009 | Small et al. | |
| 2009/0257982 A1 | 10/2009 | Scheiber et al. | |
| 2010/0068177 A1 | 3/2010 | Faustman | |
| 2010/0151062 A1 | 6/2010 | Stefanon | |
| 2010/0298232 A1 | 11/2010 | Liu | |
| 2011/0111476 A1 | 5/2011 | Faustman et al. | |
| 2011/0177051 A1 | 7/2011 | Galski-Lorberboum et al. | |
| 2011/0177592 A1 | 7/2011 | Faustman et al. | |
| 2012/0045435 A1 | 2/2012 | Deisher | |
| 2012/0196919 A1 | 8/2012 | Brown et al. | |
| 2012/0201856 A1* | 8/2012 | Marchal | A61K 39/04 424/282.1 |
| 2012/0295246 A1 | 11/2012 | Faustman et al. | |
| 2013/0115207 A1 | 5/2013 | Faustman | |
| 2013/0230850 A1 | 9/2013 | Akirav | |
| 2014/0134644 A1 | 5/2014 | Faustman | |
| 2014/0186400 A1 | 7/2014 | Faustman | |
| 2014/0369973 A1 | 12/2014 | Bernstein et al. | |
| 2015/0111276 A1 | 4/2015 | Faustman et al. | |
| 2015/0322424 A1 | 11/2015 | Faustman et al. | |
| 2015/0366909 A1 | 12/2015 | Faustman | |
| 2016/0245808 A1 | 8/2016 | Faustman | |

FOREIGN PATENT DOCUMENTS

| | | |
|---|---|---|
| JP | 2013-534925 A | 9/2013 |
| WO | WO-92/04033 A1 | 3/1992 |
| WO | WO-93/02690 A1 | 2/1993 |
| WO | WO-94/09137 A1 | 4/1994 |
| WO | WO-95/24914 A1 | 9/1995 |
| WO | WO-95/25533 A1 | 9/1995 |
| WO | WO-97/08328 A1 | 3/1997 |
| WO | WO-97/21802 A1 | 6/1997 |
| WO | WO-99/53953 A2 | 10/1999 |
| WO | WO-99/59632 A1 | 11/1999 |
| WO | WO-00/53209 A1 | 9/2000 |
| WO | WO-02/26819 A2 | 4/2002 |
| WO | WO-2004/003164 A2 | 1/2004 |
| WO | WO-2005/042727 A2 | 5/2005 |
| WO | WO-2006/109044 A2 | 10/2006 |
| WO | WO-2011/163566 A2 | 12/2011 |
| WO | WO-2012/122464 A1 | 9/2012 |
| WO | WO-2012/174522 A1 | 12/2012 |
| WO | WO-2014/124134 A1 | 8/2014 |
| WO | WO-2014/186311 A1 | 11/2014 |
| WO | WO-2015/057968 A2 | 4/2015 |

OTHER PUBLICATIONS

Sula (J. Rev Czech vol. 2, No. 2, pp. 127-135) (Year: 1956).*

Dong et al., "Essential protective role of tumor necrosis factor receptor 2 in neurodegeneration," Proc Natl Acad Sci USA. 113(43):12304-9 (2016).

Yang et al., "A variant of TNFR2-Fc fusion protein exhibits improved efficacy in treating experimental rheumatoid arthritis," PLoS Comput Biol. 6(2):e1000669 (2010) (7 pages).

Khalili et al., "Treatment for salivary gland hypofunction at both initial and advanced stages of Sjögren-like disease: a comparative study of bone marrow therapy versus spleen cell therapy with a 1-year monitoring period," Cytotherapy. 16(3):412-23 (2014).

Almoallim et al., "Anti-tumor necrosis factor-alpha induced systemic lupus erythematosus," Open Rheumatol J. 6:315-9 (2012).

Khalili et al., "Mesenchymal stromal cells improve salivary function and reduce lymphocytic infiltrates in mice with Sjögren's-like disease," PLoS One. 7(6):e38615 (2012) (11 pages).

Chen et al., "Contrasting effects of TNF and anti-TNF on the activation of effector T cells and regulatory T cells in autoimmunity," available in PMC Dec. 1, 2012, published in final edited form as: FEBS Lett. 585(23):3611-8 (2011) (16 pages).

Khalili et al., "Bone marrow cells are a source of undifferentiated cells to prevent Sjögren's syndrome and to preserve salivary glands function in the non-obese diabetic mice," available in PMC Jun. 13, 2013, published in final edited form as: Int J Biochem Cell Biol. 42(11):1893-9 (2010) (18 pages).

Madsen et al., "Oligodendroglial TNFR2 mediates membrane TNF-dependent repair in experimental autoimmune encephalomyelitis by promoting oligodendrocyte differentiation and remyelination," J Neurosci. 36(18):5128-43 (2016).

Blüml et al., "Antiinflammatory effects of tumor necrosis factor on hematopoietic cells in a murine model of erosive arthritis," Arthritis Rheum. 62(6):1608-19 (2010).

Zachs et al., "Noninvasive ultrasound stimulation of the spleen to treat inflammatory arthritis," Nat Commun. 10:951 (2019) (10 pages).

Rabinovitch et al., "TNF-alpha down-regulates type 1 cytokines and prolongs survival of syngeneic islet grafts in nonobese diabetic mice," J Immunol. 159(12):6298-6303 (1997).

Baeza et al., "Specific reg II gene overexpression in the non-obese diabetic mouse pancreas during active diabetogenesis," FEBS Letters. 416(3):364-8 (1997).

(56) References Cited

OTHER PUBLICATIONS

Palombella et al., "The ubiquitin-proteasome pathway is required for processing the NF-$_{kappa}$B1 precursor protein and the activation of NF-$_{kappa}$B," Cell. 78:773-785 (1994).
Beg et al., "An essential role for NF-kappaB in preventing TNF-alpha-induced cell death," Science. 274(5288):782-784 (1996).
Song et al., "Tumor necrosis factor-related apoptosis-inducing ligand (TRAIL) is an inhibitor of autoimmune inflammation and cell cycle progression," J Exp Med. 191(7):1095-1103 (2000).
Robertson et al., "Preservation of insulin mRNA levels and insulin secretion in HIT cells by avoidance of chronic exposure to high glucose concentrations," J Clin Invest. 90:320-325 (1992).
Tartaglia et al., "The two different receptors for tumor necrosis factor mediate distinct cellular responses," Proc Natl Acad Sci USA. 88:9292-9296 (1991).
Hester et al., "Studies on the cytophilic properties of human beta2-microglobulin. II. The role of histocompatibility antigens," Scand J Immunol. 9(2):125-134 (1979).
Faustman et al., "Murine pancreatic beta-Cells express H-2K and H-2D but not Ia antigens," J Exp Med. 151:1563-1568 (1980).
Klinkhoff, "Biological agents for rheumatoid arthritis: targeting both physical function and structural damage," Drugs. 64(12):1267-83 (2004) (Abstract only).
Bendelac et al., "Syngeneic transfer of autoimmune diabetes from diabetic NOD mice to healthy neonates. Requirement for both L3T4$^+$ and Lyt-2$^+$ T Cells," J Exp Med. 166(4):823-832 (1987).
Waxman et al., "Demonstration of two distinct high molecular weight proteases in rabbit reticulocytes, one of which degrades ubiquitin conjugates," J Biol Chem. 262(6):2451-2457 (1987).
Penfornis et al., "Polymorphisms of human TAP2 detected by denaturing gradient gel electrophoresis," Hum Immunol. 64(1):156-67 (2003).
Raab et al., "In vitro evaluation of methotrexate and azathioprine for antipsoriatic activity," Arch Derm Res. 253:77-84 (1975).
Barres, "A new role for glia: generation of neurons!," Cell. 97(6):667-70 (1999).
Weissman, "Translating stem and progenitor cell biology to the clinic: barriers and opportunities," Science. 287:1442-1446 (2000).
Colucci et al., "Programmed cell death in the pathogenesis of murine IDDM: resistance to apoptosis induced in lymphocytes by cyclophosphamide," J Autoimmunity. 9:271-276 (1996).
Sadelain et al., "Prevention of type I diabetes in NOD mice by adjuvant immunotherapy," Diabetes. 39:583-589 (1990).
Brazelton et al., "From marrow to brain: expression of neuronal phenotypes in adult mice," Science. 290:1775-1779 (2000).
Welborn et al., "A human tumor necrosis factor p75 receptor agonist stimulates in vitro T cell proliferation but does not produce inflammation or shock in the baboon," J Exp Med. 184(1):165-171 (1996).
Darzynkiewicz et al., "Use of flow and laser scanning cytometry to study mechanisms regulating cell cycle and controlling cell death," Clinics in Laboratory Medicine. 21(4):857-873 (2001).
Alison et al., "Hepatocytes from non-hepatic adult stem cells," Nature. 406(6793):257 (2000).
Okubo et al., "Treg activation defect in type 1 diabetes: correction with TNFR2 agonism," Clin Transl Immunology. 8:5(1):e56 (2016) (9 pages).
Wellik et al., "Hox11 paralogous genes are essential for metanephric kidney induction," Genes Dev. 16:1423-1432 (2002).
Declaration of Dr. Denise Faustman from U.S. Appl. No. 10/775,487, dated Jun. 14, 2007 (13 pages).
Gage, "Mammalian neural stem cells," Science. 287:1433-1438 (2000).
Cairns et al., "New onset systemic lupus erythematosus in a patient receiving etanercept for rheumatoid arthritis," Ann Rheum Dis. 61 (11):1031-2 (2002).
Wellik, "The role of Hox11 paralogous genes in prostate development," Grant Detail. (2009) (1 page)(Abstract only).
Yan et al., "Impaired processing and presentation by MHC class II proteins in human diabetic cells," J Immunol. 170(1):620-7 (2003).

Rietze et al., "Purification of a pluripotent neural stem cell from the adult mouse brain," Nature. 412(6848):736-739 (2001).
Sun et al., "MHC class I multimers," Arthritis Res. 3(5):265-269 (2001).
Weringer et al., "Identification of T cell subsets and Class I and Class II antigen expression in islet grafts and pancreatic islets of diabetic BioBreeding/Worcester rats," Am J Pathol. 132(2):292-303 (1988).
Eglitis et al., "Hematopoietic cells differentiate into both microglia and macroglia in the brains of adult mice," Proc Natl Acad Sci USA. 94:4080-4085 (1997).
Schmidt et al., "Interspecies exchange of beta2-microglobulin and associated MHC and differentiation antigens," Immunogenetics. 13(6):483-91 (1981).
Coux et al., "Enzymes catalyzing ubiquitination and proteolytic processing of the p105 precursor of nuclear factor kappaB1," J Biol Chem. 273(15):8820-8828 (1998).
Wicker et al., "Transfer of autoimmune diabetes mellitus with splenocytes from nonobese diabetic (NOD) mice," Diabetes. 35:855-860 (1986).
EPO Communication Enclosing Supplementary European Search Report for EP Application No. 03762242.0, dated Jun. 8, 2009 (8 pages).
EPO Invitation pursuant to Article 94(3) and Rule 71(1) EPC for European Application No. 00914899.0, dated Jun. 2, 2014 (4 pages).
Van Zee et al., "A human tumor necrosis factor (TNF) alpha mutant that binds exclusively to the p55 TNF receptor produces toxicity in the baboon," J Exp Med. 179(4):1185-1191 (1994).
Willis et al., "Type 1 Diabetes in insulin-treated adult-onset diabetic subjects," Diabetes Res Clin Pract. 42:49-53 (1998).
EPO Communication pursuant to Article 94(3) and Rule 71(1) EPC for European Application No. 00914899.0, dated Mar. 6, 2015 (3 pages).
Kuhtreiber et al., "Long-term reduction in hyperglycemia in advanced type 1 diabetes: the value of induced aerobic glycolysis with BCG vaccinations," NPJ Vaccines. 3:23 (2018) (14 pages).
Dieguez-Acuna et al., "Characterization of mouse spleen cells by subtractive proteomics," Mol Cell Proteomics. 4(10):1459-1470 (2005).
Winston, "Embryonic stem cell research: the case for . . . ," Nat Med. 7(4):396-397 (2001).
Faustman et al., "Cells for repair: breakout session summary," Ann N Y Acad Sci. 961:45-7 (2002).
Rosenthal, "Prometheus's vulture and the stem-cell promise," N Engl J Med. 349(3):267-74 (2003).
Extended European Search Report for European Patent Application No. 11008889.5, dated Apr. 12, 2012 (10 pages).
Wong et al., "Identification of an MHC class I-restricted autoantigen in Type I Diabetes by screening an organ-specific cDNA library," Nat Med. 5(9):1026-1031 (1999).
EPO Communication under Rule 71(3) EPC for European Application No. 00914899.0, dated Jun. 23, 2015 (6 pages).
Shehadeh et al., "Effect of adjuvant therapy on development of diabetes in mouse and man," Lancet. 343:706-707 (1994).
Enayati et al., "Association of anti-tumor necrosis factor therapy with the development of multiple sclerosis," J Clin Gastroenterol. 39(4): 303-6 (2005) (1 page) (Abstract only).
Written Opinion for International Application No. PCT/US2004/037998, dated Feb. 28, 2008 (3 pages).
Examiner's Report for Canadian Patent Application No. 2,543,745, dated Jul. 15, 2011 (4 pages).
Ryu et al., "Reversal of established autoimmune diabetes by restoration of endogenous beta cell function," J Clin Invest. 108(1):63-72 (2001).
Faustman et al., "Abnormal T-lymphocyte subsets in Type I Diabetes," Diabetes. 38:1462-1468 (1989).
Xu et al., "MHC/peptide tetramer-based studies of T cell function," J Immunol Methods. 268:21-28 (2002).
Extended European Search Report for European Application No. 14189654.8, dated Feb. 16, 2015 (7 pages).

(56) References Cited

OTHER PUBLICATIONS

Humphreys-Beher et al., "New concepts for the development of autoimmune exocrinopathy derived from studies with the NOD mouse model," Arch Oral Biol. 44(Suppl 1):S21-S25 (1999) (Abstract Only) (2 pages).
EPO Communication Pursuant to Article 94(3) EPC issued in European Patent Application No. 03762242.0, dated Dec. 1, 2011 (4 pages).
Yagi et al., "Possible mechanism of the preventive effect of BCG against diabetes mellitus in NOD Mouse. I. Generation of suppressor macrophages in spleen cells of BCG-vaccinated mice," Cell Immunol. 138:130-141 (1991).
Faustman, "Reversal of established autoimmune diabetes by in situ beta-cell regeneration," Ann N Y Acad Sci. 961:40 (2002).
Schaible, "Long term safety of infliximab," Can J Gastroenterol. 14(Suppl C):29C-32C (2000) (Abstract only).
Loetscher et al., "Human tumor necrosis factor alpha (TNF alpha) mutants with exclusive specificity for the 55-kDa or 75-kDa TNF receptors," J Biol Chem. 268(35):26350-26357 (1993).
Yagi et al., "Possible mechanism of the preventive effect of BCG against diabetes mellitus in NOD Mouse. II. Suppression of pathogenesis by macrophage transfer from BCG-vaccinated mice," Cell Immunol. 138:142-149 (1991).
Faustman et al., "T-lymphocyte changes linked to autoantibodies. Association of insulin autoantibodies with CP4+CP45R+ lymphocyte subpopulation in prediabetic subjects," Diabetes. 40:590-597 (1991).
Speiser et al., "Loss of ATP-dependent proteolysis with maturation of reticulocytes and erythrocytes," J Biol Chem. 257(23):14122-14127 (1982).
EPO Summons to attend oral proceedings pursuant to Rule 115(1) EPC for European Application No. 00914899.0, dated Nov. 12, 2014 (6 pages).
Yan et al., "Reduced expression of Tap1 and Lmp2 antigen-processing genes in the nonobese diabetic (NOD) mouse due to a mutation in their shared bidirectional promoter," J Immunol. 159:3068-3080 (1997).
Fischer et al., "A TNF receptor 2 selective agonist rescues human neurons from oxidative stress-induced cell death," PloS One. 6(11):e27621 (2011) (11 pages).
Gazda et al., "Regulation of autoimmune diabetes: characteristics of non-islet-antigen specific therapies," Immunol Cell Biol. 74: 401-407 (1996).
Raju et al., "Characterization and developmental expression of Tlx-1, the murine homolog of HOX11," Mech Dev. 44(1):51-64 (1993).
Yang et al., "Effect of tumor necrosis factor alpha on insulin-dependent diabetes mellitus in NOD Mice. I. The early development of autoimmunity and the diabetogenic process," J Exp Med. 180:995-1004 (1994).
Fu et al., "Antigen processing and autoimmunity: Evaluation of mRNA abundance and function of HLA-Linked genes," Ann NY Acad Sci. 842:138-155 (1998).
Kaijzel et al., "Functional analysis of a human tumor necrosis factor alpha (TNF-alpha) promoter polymorphism related to joint damage in rheumatoid arthritis," Mol Med. 4:724-733 (1998).
Fan et al., "Generation of p50 subunit of NF-kappaB by processing of p105 through an ATP-dependent pathway," Nature. 354:395-398 (1991).
Ying et al., "Changing potency by spontaneous fusion," Nature. 416:545-548 (2002).
Penfornis et al., "Analysis of TAP2 polymorphisms in Finnish individuals with type I diabetes," Hum Immunol. 63(1):61-70 (2002).
Serup, "Panning for pancreatic stem cells," Nat Genet. 25:134-135 (2000).
Jacob et al., "Tumour necrosis factor-alpha in murine autoimmune 'lupus' nephritis," Nature. 331:356-358 (1988).

Zulewski et al., "Multipotential nestin-positive stem cells isolated from adult pancreatic islets differentiate ex vivo into pancreatic endocrine, exocrine, and hepatic phenotypes," Diabetes. 50:521-533 (2001).
Gazda et al., "Diabetes results from a late change in the autoimmune response of NOD mice," J Autoimmun. 10:261-270 (1997).
Szodoray et al., "Programmed cell death in rheumatoid arthritis peripheral blood T-cell subpopulations determined by laser scanning cytometry," Lab Invest. 83(12):1839-1848 (2003).
Feldman et al., "Anti-TNFalpha therapy is useful in rheumatoid arthritis and Crohn's disease: Analysis of the mechanism of action predicts utility in other diseases," Transplant Proc. 30(8):4126-4127 (1998).
Zöller et al., "Apoptosis resistance in peripheral blood lymphocytes of alopecia areata patients," Retrieved from Science Direct, published in: J Autoimmun. 23(3):241-256 (2004) (30 pages).
Glas et al., "The CD8+ T Cell repertoire in beta2-microglobulin-deficient mice is biased towards reactivity against self-major histocompatibility class I," J Exp Med. 179(2):661-672 (1994).
Altomonte et al., "Serum levels of interleukin-1b, tumour necrosis factor-a and interleukin-2 in rheumatoid arthritis. Correlation with disease activity," Clin Rheumatol. 11(2):202-205 (1992).
Durand et al., "Mesenchymal lineage potentials of aorta-gonad-mesonephros stromal clones," Haematologica. 91(9):1172-1179 (2006).
Vogel, "Stem cell research. Studies cast doubt on plasticity of adult cells," Science. 295:1989&1991 (2002).
Gottlieb et al., "Cell acidification in apoptosis: Granulocyte colony-stimulating factor delays programmed cell death in neutrophils by up-regulating the vacuolar $H^+$-ATPase," Proc Natl Acad Sci USA. 92:5965-5968 (1995).
Dinarello, "Interleukin-1, Interleukin-1 receptorsand Interleukin-1 receptor antagonist," Intern Rev Immunol. 16:457-499 (1998).
Fukada et al., "Two signals are necessary for cell proliferation induced by a cytokine receptor gp130: Involvement of STAT3 in anti-apoptosis," Immunity. 5:449-460 (1996).
Watt et al., "Specific alternative HOX11 transcripts are expressed in paediatric neural tumours and T-cell acute lymphoblastic leukaemia," Gene. 323:89-99 (2003) (Abstract only).
Hayashi et al., "Development of spontaneous uterine tumors in low molecular mass polypeptide-2 knockout mice," Cancer Res. 62(1):24-7 (2002).
Slack, "Stem cells in epithelial tissues," Science. 287:1431-1433 (2000).
Qin et al., "Complete Freund's adjuvant-induced T cells prevent the development and adoptive transfer of diabetes in nonobese diabetic mice," J Immunol. 150(5):2072-80 (1993).
Wilson et al., "Bone-marrow haematopoietic-stem-cell niches," Nat Rev Immunol. 6(2):93-106 (2006).
Hao et al., "Effect of mycophenolate mofetil on islet allografting to chemically induced or spontaneously diabetic animals," Transplant Proc. 24(6): 2843-2844 (1992).
Totpal et al., "TNF and its receptor antibody agonist differ in mediation of cellular responses," J Immunol. 153:2248-2257 (1994).
Genestier et al., "Immunosuppressive properties of methotrexate: Apoptosis and clonal deletion of activated peripheral T Cells," J Clin Invest. 102(2):322-328 (1998).
Hershko et al., "The ubiquitin system for protein degradation," Annu Rev Biochem. 61: 761-807 (1992).
International Search Report for International Application No. PCT/US2004/037998, dated Feb. 28, 2008 (2 pages).
Shakoor et al., "Drug-induced systemic lupus erythematosus associated with etanercept therapy," Lancet. 359(9306):579-80 (2002) (Absract only).
Kuehnle et al., "The therapeutic potential of stem cells from adults," BMJ. 325(7360):372-6 (2002).
Horsfall et al., "Characterization and specificity of B-cell responses in lupus induced by *Mycobacterium bovis* in NOD/Lt mice," Immunology 95:8-17 (1998).
Greenbaum et al., "Guidelines for Intervention Trials in Subjects with Newly Diagnosed Type 1 Diabetes," Diabetes. 52 (2003) (7 pages).
Grewal et al., "Local expression of transgene encoded TNFalpha in islets prevents autoimmune diabetes in nonobese diabetic (NOD)

(56) References Cited

OTHER PUBLICATIONS mice by preventing the development of auto-reactive islet-specific T Cells," J Exp Med. 184:1963-1974 (1996).
Li et al., "Use of Donor beta2-Microglobulin-Deficient Transgenic Mouse Liver Cells for Isografts, Allografts, and Xenografts," *Transplantation*. 55(4):940-6 (1993).
Faustman et al., "Comment on papers by Chong et al., Nishio et al., and Suri et al. on diabetes reversal in NOD mice," Science. 314(5803):1243 (2006) (2 pages).
Swale et al., "Etanercept-induced systemic lupus erythematosus," Clin Exp Dermatol. 28:604-607 (2003).
Declaration of Dr. Denise Faustman under 37 C.F.R. § 1.132 regarding U.S. Appl. No. 10/358,664, dated May 13, 2009 (4 pages).
Kodama et al., "The therapeutic potential of tumor necrosis factor for autoimmune disease: A mechanistically based hypothesis," Cell Mol Life Sci. 62:1850-1862 (2005).
International Search Report for International Application No. PCT/US00/06239 dated Jul. 31, 2000 (2 pages).
McInerney et al., "Prevention of insulitis and diabetes onset by treatment with complete Freund's adjuvant in NOD mice," Diabetes. 40:715-725 (1991).
Hartwell et al., "Aberrant cytokine regulation in macrophages from young autoimmune-prone mice: Evidence that the intrinsic defect in MRL macrophage IL-1 expression is transcriptionally controlled," Mol Immunol. 32(10):743-751 (1995).
EPO Communication pursuant to Rule 69 EPC for European Application No. 12005556.1, dated Oct. 7, 2014 (2 pages).
Jacob et al., "Monoclonal anti-tumor necrosis factor antibody renders non-obese diabetic mice hypersensitive to irradiation and enhances insulitis development," Int Immunol. 4(5):611-614 (1992).
Swirski et al., "Identification of splenic reservoir monocytes and their deployment to inflammatory sites," available in PMC Jan. 7, 2010, published in final edited form as: Science. 325(5940):612-616 (2009) (12 pages).
Johansson et al., "Identification of a neural stem cell in the adult mammalian central nervous system," Cell. 96:25-34 (1999).
Benkler et al., "Parkinson's disease, autoimmunity, and olfaction," Int J Neurosci. 119(12):2133-43 (2009) (Abstract only) (1 page).
Jakubowski et al., "Phase I trial of intramuscularly administered tumor necrosis factor in patients with advanced cancer," J Clin Oncol. 7(3):298-303 (1989).
Bernabeu et al., "Beta-microglobulin from serum associates with MHC class I antigens on the surface of cultured cells," Nature. 308:642-645 (1984) (Abstract only) (2 pages).
Hostikka et al., "The mouse Hoxc11 gene: genomic structure and expression pattern," Mech Dev. 70(1-2):133-145 (1998) (Abstract Only).
Cebrián et al., "MHC-I expression renders catecholaminergic neurons susceptible to T-cell-mediated degeneration," Nat Commun. 5:3633 (2014) (Abstract only) (1 page).
Christen et al., "A dual role for TNF-alpha in type 1 diabetes: islet-specific expression abrogates the ongoing autoimmune process when induced late but not early during pathogenesis," J Immunol. 166(12):7023-32 (2001).
Thomas et al., "Demyelination during anti-tumor necrosis factor alpha therapy with infliximab for Crohn's disease," Inflamm Bowel Dis. 10(1):28-31 (2004) (Abstract only).
Gueckel et al., "Mutations in the yeast proteasome beta-Type subunit Pre3 uncover position-dependent effects on proteasomal peptidase activity and in vivo function," J Biol Chem. 273(31): 19443-19452 (1998).
D'Andrea, "Add Alzheimer's disease to the list of autoimmune diseases," Med Hypotheses. 64(3):458-63 (2005) (Abstract only) (2 pages).
Kawasaki et al., "Prevention of type 1 diabetes: from the view point of beta cell damage," Diabetes Res Clin Pract. 66:S27-S32 (2004).
Abraham et al., "Human pancreatic islet-derived progenitor cell engraftment in immunocompetent mice," Am J Pathol. 164(3):817-30 (2004).

International Search Report for International Patent Application No. PCT/US03/20578, dated Apr. 27, 2004 (1 page).
International Preliminary Report on Patentability for International Application No. PCT/US2014/015101, dated Aug. 11, 2015 (9 pages).
Kodama et al., "Islet regeneration during the reversal of autoimmune diabetes in NOD mice," Science. 302:1223-1227 (2003).
Lakey et al., "BCG immunotherapy prevents recurrence of diabetes in islet grafts transplanted into spontaneously diabetic NOD mice," Transplantation. 57(8):1213-1217 (1994).
Mezey et al., "Turning blood into brain: Cells bearing neuronal antigens generated in vivo from bone marrow," Science. 290: 1779-1782 (2000).
Technical Data Sheet for Purified Rat Anti-Human CD120b, BD Pharmingen™ (2011) (2 pages).
Kopp et al., "Inhibition of NF-kappaB by sodium salicylate and aspirin," Science. 265:956-959 (1994).
Couzin, "Diabetes studies conflict on power of spleen cells," Science. 311:1694 (2006).
Jiang et al., "Pluripotency of mesenchymal stem cells derived from adult marrow," Nature. 418:41-49 (2002).
Extended European Search Report for European Application No. 14748807.6, dated Jul. 15, 2016 (10 pages).
Communication pursuant to Article 94(3) EPC for European Patent Application No. 14189654.8, dated Oct. 19, 2016 (5 pages).
Marriott, "TNF-alpha antagonists: Monoclonal antibodies, soluble receptors, thalidomide and other novel approaches," Expert Opin Invest Drugs. 6(8):1105-1108 (1997).
Mercurio et al., "p105 and p98 precursor proteins play an active role in NF-Kappa B-mediated signal transduction," Genes Dev. 7:705-718 (1993).
Communication pursuant to Rules 70(2) and 70a(2) EPC for European Application No. 14748807.6, dated Aug. 2, 2016 (1 page).
Lahav-Baratz et al., "Reversible phosphorylation controls the activity of cyclosome-associated cyclin-ubiquitin ligase," Proc Natl Acad Sci USA. 92:9303-9307 (1995).
Engleman et al., "Treatment of NZB/NZW F1 hybrid mice with Mycobacterium bovis strain BCG or type II interferon preparations accelerates autoimmune disease," Arthritis Rheum. 24(11):1396-1402 (1981).
Klingensmith et al., "Vaccination with BCG at diagnosis does not alter the course of IDDM," Diabetes 57th Annual Meeting and Scientific Sessions, Jun. 21-24, Boston MA. 40(Suppl 1):193A, 0744 (1997) (3 pages) (Abstract Only).
Chopra et al., "Exogenous TNFR2 activation protects from acute GvHD via host T reg cell expansion," J Exp Med. 213(9):1881-1900 (2016) (21 pages).
Lawrence et al., "Differential hepatocyte toxicity of recombinant Apo2L/TRAIL versions," Nat Med. 7(4):383-385 (2001).
Anderson et al., "Can stem cells cross lineage boundaries?," Nat Med. 7(4):393-5 (2001).
Cavallo et al., "BCG vaccine with and without nicotinamide in recent onset IDDM: a multicenter randomized trial," Second Congress of the Immunology of Diabetes Society, Canberra, Australia, Dec. 8-11, 1996. Autoimmunity. 24(Suppl. 1):18 (1996).
Mera et al., "The spleen contributes stem cells to peripheral blood stem cell transplants," J Stem Cell Res Ther. 4(11):1000253 (2014) (4 pages).
Li et al., "Abnormal class I assembly and peptide presentation in the nonobese diabetic mouse," Proc Natl Acad Sci USA. 91:11128-11132 (1994).
EPO Summons to attend oral proceedings pursuant to Rule 115(1) EPC for European Application No. 12005556.1, dated Dec. 18, 2015 (4 pages).
Koyama et al., "Hox11 genes establish synovial joint organization and phylogenetic characteristics in developing mouse zeugopod skeletal elements," Development. 137(22): 3795-800 (2010) (Abstract Only).
International Search Report and Written Opinion for International Application No. PCT/US2015/030282, dated Aug. 17, 2015 (18 pages).

(56) References Cited

OTHER PUBLICATIONS

Ban et al., "Selective death of autoreactive T Cells in human diabetes by TNF or TNF receptor 2 agonism," Proc Natl Acad Sci USA. 105(36):13644-13649 (2008).
Mittelman et al., "A phase I pharmacokinetic study of recombinant human tumor necrosis factor administered by a 5-day continuous infusion," Invest New Drugs. 10(3):183-190 (1992).
Ulaeto et al., "A T-cell dormant state in the autoimmune process of nonobese diabetic mice treated with complete Freund's adjuvant," Proc Natl Acad Sci USA. 89:3927-3931 (1992).
International Preliminary Report on Patentability for International Application No. PCT/US14/60908, dated Apr. 28, 2016 (8 pages).
Vermeire et al., "Autoimmunity associated with anti-tumor necrosis factor alpha treatment in Crohn's disease: a prospective cohort study," Gastroenterology. 125(1):32-9 (2003) (1 page) (Abstract only).
Feldmann et al., "Role of cytokines in rheumatoid arthritis," Annu Rev Immunol. 14:397-440 (1996) (1 page) (Abstract only).
Lammert et al., "Induction of pancreatic differentiation by signals from blood vessels," Science. 294:564-567 (2001).
Markmann et al., "Indefinite survival of MHC class I-deficient murine pancreatic islet allografts," Transplantation. 54(6):1085-1089 (1992).
Offield et al., "PDX-1 is required for pancreatic outgrowth and differentiation of the rostral duodenum," Development. 122:983-995 (1996).
Brayer et al., "Alleles from chromosomes 1 and 3 of NOD mice combine to influence Sjögren's syndrome-like autoimmune exocrinopathy," J. Rheumatol. 27(8):1896-1904 (2000).
Anderson et al., "The NOD mouse: a model of immune dysregulation," Annu Rev Immunol. 23:447-485 (2005).
Charles et al., "Assessment of antibodies to double-stranded DNA induced in rheumatoid arthritis patients following treatment with infliximab, a monoclonal antibody to tumor necrosis factor alpha: findings in open-label and randomized placebo-controlled trials," Arthritis Rheum. 43(11):2383-90 (2000).
Gerich et al., "Advances in diabetes for the millennium: Understanding insulin resistance," MedGenMed. 6(3 Suppl.):11 (2004) (9 pages).
Kodama et al., "Routes to regenerating islet cells: stem cells and other biological therapies for type 1 diabetes," Pediatr Diabetes. 5(Suppl 2):38-44 (2004).
Baeza et al., "Reg protein: a potential beta-cell-specific growth factor?," Diabetes Metab. 22(4):229-34 (1996).
Pontesilli et al., "Circulating lymphocyte populations and autoantibodies in non-obese diabetic (NOD) mice: a longitudinal study," Clin Exp Immunol. 70(1):84-93 (1987).
Prieto et al., "Apoptotic rate: A new indicator for the quantification of the incidence of apoptosis in cell cultures," Cytometry. 48(4):185-93 (2002).
Goldberg, "The mechanism and functions of ATP-dependent proteases in bacterial and animal cells," Eur J Biochem. 203:9-23 (1992).
Van Noort et al., "Cell biology of autoimmune diseases," Int Rev Cytol. 178:127-206 (1998).
Molinaro, "Diabetes," Professional Practice in Clinical Chemistry, Session 4: Chronic Diseases: Diagnosis & Management for Improved Patient Outcomes, Apr. 28-May 2, La Jolla, California (2013) (60 pages).
Hayashi et al., "Essential role of human leukocyte antigen-encoded proteasome subunits in NF-kappaB activation and prevention of tumor necrosis factor-alpha-induced apoptosis," J Biol Chem. 275(7):5238-5247 (2000).
Harada et al., "Prevention of overt diabetes and insulitis in NOD mice by a single BCG vaccination," Diabetes Res Clin Pract. 8:85-89 (1990).
Brod et al., "Ingested interferon alpha suppresses Type I diabetes in non-obese diabetic mice," Diabetologia. 41:1227-1232 (1998).
Atkinson et al., "The NOD mouse model of type 1 diabetes: As good as it gets?," Nat Med. 5(6):601-4 (1999).

Rath et al., "TNF-induced signaling in apoptosis," J Clin Immunol. 19(6):350-364 (1999).
McKay, "Mammalian deconstruction for stem cell reconstruction," Nat Med. 6(7):747-748 (2000).
International Search Report for International Patent Application No. PCT/US03/36531, dated Jul. 14, 2004 (1 page).
EPO Communication Pursuant to Article 94(3) EPC for European Patent Application No. 11008889.5, dated Mar. 19, 2014 (4 pages).
Zhang et al., "An animal study on the preventive intervention for decreasing the incidence of type 1 diabetes mellitus," Chinese Journal of Clinical Rehabilitation. 9(47):58-60 (2005) (English Abstract).
Hayashi et al., "Role of defective apoptosis in type 1 diabetes and other autoimmune diseases," Recent Prog Horm Res. 58:131-53 (2003).
Brod et al., "New clinical trial in newly diagnosed type 1 diabetes," <http://www.diabetesstation.org/articles/brod.htm>, retrieved Jun. 19, 2001 (2 pages).
Roberts et al., "Developmental expression of Hox11 and specification of splenic cell fate," Am J Pathol. 146(5):1089-1101 (1995).
Burnham et al., "Oral BCG vaccine in Crohn's disease," Gut. 20:229-233 (1979).
Gronostajski et al., "The ATP dependence of the degradation of short- and long-lived proteins in growing fibroblasts," J Biol Chem. 260(6):3344-3349 (1985).
Morrison, "Stem cell potential: Can anything make anything?" Curr Biol. 11:R7-R9 (2001).
Chatenoud et al., "CD3 antibody-induced dominant self tolerance in overtly diabetic NOD mice," J Immunol. 158(6):2947-2954 (1997).
Gaur et al., "Induction of islet allotolerance in nonhuman primates," Ann NY Acad Sci. 958:199-203 (2002).
Bjornson et al., "Turning brain into blood: A hematopoietic fate adopted by adult neural stem cells in vivo," Science. 283(5401):534-537 (1999).
Ono et al., "IDDM in BB rats. Enhanced MHC class I heavy-chain gene expression in pancreatic islets," Diabetes. 37:1411-1418 (1988).
Creasey et al., "Biological effects of recombinant human tumor necrosis factor and its novel muteins on tumor and normal cell lines," Cancer Res. 47(1):145-9 (1987).
Faustman et al., "Linkage of faulty major histocompatibility complex class I to autoimmune diabetes," Science. 254:1756-1761 (1991).
Von Herrath et al., "In vivo treatment with a MHC class I-restricted blocking peptide can prevent virus-induced autoimmune diabetes," J Immunol. 161:5087-5096 (1998).
Paolillo et al., "The effect of Bacille Calmette-Guérin on the evolution of new enhancing lesions to hypointense T1 lesions in relapsing remitting MS," J Neurol. 250:247-248 (2003).
Zhi et al., "Tumor Necrosis Factor-alpha Free Fatty Acid Leptin and Insulin Resistance," Hebei Medical Journal. 27(9):689-90 (2005).
Haas et al., "Pathways of ubiquitin conjugation," FASEB J. 11:1257-1268 (1997).
Choi et al., "Prevention of encephalomyocarditis virus-induced diabetes by live recombinant *Mycobacterium bovis* bacillus Calmette-Guérin in susceptible mice," Diabetes. 49:1459-1467 (2000).
Pozzilli, "BCG vaccine in insulin-dependent diabetes mellitus," Lancet. 349(9064):1520-1 (1997).
EPO Communication Pursuant to Article 94(3) EPC issued in European Patent Application No. 04817543.4, dated Jan. 22, 2010 (5 pages).
Satoh et al., "Inhibition of type I diabetes in BB rats with recombinant human tumor necrosis factor-alpha," J Immunol. 145(5):1395-1399 (1990).
Qin et al., "BCG vaccination prevents insulin-dependent diabetes mellitus (IDDM) in NOD mice after disease acceleration with cyclophosphamide," J Autoimmun.10:271-278 (1997).
Quintana et al., "Experimental autoimmune myasthenia gravis in naïve non-obese diabetic (NOD/LtJ) mice: Susceptibility associated with natural IgG antibodies to the acetylcholine receptor," Int Immunol. 15(1):11-16 (2003).
EPO Communication Pursuant to Article 94(3) EPC issued in European Patent Application No. 11008889.5, dated Mar. 4, 2013 (4 pages).

(56) References Cited

OTHER PUBLICATIONS

International Search Report and Written Opinion for International Patent Application No. PCT/US14/15101, dated Jun. 24, 2014 (14 pages).
Driscoll et al., "The proteasome (multicatalytic protease) is a component of the 1500-kDa proteolytic complex which degrades ubiquitin-conjugated proteins," J Biol Chem. 265(9):4789-4792 (1990).
Rajagopalan et al., "Pathogenic anti-DNA autoantibody-inducing T helper cell lines from patients with active lupus nephritis: Isolation of CD4$^-$8$^-$ T helper cell lines that express the gamma delta T-cell antigen receptor," Proc Natl Acad Sci USA. 87:7020-7024 (1990).
Examination Report issued in Australian Patent Application No. 2003247840, dated Jan. 31, 2008 (4 pages).
International Search Report and Written Opinion for International Application No. PCT/US14/60908, dated Apr. 6, 2015 (18 pages).
Ashton-Rickardt et al., "Evidence for a differential avidity model of T cell selection in the thymus," Cell. 76(4):651-63 (1994).
Rechsteiner, "Ubiquitin-mediated pathways for intracellular proteolysis," Annu Rev Cell Biol. 3:1-30 (1987).
Mak et al., "Signaling for survival and apoptosis in the immune system," Arthritis Res. 4(Suppl 3):S243-S252 (2002).
Kaufman et al., "Patterns of hemopoietic reconstitution in nonobese diabetic mice: dichotomy of allogeneic resistance versus competitive advantage of disease-resistant marrow," J Immunol. 158(5):2435-2442 (1997).
EPO Communication Pursuant to Article 94(3) EPC for European Patent Application No. 11008889.5, dated Oct. 27, 2014 (5 pages).
Roberts et al., "Hox11 controls the genesis of the spleen," Nature. 368:747-749 (1994).
Ferrando et al., "Adult T-Cell ALL patients whose lymphoblasts express the HOX11 oncogene have an excellent prognosis when treated with chemotherapy and are not candidates for allogeneic bone marrow transplantation in first remission," Blood. 11:Abstract 578 (2002) (1 page).
Silva et al., "Prevention of autoimmune diabetes through immunostimulation with Q fever complement-fixing antigen," Ann NY Acad Sci. 1005:423-430 (2003).
Robinson et al., "A novel NOD-derived murine model of primary Sjögren's Syndrome," Arth Rheum. 41(1):150-156 (1998).
Rolfe et al., "The ubiquitin-mediated proteolytic pathway as a therapeutic area," J Mol Med. 75:5-17 (1997).
Galaria et al., "Leukocytoclastic vasculitis due to etanercept," J Rheumatol. 27(8):2041-4 (2000) (1 page) (Abstract only).
Laakko et al., "Versatility of merocyanine 540 for the flow cytometric detection of apoptosis in human and murine cells," J Immunol Methods. 261:129-139 (2002).
Faustman et al., "Prevention of xenograft rejection by masking donor HLA class I antigens," Science. 252:1700-1702 (1991).
Sandborn et al., "Antitumor necrosis factor therapy for inflammatory bowel disease: a review of agents, pharmacology, clinical results, and safety," Inflamm Bowel Dis. 5(2):119-33 (1999) (Abstract only).
Ghosh et al., "Activation in vitro of NF-kappaB by phosphorylation of its inhibitor IkappaB," Nature. 344:678-682 (1990).
Juang et al., "Beneficial influence of glycemic control upon the growth and function of transplanted islets," Diabetes 43:1334-1339 (1994).
Munshi et al., "Use of serum c-peptide level to simplify diabetes treatment regimens in older adults," Am J Med. 122(4):395-7 (2009).
Satoh et al., "Recombinant human tumor necrosis factor alpha suppresses autoimmune diabetes in nonobese diabetic mice," J Clin Invest. 84:1345-1348 (1989).
Serreze et al., "Th1 to Th2 cytokine shifts in nonobese diabetic mice: Sometimes an outcome, rather than the cause, of diabetes resistance elicited by immunostimulation," J Immunol. 166:1352-1359 (2001).
Allen et al., "Effect of bacillus Calmette-Guerin vaccination on new-onset type 1 diabetes," Diabetes Care. 22(10):1703-7 (1999).
Ganoth et al., "A multicomponent system that degrades proteins conjugated to ubiquitin. Resolution of factors and evidence for ATP-dependent complex formation," J Biol Chem. 263(25):12412-12419 (1988).
Schuppan, "Current concepts of celiac disease pathogenesis," Gastroenterology. 119(1):234-242 (2000).
Hayashi et al., "NOD mice are defective in proteasome production and activation of NF-kappaB," Mol Cell Biol. 19(12):8646-8659 (1999).
Terada et al., "Bone marrow cells adopt the phenotype of other cells by spontaneous cell fusion," Nature. 416:542-545 (2002).
Serrano et al., "Non-HLA associations with autoimmune diseases," Autoimmun Rev. 5:209-214 (2006).
Serup et al., "Islet and stem cell transplantation for treating diabetes," BMJ. 322:29-32 (2001).
Hyafil et al., "Dissociation and exchange of the beta$_2$-microglobulin subunit of HLA-A and HLA-B antigens," Proc Natl Acad Sci USA. 76(11):5834-5838 (1979).
Bunting et al., "Enforced P-glycoprotein pump function in murine bone marrow cells results in expansion of side population stem cells in vitro and repopulating cells in vivo," Blood. 96(3):902-909 (2000).
Gupta, "Molecular steps of tumor necrosis factor receptor-mediated apoptosis," Curr Mol Med. 1(3):317-324 (2001).
Shehadeh et al., "Repeated BCG vaccination is more effective than a single dose in preventing diabetes in non-obese diabetic (NOD) mice," Isr J Med Sci. 33(11):711-715 (1997).
Jackson et al., "Hematopoietic potential of stem cells isolated from murine skeletal muscle," Proc Natl Acad Sci USA. 96(25):14482-14486 (1999).
Macchi et al., "Impaired apoptosis in mitogen-stimulated lymphocytes of patients with multiple sclerosis," NeuroReport. 10(25):399-402 (1999).
Faustman et al., "Stem cells in the spleen: Therapeutic potential for Sjogren's syndrome, type I diabetes, and other disorders," available in PMC Jul. 21, 2014, published in final edited form as: Int J Biochem Cell Biol. 42(10):1576-9 (2010) (8 pages).
Singh et al., "Can progression of IDDM be prevented in newly diagnosed patients by BCG immunotherapy?" Diabetes Metab Rev. 13(4):320-321 (1997).
Office Action and English Translation for Chinese Patent Application No. 201480068827.4, dated Mar. 24, 2017 (20 pages).
EPO Communication pursuant to Article 94(3) EPC for European Application No. 12005556.1, dated Jul. 2, 2015 (7 pages).
Hymowitz et al., "Toward small-molecule agonists of TNF receptors," Nat Chem Biol. 1(7):353-354 (2005).
Sreenan et al., "Increased beta-Cell proliferation and reduced mass before diabetes onset in the nonobese diabetic mouse," Diabetes. 48:989-996 (1999).
Koarada et al., "B Cells lacking RP105, a novel B cell antigen, in systemic lupus erythematosus," Arthritis & Rheumatism. 42(12):2593-600 (1999).
Moreland et al., "Etanercept therapy in rheumatoid arthritis: a randomized, controlled trial," Ann Intern Med. 130(6):478-486 (1999).
Storms et al., "Hoechst dye efflux reveals a novel CD7+CD34– lymphoid progenitor in human umbilical cord blood," Blood. 96(6):2125-2133 (2000).
Supplementary Partial European Search Report for European Application No. 04817543, dated Oct. 6, 2009 (4 pages).
Kwon et al., "Evidence for involvement of the proteasome complex (26S) and NFkappaB in IL-1beta-induced nitric oxide and prostaglandin production by rat islets and RINm5F Cells," Diabetes. 47:583-591 (1998).
Foulis, "C.L. Oakley lecture (1987). The pathogenesis of beta cell destruction in Type I (insulin-dependent) diabetes mellitus," J Pathol. 152(3):141-148 (1987).
Kanzler et al., "Hox11 acts cell autonomously in spleen development and its absence results in altered cell fate of mesenchymal spleen precursors," Devel Biol. 234:231-243 (2001).
Tamura et al., "In vivo differentiation of stem cells in the aorta-gonad-mesonephros region of mouse embryo and adult bone marrow," Exp Hematol. 30(8):957-966 (2002) (Abstract Only).

(56) References Cited

OTHER PUBLICATIONS

Lapchak et al., "Tumor necrosis factor production is deficient in diabetes-prone BB rats and can be corrected by complete Freund's adjuvant: A possible immunoregulatory role of tumor necrosis factor in the prevention of diabetes," Clin Immunol Immunopathol. 65(2):129-134 (1992).
Dilts et al., "Autoimmune diabetes: The involvement of benign and malignant autoimmunity," J Autoimmun. 12:229-232 (1999).
Wang et al., "Prevention of recurrence of IDDM in islet-transplanted diabetic NOD mice by adjuvant immunotherapy," Diabetes. 41:114-117 (1992).
Beers et al., Disorders of Carbohydrate Metabolism: Diabetes Mellitus. *The Merck Manual of Diagnosis and Therapy, 17th Ed.* Merck Research Laboratories, 165-171 (1999) (5 pages).
Jones et al., "The clinical utility of C-peptide measurement in the care of patients with diabetes," Diabet Med. 30(7):803-17 (2013).
Hoffmann et al. "Large-scale in vitro expansion of polyclonal human CD4(+)CD25$^{high}$ regulatory T cells," Blood. 104(3):895-903 (2004).
Kwon et al., "Interleukin-1beta-induced nitric oxide synthase expression by rat pancreatic beta-cells: Evidence for the involvement of nuclear factor kappaB in the signaling mechanism," Endocrinology. 136(11):4790-4795 (1995).
Townsley et al., "Dominant-negative cyclin-selective ubiquitin carrier protein E2-C/UbcH10 blocks cells in metaphase," Proc Natl Acad Sci USA. 94:2362-2367 (1997).
Aranda et al., "Analysis of intestinal lymphocytes in mouse colitis mediated by transfer of CD4+, CD45RB$^{high}$ T Cells to SCID recipients," J Immunol. 158(7):3464-3473 (1997).
Robinson et al., "Elevated levels of cysteine protease activity in saliva and salivary glands of the nonobese diabetic (NOD) mouse model for Sjögren Syndrome," Proc Natl Acad Sci USA. 94:5767-5771 (1997).
Lipsky et al., "Infliximab and methotrexate in the treatment of rheumatoid arthritis," N Engl J Med. 343:1594-1602 (2000).
Van der Kooy et al., "Why stem cells?," Science. 287:1439-1441 (2000).
Bill et al., "Use of soluble MHC class II/peptide multimers to detect antigen-specific T cells in human disease," Arthritis Res. 4:261-265 (2002).
Aristarkhov et al., "E2-C, a cyclin-selective ubiquitin carrier protein required for the destruction of mitotic cyclins," Proc Natl Acad Sci USA. 93(9):4294-9 (1996).
Shihabuddin et al., "Adult spinal cord stem cells generate neurons after transplantation in the adult dentate gyrus," J Neurosci. 20(23):8727-8735 (2000).
Grilli et al., "Neuroprotection by aspirin and sodium salicylate through blockade of NF-kappaB activation," Science. 274:1383-1385 (1996).
Murthi et al., "Novel homeobox genes are differentially expressed in placental microvascular endothelial cells compared with macrovascular cells," Placenta. 29(7):624-630 (2008) (1 page) (Abstract only).
Boches et al., "Role for the adenosine triphosphate-dependent proteolytic pathway in reticulocyte maturation," Science. 215:978-980 (1982).
Baeza et al., "Pancreatic regenerating gene overexpression in the nonobese diabetic mouse during active diabetogenesis," Diabetes. 45(1):67-70 (1996) (5 pages).
Okubo et al., "Homogeneous expansion of human T-regulatory cells via tumor necrosis factor receptor 2," Sci Rep. 3:3153 (2013) (11 pages).
Pestano et al., "Inactivation of misselected CD8 T cells by CD8 gene methylation and cell death," Science. 284(5417):1187-91 (1999).
Faustman, "Why were we wrong for so long? The pancreas of type 1 diabetic patients commonly functions for decades," Diabetologia. 57(1):1-3 (2014).

Brodbeck et al., "Genetic determination of nephrogenesis: the Pax/Eya/Six gene network," Pediatr Nephrol. 19(3):249-255 (2004) (1 page) (Abstract Only).
Enger et al., "The Hippo signaling pathway is required for salivary gland development and its dysregulation is associated with Sjögren's-like disease," available in PMC May 1, 2014, published in final edited form as: Lab Invest. 93(11):1203-18 (2013) (27 pages).
Caetano et al., "Effect of methotrexate (MTX) on NAD(P)+ dehydrogenases of HeLa cells: malic enzyme, 2-oxoglutarate and isocitrate dehydrogenases," Cell Biochem Funct. 15(4):259-264 (1997).
Martinez-Gamboa et al., "Gene expression of catalytic proteasome subunits and resistance toward proteasome inhibition of B lymphocytes from patients with primary Sjögren syndrome," J Rheumatol. 40(5):663-73 (2013).
Osorio et al., "Beta-2 microglobulin gene disruption prolongs murine islet allograft survival in NOD mice," Transplant Proc. 26(2):752 (1994).
Faustman, "EBV infection and anti-CD3 treatment for Type 1 diabetes: bad cop, good cop?" available in PMC Jul. 2, 2014, published in final edited form as: Expert Rev Clin Immunol. 9(2):95-7 (2013) (4 pages).
Declaration of Denise Faustman, M.D., Ph.D., from U.S. Appl. No. 10/851,983, dated Jul. 3, 2007 (7 pages).
Wang et al., "Persistence of prolonged C-peptide production in type 1 diabetes as measured with an ultrasensitive C-peptide assay," Diabetes Care. 35(3):465-70 (2012).
Dear et al., "The Hox11 gene is essential for cell survival during spleen development," Development. 121:2909-2915 (1995).
Burger et al., "Novel automated blood separations validate whole cell biomarkers," PLoS One. 6(7):e22430 (2011) (11 pages).
EPO Communication pursuant to Article 94(3) EPC for European Application No. 00914899.0, dated May 25, 2012 (9 pages).
Al-Awqati et al., "Stem cells in the kidney," Kidney Int. 61(2):387-95 (2002).
Faustman et al., "TNF Receptor 2 and Disease: Autoimmunity and Regenerative Medicine," Front Immunol. 4:478 (2013) (8 pages).
Morawietz et al., "Expression of proteasomal immunosubunit beta1i is dysregulated in inflammatory infiltrates of minor salivary glands in Sjögren's syndrome," J Rheumatol. 36(12):2694-703 (2009).
Eytan et al., "ATP-dependent incorporation of 20S protease into the 26S complex that degrades proteins conjugated to ubiquitin," Proc Natl Acad Sci USA. 86:7751-7755 (1989).
Faustman et al., "The primacy of CD8 T lymphocytes in type 1 diabetes and implications for therapies," J Mol Med (Berl). 87(12):1173-8 (2009) (6 pages).
Extended European Search Report for European Application No. 12005556.1, dated Sep. 2, 2014 (8 pages).
Faustman, "Immunotherapy on trial for new-onset type 1 diabetes," N Engl J Med. 359(18):1956-8 (2008).
Fu et al., "Defective major histocompatibility complex class I expression on lymphoid cells in autoimmunity," J Clin Invest. 91:2301-2307 (1993).
Lonyai et al., "Fetal Hox11 expression patterns predict defective target organs: a novel link between developmental biology and autoimmunity," available in PMC Jul. 30, 2014, published in final edited form as: Immunol Cell Biol. 86(4):301-9 (2008) (19 pages).
Sarin et al., "Cytotoxic effect of TNF and lymphotoxin on T lymphoblasts," J Immunol. 155:3716-3718 (1995).
Faustman, "Permanent reversal of diabetes in NOD mice," Science. 317(5835):196 (2007).
Graves et al., "Lack of association between early childhood immunizations and beta-cell autoimmunity," Diabetes Care. 22:1694-7 (1999).
Faustman, "Reversal of type 1 diabetes in mice," N Engl J Med. 356(3):311-2 (2007).
Goldberg, "Functions of the proteasome: The lysis at the end of the tunnel," Science. 268:522-523 (1995).
Horwitz et al., "Recombinant bacillus Calmette-Guérin (BCG) vaccines expressing the *Mycobacterium tuberculosis* 30-kDa major secretory protein induce greater protective immunity against tuber-

(56) References Cited

OTHER PUBLICATIONS culosis than conventional BCG vaccines in a highly susceptible animal model," Proc Natl Acad Sci USA. 97(35):13853-13858 (2000).
Dale et al., "A role for transcription factor NF-kappaB in autoimmunity: possible interactions of genes, sex, and the immune response," Adv Physiol Educ. 30(4):152-8 (2006).
Miller et al., "Both the Lyt-2+ and L3T4+ T cell subsets are required for the transfer of diabetes in nonobese diabetic mice," J Immunol. 140(3):52-8 (1988).
Ljunggren et al., "MHC class I expression and CD8+ T cell development in TAP1/beta$_2$-microglobulin double mutant mice," Int Immunol. 7(6):975-984 (1995).
Jarrett et al., "Anti-tumor necrosis factor-alpha therapy-induced vasculitis: case series," J Rheumatol. 30(10):2287-91 (2003) (1 page) (Abstract only).
Kühtreiber et al., "Methods to characterize lymphoid apoptosis in a murine model of autoreactivity," J Immunol Methods. 306(1-2):137-50 (2005).
Jacob et al., "Prevention of diabetes in nonobese diabetic mice by tumor necrosis factor (TNF): Similarities between TNF-alpha and interleukin 1," Proc Natl Acad Sci USA. 87:968-972 (1990).
Faustman, "Regenerative medicine: Stem cell research turns to the spleen," Discov Med. 5(29):447-9 (2005).
Kouskoff et al., "Organ-specific disease provoked by systemic autoimmunity," Cell. 87(5):811-22 (1996) (1 page) (Abstract only).
Kodama et al., "Diabetes and stem cell researchers turn to the lowly spleen," Sci Aging Knowledge Environ. 2005(3):pe2 (2005) (7 pages).
Tavernier et al., "Analysis of the structure-function relationship of tumour necrosis factor. Human/mouse chimeric TNF proteins: general properties and epitope analysis," J Mol Biol. 211(2):493-501 (1990).
Trowsdale et al., "Sequences encoded in the class II region of the MHC related to the 'ABC' superfamily of transporters," Nature. 348(6303):741-4 (1990).
Li et al., "Reduced expression of peptide-loaded HLA class I molecules on multiple sclerosis lymphocytes," Ann Neurol. 38:147-154 (1995).
Vidal-Puig et al., "Tolerance to peripheral tissue is transient and maintained by tissue-specific class I expression," Transplant Proc. 26(6):3314-6 (1994).
Lewis et al., "Integrins regulate the apoptotic response to DNA damage through modulation of p53," Proc Natl Acad Sci USA. 99(6):3627-3632 (2002).
Rabinovitch et al., "Tumor necrosis factor mediates the protective effect of Freund's adjuvant against autoimmune diabetes in BB rats," J Autoimmun. 8(3):357-366 (1995).
Baeuerle et al., "NF-kappaB: Ten years after," Cell. 87(1):13-20 (1996).
Lanza et al., "Transplantation of encapsulated canine islets into spontaneously diabetic BB/Wor rats without immunosuppression," Endocrinology. 131(2):637-642 (1992).
Watt et al., "Out of Eden: stem cells and their niches," Science. 287:1427-30 (2000).
Ashton-Rickardt et al., "Peptide contributes to the specificity of positive selection of CD8+ T Cells in the thymus," Cell. 73(5):1041-9 (1993).
Corbett et al., "Nitric oxide mediates cytokine-induced inhibition of insulin secretion by human islets of Langerhans," Proc Natl Acad Sci USA. 90(5):1731-1735 (1993).
Cole et al., "Two ParaHox genes, SpLox and SpCdx, interact to partition the posterior endoderm in the formation of a functional gut," Development. 136(4):541-549 (2009).
Brás et al., "Diabetes-prone NOD mice are resistant to *Mycobacterium avium* and the infection prevents autoimmune disease," Immunology. 89:20-25 (1996).
Bercovici et al., "Systemic administration of agonist peptide blocks the progression of spontaneous CD8-mediated autoimmune diabetes in transgenic mice without bystander damage," J Immunol. 165(1):202-10 (2000) (10 pages).
Markiewicz et al., "Long-term T cell memory requires the surface expression of self-peptide/major histocompatibility complex molecules," Proc Natl Acad Sci USA. 95(6):3065-70 (1998).
EPO Communication Pursuant to Article 94(3) EPC issued in European Patent Application No. 03762242.0, dated Oct. 30, 2009 (2 pages).
Ramiya et al., "Reversal of insulin-dependent diabetes using islets generated in vitro from pancreatic stem cells," Nat Med. 6(3):278-282 (2000).
Gage et al., "Multipotent progenitor cells in the adult dentate gyrus," J Neurobiol. 36:249-266 (1998).
Van Nocker et al., "The multiubiquitin-chain-binding protein Mcb1 is a component of the 26S proteasome in *Saccharomyces cerevisiae* and plays a nonessential, substrate-specific role in protein turnover," Mol Cell Biol. 16(11):6020-6028 (1996).
Hsu et al., "TRADD-TRAF2 and TRADD-FADD interactions define two distinct TNF receptor 1 signal transduction pathways," Cell. 84:299-308 (1996).
Fischer et al., "An improved flow cytometric assay for the determination of cytotoxic T lymphocyte activity," J Immunol Methods. 259:159-169 (2002).
Krause et al., "Multi-organ, multi-lineage engraftment by a single bone marrow-derived stem cell," Cell. 105:369-377 (2001).
Aldrich et al., "Positive selection of self- and alloreactive CD8+ T cells in Tap-1 mutant mice," Proc Natl Acad Sci USA. 91(14):6525-8 (1994).
Bleumink et al., "Etanercept-induced subacute cutaneous lupus erythematosus," Rheumatology. 40:1317-1319 (2001).
Baldwin, "The NF-kappaB and IkappaB proteins: new discoveries and insights," Ann Rev Immunol. 14:649-683 (1996).
Dieguez-Acuña et al., "Proteomics identifies multipotent and low oncogenic risk stem cells of the spleen," Int J Biochem Cell Biol. 42(10):1651-1660 (2009) (10 pages).
Faustman et al., "Treatment of primary Sjögren syndrome with rituximab," Ann Intern Med. 161(5):376-80 (2014) (6 pages).
Baxter et al., "Mycobacteria precipitate an SLE-like syndrome in diabetes-prone NOD mice," Immunology. 83(2):227-231 (1994).
Kodama et al., "Regenerative medicine: A radical reappraisal of the spleen," Trends Mol Med. 11(6):271-276 (2005).
Sears et al., "NF-kappaB p105 processing via the ubiquitin-proteasome pathway," J Biol Chem. 273(3):1409-1419 (1998).
Matsumoto et al., "Liver organogenesis promoted by endothelial cells prior to vascular function," Science. 294:559-563 (2001).
Stephens et al., "Protection of NIT-1 pancreatic beta-cells from immune attack by inhibition of NF-kappaB," J Autoimmun. 10:293-298 (1997).
Mestas et al., "Of mice and not men: Differences between mouse and human immunology," J Immunol. 172:2731-2738 (2004).
Tran et al., "Reversal of Sjögren's-like syndrome in non-obese diabetic mice," Ann Rheum Dis. 66:812-814 (2007).
Petersen et al., "Bone marrow as a potential source of hepatic oval cells," Science. 284(5417):1168-70 (1999).
Orlowski, "The multicatalytic proteinase complex, a major extralysosomal proteolytic system," Biochemistry. 29(45):10289-10297 (1990).
EPO Communication Pursuant to Rules 161 (2) and 162 EPC for International Application No. PCT/US2014/015101, dated Oct. 15, 2015 (2 pages).
Sandborn, "Strategies targeting tumor necrosis factor in Crohn's disease," Acta Gastroenterol Belg. 64(2):170-2 (2001) (1 page) (Abstract only).
Schatz et al., "Defective inducer T-cell function before the onset of insulin-dependent diabetes mellitus," J Autoimmun. 4:125-136 (1991).
Faustman et al., "TNF receptor 2 pathway: drug target for autoimmune diseases," Nat Rev Drug Discov. 9(6):482-93 (2010).
Miyazaki et al., "Predominance of T lymphocytes in pancreatic islets and spleen of pre-diabetic non-obese diabetic (NOD) mice: A longitudinal study," Clin Exp Immunol. 60:622-630 (1985).
Kieran et al., "The DNA binding subunit of NF-kappaB is identical to factor KBF1 and homologous to the rel oncogene product," Cell. 62:1007-18 (1990).

(56) References Cited

OTHER PUBLICATIONS

Toma et al., "Isolation of multipotent adult stem cells from the dermis of mammalian skin," Nat Cell Bio. 3:778-784 (2001).
Elliott et al., "Effect of bacille Calmette-Guérin vaccination on C-peptide secretion in children newly diagnosed with IDDM," Diabetes Care. 21 (10):1691-1693 (1998).
Baik et al., "BCG vaccine prevents insulitis in low dose streptozotocin-induced diabetic mice," Diabetes Res Clin Pract. 46(2):91-97 (1999).
McGuire et al., "An enzyme related to the high molecular weight multicatalytic proteinase, macropain, participates in a ubiquitin-mediated, ATP-stimulated proteolytic pathway in soluble extracts of BHK 21/C13 fibroblasts," Biochim Biophys Acta. 967:195-203 (1988).
Ristori et al., "Use of Bacille Calmette-Guérin (BCG) in multiple sclerosis," Neurology. 53:1588-1589 (1999).
Anderson et al., "Studies on the cytophilic properties of human beta2 microglobulin," J Immunol. 114(3):997-1000 (1975).
Shohami et al., "Dual role of tumor necrosis factor alpha in brain injury," Cytokine Growth Factor Rev. 10:119-130 (1999).
Mayer-Proschel et al., "Isolation of lineage-restricted neuronal precursors from multipotent neuroepithelial stem cells," Neuron. 19:773-785 (1997).
Nomikos et al., "Combined treatment with nicotinamide and desferrioxamine prevents islet allograft destruction in NOD mice," Diabetes. 35:1302-1304 (1986).
International Search Report and Written Opinion for International Application No. PCT/US16/49064, dated Jan. 5, 2017 (19 pages).
Chi-Chieh Lai et al., "Reaction at the Bacillus Calmette-Guerin Inoculation Site in Patients with Kawasaki Disease," Pediatr Neonatol. 54(1):43-8 (2013).
International Preliminary Report on Patentability for International Patent Application No. PCT/US2015/030282, dated Nov. 24, 2016 (12 pages).
Van Dam et al., "BCG lowers plasma cholesterol levels and delays atherosclerotic lesion progression in mice," Atherosclerosis. 251:6-14 (2016).
Alexandroff et al.,: "BCG immunotherapy of bladder cancer: 20 years on," Lancet. 353(9165):1689-94 (1999).
Vagima et al., "MT1-MMP and RECK are involved in human CD34+ progenitor cell retention, egress, and mobilization," J Clin Invest. 119(3):492-503 (2009).
Partial Supplementary Search Report for European Patent Application No. 16852634.1, dated Feb. 15, 2019 (21 pages).
Faustman et al., "Proof-of-concept, randomized, controlled clinical trial of Bacillus-Calmette-Guerin for treatment of long-term type 1 diabetes," PLoS One. 7(8):e41756 (2012) (16 pages).
Faustman, "EBV infection and anti-CD3 treatment for Type 1 diabetes: bad cop, good cop?" Expert Rev Clin Immunol. 9(2):95-7 (2013).
International Search Report and Written Opinion for International Application No. PCT/US2016/054535, dated Dec. 20, 2016 (30 pages).
International Preliminary Report on Patentability for International Application No. PCT/US2016/054535, dated Apr. 12, 2018 (24 pages).

\* cited by examiner

Statistically significant: p-value < .01

Statistically significant: p-value < .00001

FIG. 4A

| BIOCHEMICAL | SUPER PATHWAY | SUB PATHWAY | Avg(BCGpost) | Avg(Placebopost) | Ttest |
|---|---|---|---|---|---|
| N-acetylalanine | Amino Acid | Alanine and Aspartate Metabolism | 1.1408 | 0.9094 | 5.689E-13 |
| N-acetylaspartate (NAA) | Amino Acid | Alanine and Aspartate Metabolism | 1.2051 | 0.9409 | 4.198E-05 |
| N-acetylserine | Amino Acid | Glycine, Serine and Threonine Metabolism | 1.1829 | 0.8648 | 4.241E-14 |
| N-acetylthreonine | Amino Acid | Glycine, Serine and Threonine Metabolism | 1.1042 | 0.9417 | 1.315E-06 |
| N-acetyl-3-methylhistidine | Amino Acid | Histidine Metabolism | 1.3040 | 0.4930 | 2.496E-04 |
| N-acetylhistidine | Amino Acid | Histidine Metabolism | 1.0469 | 0.8553 | 0.025 |
| N-acetylvaline | Amino Acid | Leucine, Isoleucine and Valine Metabolism | 1.1089 | 1.0009 | 0.050 |
| N2-acetyllysine | Amino Acid | Lysine Metabolism | 1.0300 | 0.6585 | 0.047 |
| N-acetylmethionine | Amino Acid | Methionine, Cysteine, SAM and Taurine Metabolism | 1.3010 | 0.8034 | 3.034E-11 |
| N-acetylphenylalanine | Amino Acid | Phenylalanine and Tyrosine Metabolism | 0.8704 | 1.1155 | 1.094E-04 |
| N-acetyltryptophan | Amino Acid | Tryptophan Metabolism | 0.7559 | 1.1795 | 1.167E-07 |
| N-acetylarginine | Amino Acid | Urea cycle; Arginine and Proline Metabolism | 0.9761 | 1.1284 | 0.041 |

FIG. 6  Effects of BCG on lipogenic and lipolytic enzyme expression

| Gene | T1D - Time 0 | T1D - Time 48 hours | Control - Time 0 | Control - Time 48 hours | |
|---|---|---|---|---|---|
| IL6 | 0.54 | 921.60 | 0.72 | 959.87 | Cytokines |
| TNF | 18.06 | 157.35 | 15.78 | 287.76 | |
| IFNG | 0.54 | 101.15 | 1.20 | 120.74 | |
| ACACA | 19.32 | 0.00 | 12.91 | 6.04 | Lipogenic Factors |
| ACACB | 31.83 | 22.48 | 19.37 | 16.10 | |
| FASN | 96.04 | 56.20 | 80.33 | 58.36 | |
| SCD | 8.58 | 33.72 | 3.35 | 44.27 | |
| ME1 | 4.65 | 11.24 | 1.91 | 4.02 | |
| G6PD | 470.37 | 11.24 | 643.14 | 94.58 | |
| CPT1A | 159.35 | 202.30 | 135.80 | 42.26 | Lipolytic Factors |
| CPT1B | 8.76 | 0.00 | 5.98 | 8.05 | |
| CPT1C | 0.36 | 0.00 | 0.48 | 0.00 | |
| ACOX1 | 88.89 | 44.96 | 157.56 | 62.38 | |
| ACOX2 | 0.54 | 0.00 | 2.63 | 0.00 | |
| ACOX3 | 27.72 | 44.96 | 26.78 | 60.37 | |
| UCP2 | 1038.03 | 213.54 | 968.06 | 144.89 | |
| ADIPOR1 | 253.2466419 | 157.3468433 | 413.3811139 | 173.0585344 | Adiponectin Receptors |
| ADIPOR2 | 111.6002151 | 44.95624094 | 98.74285717 | 76.4677245 | |

| T1D Study Groups | P-values |
|---|---|
| BCG vs. Placebo | 0.0008 |
| BCG vs. Reference | 0.02 |
| Placebo vs. Reference | 0.73 |

Adenine

N6-Carbamoylthreonyadenosine

Methylguanine

FIG. 9I
| Metabolites Glucose Metabolism | Controls vs T1D p-value | Pre-BCG vs Post-BCG T1D p-value |
|---|---|---|
| Lactate | 4.13E-01 | 1.38E-02 |
| 1,5-Anhydroglucitol | 1.30E-11 | 7.00E-03 |
| alpha-Ketobutyrate | 2.55E-02 | 7.76E-03 |
| 2-Hydroxybutyrate | 2.81E-02 | 3.38E-01 |
| Purine Synthesis | | |
| Adenine | 2.39E-03 | 2.89E-02 |
| N6-Carbamoylthreonyladenosine | 2.77E-03 | 1.34E-02 |
| Methylguanine | 1.50E-04 | 1.35E-02 |
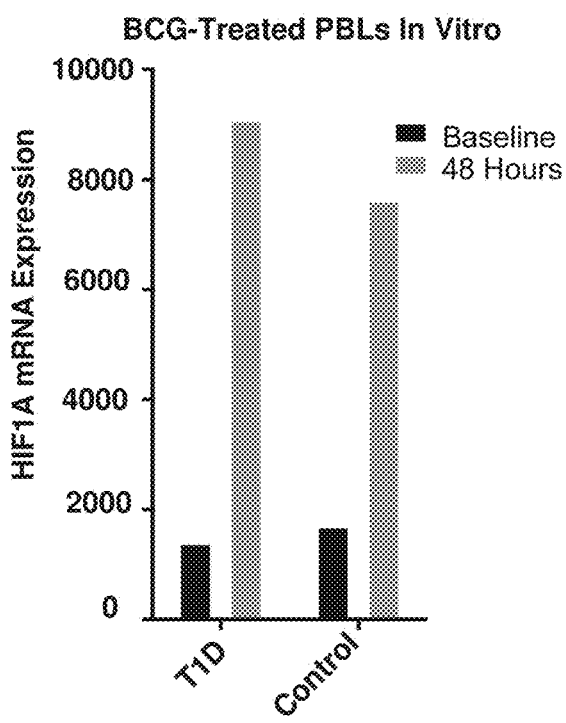
FIG. 9J
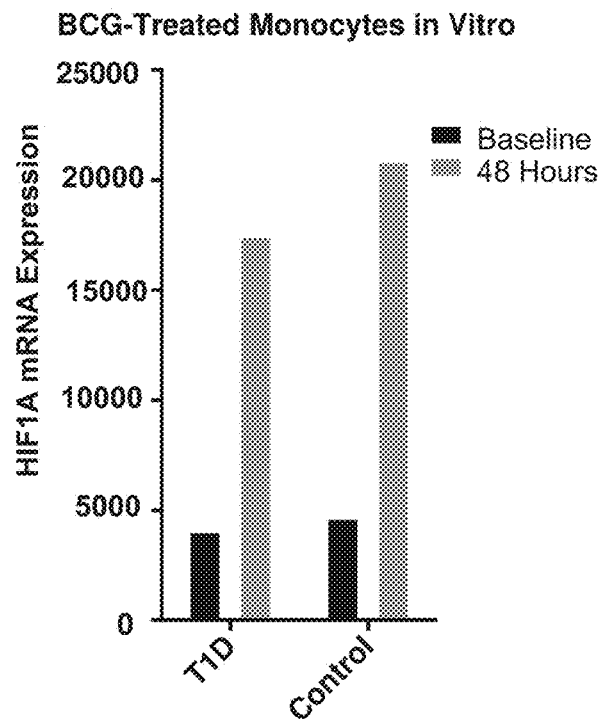
FIG. 9K Time (weeks)

METHODS OF TREATING AND DIAGNOSING DISEASE USING BIOMARKERS FOR BCG THERAPY

FIELD OF THE INVENTION

The invention relates to methods of treating diseases, such as hypercholesterolemia, by administering Bacillus Calmette-Guerin (BCG), as well as methods for diagnosing a subject as having disease or needing treatment, e.g., with BCG, based on genomic, proteomic, and metabolomic analyses.

BACKGROUND OF THE INVENTION

Elevated levels of cholesterol and other serum lipids, such as low-density lipoproteins (LDLs) and triglycerides, represent a prominent threat to human health and have been correlated with the onset of a variety of diseases. Among the conditions associated with high cholesterol are heart disease and stroke, the pathology of each of which is characterized by a reduction in the circulation of blood to vital bodily organs due to resistance imposed on the flow of blood through hardened arteries. According to the World Health Organization, approximately a third of ischemic heart disease cases worldwide are attributable to high cholesterol. Diseases associated with high serum cholesterol levels remain challenging indications for conventional therapies, and there is currently a need for new therapeutic modalities for restoring blood serum lipid levels to within a healthy range.

SUMMARY OF THE INVENTION

The present invention provides methods for modulating serum lipid levels, such as the levels of cholesterol, LDLs, HDLs, and triglycerides, by administration of BCG (e.g., *Mycobacterium bovis*), to a subject (e.g., a mammalian subject, such as a human). The invention also features methods for preventing the onset of elevated cholesterol, LDL, and triglyceride levels by administering BCG to a subject prone to the development of elevated levels of these serum lipids, as well as methods of treating and preventing a wide range of diseases associated with the accumulation of these substances. The invention additionally provides methods for diagnosing various diseases in a subject, such as immunological and neurological disorders, as well as pathologies associated with heightened levels of cholesterol, LDLs, and/or triglycerides, by assessing the presence, amount, or concentration of one or more biomarkers in a subject. The diagnostic methods described herein can be used not only to determine whether a subject has a particular disease or condition, but also to evaluate the likelihood that the subject will respond to treatment with a therapeutic agent (e.g., BCG) or will benefit from treatment with one or more additional doses of a therapeutic agent (e.g., BCG).

In a first aspect, the invention features a method of reducing the level of cholesterol, LDL, or triglycerides in a subject in need thereof by administering an effective amount of BCG to the subject. In another aspect, the invention relates to a method of increasing the level of HDL in a subject in need thereof by administering an effective amount of BCG to the subject. In some embodiments of the invention, the administration of BCG lowers the level of total cholesterol in the subject by 1%, 5%, or more. In some cases, the subject has a total cholesterol level of about 100 mg/dL or greater, such as a total cholesterol level of about 129 mg/dL or greater. Additionally or alternatively, the administration of BCG may lower the level of LDLs in the subject by 1%, 5%, or more. In some cases, the subject has a LDL level of about 80 mg/dL or greater. In certain embodiments, the administration of BCG elevates the level of HDLs in the subject by 1%, 5%, or more. In particular cases, the subject has a HDL level of about 40 mg/dL or below. Additionally or alternatively, the subject may have a triglyceride level of about 100 mg/dL or greater. In certain embodiments, the subject has a triglyceride level of between about 100 mg/dL and about 500 mg/dL and/or a ratio of total cholesterol level to HDL level of about 5 or greater. In other embodiments, the subject has a ratio of total cholesterol level to HDL level of between about 3 and about 10. In some embodiments, the invention features methods of stabilizing the level of cholesterol, LDL, or triglycerides in a subject, for instance, by administration of BCG as described herein. In some embodiments, the invention features methods of preventing an increase in the level of cholesterol, LDL, or triglycerides in a subject, for instance, by administration of BCG as described herein. In some embodiments, the invention features methods of stabilizing the level of HDL in a subject, for instance, by administration of BCG as described herein. In some embodiments, the invention features methods of preventing a decrease in the level of HDL, for instance, by administration of BCG as described herein.

The methods of the invention can also be applied to a subject that has a total cholesterol, LDL and/or triglyceride level that is higher than that which has previously been observed for the subject. For instance, the subject may have previously been observed as having a total cholesterol level less than about 180 mg/dL. In some cases, the subject may have previously been observed as having a LDL level of less than about 100 mg/dL and/or a triglyceride level of less than about 150 mg/dL.

In embodiments of any of the above-described aspects of the invention, the subject may be suffering from a disease associated with an elevated level of cholesterol, such as hypercholesterolemia, hyperlipidemia, coronary heart disease, peripheral arterial disease (PAD), peripheral vascular disease, hypertension, stroke, diabetes, metabolic syndrome, obesity, or insulin resistance. BCG may be administered to the subject in an amount sufficient to alleviate or reduce a symptom associated with the disease. For instance, the symptom may be an elevated level of a substance such as lactate dehydrogenase (LDH), LDL, or triglycerides. The administration of BCG may serve to reduce the level of one or more of these substances. In other embodiments, the symptom may be angina, arrhythmia, and heart failure. In these cases, the administration of BCG may alleviate or reduce the angina, arrhythmia, or heart failure.

In some embodiments of the invention, BCG is administered to a subject in conjunction with a hypolipidemic agent, such as a HMG-CoA reductase inhibitor (e.g., atorvastatin, cerivastatin, fluvastatin, lovastatin, mevastatin, pitavastatin, pravastatin, rosuvastatin, simvastatin, or combinations thereof), niacin, a fibric acid derivative (e.g., fenofibrate or gemfibrozil), a cholesterol absorption inhibitor (e.g., ezetimibe), and/or a lipolytic agent (e.g., norepinephrine, isoproterenol, forskolin, bucladesine, or theophylline). In some cases, BCG is admixed with the hypolipidemic agent (e.g., in a single pharmaceutical composition), while in other cases, BCG is administered separately from the hypolipidemic agent (e.g., consecutively and/or by a different route of administration).

In another aspect, the invention provides a method of treating a subject that has a disease, such as an autoimmune disease or neurological condition as described herein, by administering BCG to the subject. In some embodiments, the subject has been previously diagnosed as having the disease, e.g., using methods known in the art.

In an additional aspect, the invention features a method of treating a subject that has previously been diagnosed as having a disease, such as an autoimmune disease or a neurological condition described herein, such that the subject has been diagnosed by:
  a) determining a quantity of methylated cytosine residues in a sample of nuclear DNA isolated from the subject; and
  b) comparing the quantity to a quantity of methylated cytosine residues in a reference sample (e.g., a sample isolated from a control subject not having the disease, such as a subject of the same age, gender, and/or weight), such that a determination that the quantity of methylated cytosine residues in the sample of nuclear DNA isolated from the subject is greater than the quantity of methylated cytosine residues in the reference sample indicates that the subject has the disease, the method having the step of administering BCG to the subject. In other aspects of the invention, a determination that the quantity of methylated cytosine residues in the sample of nuclear DNA isolated from the subject is less than the quantity of methylated cytosine residues in the reference sample indicates that the subject has the disease, and the method further includes administering an effective amount of BCG to the subject.

In another aspect, the invention provides a method of treating a subject that has previously been diagnosed as having a disease such as an autoimmune disease or a neurological condition, such that the subject has been diagnosed by:
  a) i) determining a level of one or more substances selected from the group consisting of an mRNA molecule encoding a cytokine or lipolytic protein, a protein selected from the group consisting of a cytokine and a lipolytic protein, an acetylated amino acid selected from the group consisting of N-acetylalanine, N-acetylaspartic acid, N-acetylserine, N-acetylthreonine, N-acetylhistidine, N-acetyl-3-methylhistidine, N-acetylvaline, and N-α-acetyllysine, and N-acetylmethionine, or a methylated metabolite selected from the group consisting of N-α-acetyl-3-methylhistidine, 3-methylglutaconic acid, 3-methylglutarylcarnitine, and N-ε-trimethyllysine in a sample from the subject; and
  (ii) comparing the level of the one or more substances to the level of the one or more substances in a reference sample (e.g., a sample isolated from a control subject not having the disease, such as a subject of the same age, gender, and/or weight), such that a determination that the level of the one or more substances in the sample from the subject having the disease is less than the level of the one or more substances in the reference sample indicates that the subject has the disease; or
  b) (i) determining a level of one or more substances selected from the group consisting of an mRNA molecule encoding a lipogenic protein, an adiponectin receptor, a lysine acetyltransferase, a histone acetyltransferase, a histone deacetylase, or a histone, a protein selected form the group consisting of a lipogenic protein, an adiponectin receptor, a lysine acetyltransferase, a histone acetyltransferase, a histone deacetylase, and a histone, or a methylated metabolite selected from the group consisting of 4-methyl-2-oxopentanoic acid and 3-methyl-2-oxobutyric acid in a sample from the subject; and
  (ii) comparing the level of the one or more substances to the level of the one or more substances in a reference sample (e.g., a sample isolated from a control subject not having the disease, such as a subject of the same age, gender, and/or weight), such that a determination that the level of the one or more substances in the sample from the subject having the disease is greater than the level of the one or more substances in the reference sample indicates that the subject has the disease, such that the method includes administering an effective amount of BCG to the subject.

In some cases, the autoimmune disease described above is type I diabetes, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Essential Mixed Cryoglobulinemia, Fibromyalgia-Fibromyositis, Graves' Disease, Guillain-Barré, Hashimoto's Thyroiditis, Hypothyroidism, Idiopathic Pulmonary Fibrosis, Idiopathic Thrombocytopenia Purpura (ITP), IgA Nephropathy, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, or Wegener's Granulomatosis.

In certain cases, the neurological condition described above is a brain tumor, a brain metastasis, a spinal cord injury, schizophrenia, epilepsy, Amyotrophic lateral sclerosis (ALS), Parkinson's disease, Autism, Alzheimer's disease, Huntington's disease, or stroke.

In an additional aspect, the invention provides a method of treating a subject having a disease selected from the group consisting of a brain tumor, a brain metastasis, schizophrenia, epilepsy, Autism, stroke, an allergy, allograft rejection, graft-versus-host disease, asthma, macular degeneration, muscular atrophy, a disease related to miscarriage, atherosclerosis, bone loss, a musculoskeletal disease, and obesity, by administering an effective amount of BCG to the subject. In some embodiments of the invention, the subject has been previously diagnosed as having the disease (e.g., using methods known in the art or by analysis of one or more biomarkers described herein, such as methylated cytosine residues in a nuclear gene of interest, such as FoxP3 or CD45, and/or a cytokine, lipolytic protein, lipogenic protein, adiponectin receptor, or an mRNA molecule encoding one of these proteins, and/or an acetylated amino acid or methylated metabolite such as those described herein).

In certain embodiments, the allergy is selected from the group consisting of food allergy, seasonal allergy, pet allergy, hives, hay fever, allergic conjunctivitis, poison ivy allergy oak allergy, mold allergy, drug allergy, dust allergy, cosmetic allergy, and chemical allergy.

In some cases, the allograft rejection is selected from the group consisting of skin graft rejection, bone graft rejection, vascular tissue graft rejection, ligament graft rejection, and organ graft rejection.

The ligament graft rejection described above may be selected from the group consisting of cricothyroid ligament graft rejection, periodontal ligament graft rejection, suspensory ligament of the lens graft rejection, palmar radiocarpal ligament graft rejection, dorsal radiocarpal ligament graft rejection, ulnar collateral ligament graft rejection, radial collateral ligament graft rejection, suspensory ligament of the breast graft rejection, anterior sacroiliac ligament graft rejection, posterior sacroiliac ligament graft rejection, sacrotuberous ligament graft rejection, sacrospinous ligament graft rejection, inferior pubic ligament graft rejection, superior pubic ligament graft rejection, anterior cruciate ligament graft rejection, lateral collateral ligament graft rejection, posterior cruciate ligament graft rejection, medial collateral ligament graft rejection, cranial cruciate ligament graft rejection, caudal cruciate ligament graft rejection, and patellar ligament graft rejection.

The organ graft rejection may be selected from the group consisting of heart graft rejection, lung graft rejection, kidney graft rejection, liver graft rejection, pancreas graft rejection, intestine graft rejection, and thymus graft rejection.

In some embodiments, the graft-versus-host disease may arise from a bone marrow transplant or transplant of one or more blood cells selected from the group consisting of hematopoietic stem cells, common myeloid progenitor cells, common lymphoid progenitor cells, megakaryocytes, monocytes, basophils, eosinophils, neutrophils, macrophages, T-cells, B-cells, natural killer cells, and dendritic cells.

In embodiments of the above methods of treatment, the method may further include administering to the subject an additional therapeutic agent. In some cases, the additional therapeutic agent is selected from the group consisting of tumor necrosis factor-alpha (TNFα), a tumor necrosis factor receptor 2 (TNFR2) agonist, an immunotherapy agent (e.g., an anti-CTLA-4 agent, an anti-PD-1 agent, an anti-PD-L1 agent, an anti-PD-L2 agent, a TNF-α cross-linking agent, a TRAIL cross-linking agent, a CD27 agent, a CD30 agent, a CD40 agent, a 4-1BB agent, a GITR agent, an OX40 agent, a TRAILR1 agent, a TRAILR2 agent, and a TWEAKR agent), and combinations thereof.

In embodiments of any of the above methods of treatment, the BCG may be administered in a unit dosage form including between about $5 \times 10^5$ and about $1 \times 10^7$ colony forming units (cfu) per 0.1 milligrams of BCG (e.g., between about $1 \times 10^6$ and about $6 \times 10^6$ cfu per 0.1 milligrams of BCG, such as between about $1.8 \times 10^6$ and about $3.9 \times 10^6$ cfu per 0.1 milligrams of BCG)

In some embodiments, administration of BCG modulates a methylation state of one or more deoxyribonucleotides in the subject. For instance, the administering may promote methylation or demethylation of one or more deoxyribonucleotides in the subject. The one or more deoxyribonucleotides may be located within a gene that encodes a transcription factor (e.g., FoxP3) or a protein that is expressed on the surface of a T-cell (e.g., CD45). In certain embodiments, the one or more deoxyribonucleotides include cytosine residues.

In some cases, the administration of BCG promotes an increase in the level of one or more proteins in the subject and/or the level of one or more mRNA molecules encoding these proteins. The proteins may include a cytokine, such as interleukin-6 (IL-6), tumor necrosis factor (TNF), or interferon-gamma (IFNγ). In other embodiments, the one or more proteins include a lipolytic protein, such as acyl co-enzyme A oxidase, carnitine palm itoyltransferase, lipase, or uncoupling protein.

In other embodiments, the administration of BCG may promote a decrease in the level of one or more proteins in the subject and/or the level of one or more mRNA molecules encoding these proteins. For instance, the one or more proteins may include a lipogenic protein, such as acetyl co-enzyme A carboxylase α, acetyl co-enzyme A carboxylase β, fatty acid synthase, glyceraldehydes-6-phosphate dehydrogenase, stearoyl-CoA saturase, malic enzyme, or glucose-6-phosphate dehydrogenase. In some embodiments, the one or more proteins include an adiponectin receptor, such as adiponectin receptor 1 or adiponectin receptor 2.

In some embodiments, the administration of BCG promotes acetylation of one or more amino acids in the subject, such as alanine, aspartic acid, serine, threonine, histidine, 3-methylhistidine, valine, lysine, or methionine. Additionally or alternatively, the administration may promote methylation of one or more metabolites in the subject, such as N-α-acetylhistidine, glutaconic acid, glutarylcarnitine, lysine, and cysteine. In some embodiments, the administration of BCG promotes demethylation of one or more metabolites in the subject, such as 4-methyl-2-oxopentanoic acid or 3-methyl-2-oxobutyric acid.

In some embodiments, the administration of BCG promotes a decrease in the level of one or more lysine acetyltransferases (KATs, such as KAT2A, KAT2B, KAT5, KAT6A, KAT6B, KAT7, or KAT8), histone acetyltransferases, histone deacetylases (HDACs, such as HDAC1, HDAC2, HDAC3, HDAC4, HDAC5, HDAC6, HDAC7, HDAC8, HDAC9, HDAC10, HDAC11, HDAC1P1, HDAC1P2, SIRT1, SIRT2, SIRT3, SIRT4, SIRT5, SIRT6, or SIRT7), or one or more histones (e.g., a H2A, H2B, H3, or H4 family histone).

In embodiments of any of the above-described methods of treatment, the subject may exhibit a reduction in total cholesterol of between about 1% and about 40% (e.g., between about 5% and about 40%) relative to a control subject not treated with the BCG (e.g., a control subject of the same age, sex, and/or weight of the subject being treated). In some cases, the subject exhibits this reduction in total cholesterol within about 3 months to about 7 years after being treated with the BCG. In some embodiments, the subject exhibits a reduction in LDL of between about 5% and about 60%, e.g., within about 3 months to about 7 years after being treated with the BCG. Additionally or alternatively, a subject may exhibit a reduction in glycated hemoglobin of between about 5% and about 30%, e.g., within about 2 weeks to about 7 years after being treated with the BCG. The reduction in cholesterol, LDLs, and/or glycated hemoglobin may be maintained, e.g., for between about 1 year and about 8 years, or more.

In another aspect, the invention provides a method of diagnosing a subject as having a disease, the method including:
  a) determining a quantity of methylated cytosine residues in a sample of nuclear DNA isolated from the subject; and
  b) comparing the quantity to a quantity of methylated cytosine residues in a reference sample (e.g., a sample isolated from a control subject not having the disease, such as a subject of the same age, gender, and/or weight), such that a determination that the quantity of methylated cytosine residues in the sample of nuclear DNA isolated from the subject is greater than or less than the quantity of methylated cytosine residues in the reference sample indicates that the subject has the disease.

The method may further include determining whether the subject is likely to respond to treatment with a therapeutic agent for the disease, such that a determination that the quantity of methylated cytosine residues in the sample of nuclear DNA isolated from the subject is greater than or less than the quantity of methylated cytosine residues in the reference sample indicates that the subject is likely to respond to the treatment. In some cases, the quantity of methylated cytosine residues in the sample of nuclear DNA isolated from the subject is greater than the quantity of methylated cytosine residues in the reference sample by 1% or more (e.g., by 5%, 10%, or more). In other embodiments, the quantity of methylated cytosine residues in the sample of nuclear DNA isolated from the subject is less than the quantity of methylated cytosine residues in the reference sample by 1% or more (e.g., by 5%, 10%, or more). In these cases, the methylated cytosine residues may be located within a gene that encodes a transcription factor (e.g., FoxP3) or a protein that is expressed on the surface of a T-cell (e.g., CD45).

In another aspect, the invention provides a method of determining whether a subject previously administered a therapeutic agent for the treatment of a disease would benefit from receiving one or more additional doses of the therapeutic agent, the method including:
  a) determining a quantity of methylated cytosine residues in a sample of nuclear DNA isolated from the subject; and
  b) comparing the quantity to a quantity of methylated cytosine residues in a reference sample (e.g., a prior sample that has been previously isolated from the subject),
such that a determination that the quantity of methylated cytosine residues in the sample of nuclear DNA isolated from the subject is within 10% of the quantity of methylated cytosine residues in the reference sample indicates that the subject would benefit from one or more additional doses of the therapeutic agent. In some cases, a determination that the quantity of methylated cytosine residues in the sample of nuclear DNA isolated from the subject is within 5% of (e.g., within 1% of or the same as) the quantity of methylated cytosine residues in the reference sample indicates that the subject would benefit from one or more additional doses of the therapeutic agent. In these cases, the methylated cytosine residues may be located within a gene that encodes a transcription factor (e.g., FoxP3) or a protein that is expressed on the surface of a T-cell (e.g., CD45). In some embodiments of the invention, the method includes isolating a polynucleotide including one or more cytosine residues and treating the polynucleotide with bisulfite. Optionally, the polynucleotide is then amplified using a polymerase chain reaction (PCR).

In an additional aspect, the invention provides a method of diagnosing a subject as having a disease, the method including:
  a) i) determining a level of one or more substances selected from the group consisting of an mRNA molecule encoding a cytokine or lipolytic protein, a protein selected from the group consisting of a cytokine and a lipolytic protein, an acetylated amino acid selected from the group consisting of N-acetylalanine, N-acetylaspartic acid, N-acetylserine, N-acetylthreonine, N-acetylhistidine, N-acetyl-3-methylhistidine, N-acetylvaline, and N-α-acetyllysine, and N-acetylmethionine, or a methylated metabolite selected from the group consisting of N-α-acetyl-3-methylhistidine, 3-methylglutaconic acid, 3-methylglutarylcarnitine, and N-ε-trimethyllysine in a sample from the subject; and
  (ii) comparing the level of the one or more substances to the level of the one or more substances in a reference sample (e.g., a sample isolated from a control subject not having the disease, such as a subject of the same age, gender, and/or weight), such that a determination that the level of the one or more substances in the sample from the subject having the disease is less than the level of the one or more substances in the reference sample indicates that the subject has the disease; or
  b) (i) determining a level of one or more substances selected from the group consisting of an mRNA molecule encoding a lipogenic protein, an adiponectin receptor, a lysine acetyltransferase, a histone acetyltransferase, a histone deacetylase, or a histone, a protein selected form the group consisting of a lipogenic protein, an adiponectin receptor, a lysine acetyltransferase, a histone acetyltransferase, a histone deacetylase, and a histone, or a methylated metabolite selected from the group consisting of 4-methyl-2-oxopentanoic acid and 3-methyl-2-oxobutyric acid in a sample from the subject; and
  (ii) comparing the level of the one or more substances to the level of the one or more substances in a reference sample (e.g., a sample isolated from a control subject not having the disease, such as a subject of the same age, gender, and/or weight), such that a determination that the level of the one or more substances in the sample from the subject having the disease is greater than the level of the one or more substances in the reference sample indicates that the subject has the disease.

In some embodiments, the method further includes determining whether the subject is likely to respond to treatment with a therapeutic agent for the disease, such that a determination that the level of the one or more substances listed in (a) in the sample from the subject having the disease is less than the level of the one or more substances in the reference sample indicates that the subject is likely to respond to the treatment, or such that a determination that the level of the one or more substances listed in (b) in the sample from the subject having the disease is greater than the level of the one or more substances in the reference sample indicates that the subject is likely to respond to the treatment.

In another aspect, the invention provides a method of determining whether a subject previously administered a therapeutic agent for the treatment of a disease would benefit from receiving one or more additional doses of the therapeutic agent, the method including:
  a) (i) determining a level of one or more substances selected from the group consisting of a an mRNA molecule encoding a cytokine or lipolytic protein, a protein selected from the group consisting of a cytokine and a lipolytic protein, an acetylated amino acid selected from the group consisting of N-acetylalanine, N-acetylaspartic acid, N-acetylserine, N-acetylthreonine, N-acetylhistidine, N-acetyl-3-methylhistidine, N-acetylvaline, and N-α-acetyllysine, and N-acetylmethionine, or a methylated metabolite selected from the group consisting of N-α-acetyl-3-methylhistidine, 3-methylglutaconic acid, 3-methylglutarylcarnitine, and N-ε-trimethyllysine in a sample from the subject; and (ii) comparing the level of the one or more substances to the level of the one or more substances in a reference sample (e.g., a prior sample that has been previously isolated from the subject), such that a determination that the level of the one or more substances in the sample from the subject is the same as or less than the level of the one or more substances in the reference sample indicates that the subject would benefit from additional doses of the therapeutic agent, or b) (i) determining a level of one or more substances selected from the group consisting of an mRNA molecule encoding a lipogenic protein, an adiponectin receptor, a lysine acetyltransferase, a histone acetyltransferase, a histone deacetylase, or a histone, a protein selected form the group consisting of a lipogenic protein, an adiponectin receptor, a lysine acetyltransferase, a histone acetyltransferase, a histone deacetylase, and a histone, or a methylated metabolite selected from the group consisting of 4-methyl-2-oxopentanoic acid and 3-methyl-2-oxobutyric acid in a sample from the subject; and (ii) comparing the level of the one or more substances to the level of the one or more substances in a reference sample (e.g., a prior sample that has been previously isolated from the subject), such that a determination that the level of the one or more substances in the sample from the subject is the same as or greater than the level of the one or more substances in the reference sample indicates that the subject would benefit from additional doses of the therapeutic agent.

In some cases, the method includes determining the level of a protein, such as a cytokine (e.g., IL-6, TNF, and IFNγ) or lipolytic protein (e.g., acyl co-enzyme A oxidase, carnitine palmitoyltransferase, lipase, and uncoupling protein), or an mRNA molecule encoding one of these proteins. In other embodiments, the method includes determining the level of an acetylated amino acid selected from the group consisting of N-acetylalanine, N-acetylaspartic acid, N-acetylserine, N-acetylthreonine, N-acetylhistidine, N-acetyl-3-methylhistidine, N-acetylvaline, and N-α-acetyllysine, and N-acetylmethionine. The method may include determining the level of a methylated metabolite selected from the group consisting of N-α-acetyl-3-methylhistidine, 3-methylglutaconic acid, 3-methylglutarylcarnitine, and N-ε-trimethyllysine. In some embodiments, the method includes determining the level of a protein, such as a lipogenic protein (e.g., acetyl co-enzyme A carboxylase α, acetyl co-enzyme A carboxylase β, fatty acid synthase, glyceraldehydes-6-phosphate dehydrogenase, stearoyl-CoA saturase, malic enzyme, or glucose-6-phosphate dehydrogenase), an adiponectin receptor (e.g., adiponectin receptor 1 or adiponectin receptor 2), a lysine acetyltransferase (e.g., KAT2A, KAT2B, KAT5, KAT6A, KAT6B, KAT7, and KAT8), a histone acetyltransferase, a histone deacetylase (e.g., HDAC1, HDAC2, HDAC3, HDAC4, HDAC5, HDAC6, HDAC7, HDAC8, HDAC9, HDAC10, HDAC11, HDAC1P1, HDAC1P2, SIRT1, SIRT2, SIRT3, SIRT4, SIRT5, SIRT6, or SIRT7), or a histone (e.g., a H2A, H2B, H3, or H4 family histone). In some cases, the method includes determining the level of a protein selected from the group consisting of a lipogenic protein, an adiponectin receptor, a lysine acetyltransferase, a histone acetyltransferase, a histone deacetylase, and a histone, or an mRNA molecule encoding one of these proteins. In some embodiments, the method includes determining the level of a methylated metabolite selected from the group consisting of 4-methyl-2-oxopentanoic acid and 3-methyl-2-oxobutyric acid.

In some cases, the level of the mRNA molecule is determined by performing an assay selected from the group consisting of reverse transcription PCR (RT-PCR) and a Northern blot. In other embodiments, the level of the protein is determined by performing an assay selected from the group consisting of an immunoblot and an enzyme-linked immunosorbant assay (ELISA). Additionally or alternatively, the level of the acetylated amino acid or the methylated metabolite is determined by nuclear magnetic resonance (NMR) spectroscopy.

In some embodiments of the above-described aspects of the invention, the prior sample has been isolated between about 24 hours and about 5 years before making the determination, such as about 1 month and about 1 year prior to making the determination. In some cases, the prior sample was isolated prior to the subject being administered the therapeutic agent.

In some embodiments of the above-described aspects of the invention, the disease is a condition associated with elevated levels of cholesterol, such as hypercholesterolemia, hyperlipidemia, coronary heart disease, peripheral arterial disease (PAD), peripheral vascular disease, hypertension, stroke, diabetes, metabolic syndrome, obesity, and insulin resistance. In other cases, the disease is an autoimmune disease, a neurological condition, an allergy, allograft rejection, graft-versus-host disease, asthma, macular degeneration, muscular atrophy, a disease related to miscarriage, atherosclerosis, bone loss, a musculoskeletal disease, or obesity, e.g., as described herein.

In some embodiments of the above-described methods of the invention, the therapeutic agent is BCG. The methods of the invention may further include administering an effective amount of BCG to the subject. The BCG may be administered, e.g., in a unit dosage form including between about $5 \times 10^5$ and about $1 \times 10^7$ colony forming units (cfu) per 0.1 milligrams of BCG, such as between about $1 \times 10^6$ and about $6 \times 10^6$ cfu per 0.1 milligrams of BCG, preferably between about $1.8 \times 10^6$ and about $3.9 \times 10^6$ cfu per 0.1 milligrams of BCG. The BCG may be administered to the subject about once every 1-20 years (e.g., between about once every 1-10 years, such as about once every 5 years). The patient may be administered a total of about 1-20 doses of the BCG (e.g., a total of about 2-5 doses of the BCG, such as a total of 2 doses of BCG).

In other embodiments, the therapeutic agent is a hypolipidemic agent selected from the group consisting of a HMG-CoA reductase inhibitor, niacin, a fibric acid derivative, a cholesterol absorption inhibitor, and a lipolytic agent, e.g., as described herein.

In some embodiments of the invention, an additional therapeutic agent is administered to the subject, such as TNFα, a TNFR2 agonist, or an immunotherapy agent (e.g., an anti-CTLA-4 agent, an anti-PD-1 agent, an anti-PD-L1 agent, an anti-PD-L2 agent, a TNF-α cross-linking agent, a TRAIL cross-linking agent, a CD27 agent, a CD30 agent, a CD40 agent, a 4-1BB agent, a GITR agent, an OX40 agent, a TRAILR1 agent, a TRAILR2 agent, or a TWEAKR agent).

In embodiments of any of the above-described aspects of the invention, the subject is a mammal (e.g., a human).

In yet another aspect, the invention provides a kit including BCG and a package insert instructing a user of the kit to treat a subject according to any of the methods of the invention described herein. The kit may further include an additional therapeutic agent, e.g., as described above.

An additional aspect of the invention relates to a kit including an agent that can be used to determine the methylation state of one or more cytosine residues, such as a bisulfite salt, as well as a package insert instructing a user of the kit to perform a method of the invention (e.g., to determine the quantity of methylated cytosine residues in a gene of interest according to a method of the invention).

In still another aspect, the invention provides a kit including an agent that can be used to detect one or more mRNA molecules (e.g., a complementary polynucleotide capable of hybridizing with the mRNA molecule of interest, e.g., by Watson-Crick base pairing), in addition to a package insert instructing a user of the kit to perform a method of the invention (e.g., to measure a level of one or more mRNA molecules according to a method of the invention).

The invention additionally provides a kit that includes a package insert instructing a user of the kit to perform a method of diagnosing a subject or assessing a subject for the benefit of administering one or more additional doses of a therapeutic agent (e.g., BCG) as described herein.

In another aspect, the invention features a method of reducing the level of glucose (e.g., by 1% or more, and/or by at least 10 mg/dL, such as by between 10 mg/dL and 100 mg/dL or more, such as by 10 mg/dL, 20 mg/dL, 30 mg/dL, 40 mg/dL, 50 mg/dL, 60 mg/dL, 70 mg/dL, 80 mg/dL, 90 mg/dL, 100 mg/dL, or more) in the blood of a subject (e.g., a mammalian subject, such as a human subject) in need thereof including administering BCG to the subject.

The subject may be a hyperglycemic subject, such as a subject having (i) a chronically, acutely, or persistently elevated blood glucose level, such as a chronic, acute, or persistent blood glucose level of over 100 mg/dL (e.g., a subject having a chronic, acute, or persistent blood glucose level of over 126 mg/dL, such as a subject having a chronic, acute, or persistent blood glucose level of 130 mg/dL, 140 mg/dL, 150 mg/dL, 160 mg/dL, 170 mg/dL, 180 mg/dL, 190 mg/dL, 200 mg/dL, 210 mg/dL, 220 mg/dL, 230 mg/dL, 240 mg/dL, 250 mg/dL, or more), (ii) a subject suffering from a disease associated with hyperglycemia, such as type 2 diabetes, noninsulin-dependent diabetes mellitus (NIDDM), nonalcoholic steatohepatitis (NASH), metabolic syndrome, cystic fibrosis, drug induced hyperglycemia, insulin resistance syndromes, diseases caused by genetic mutations in the pancreas, cancer, infection, Leprechaunism, Rabson Mandenhall syndrome, lipoatrophic diabetes, pancreatitis, trauma, hemochromatoisis, fibrocalculous pancreatopathy, acromegaly, Cushings syndrome, glucagonoma, pheochromocytoma, hyperthyroism, somatostatinoma, aldosteroma, infections associated with beta cell destruction, Rubella, coxsachie virus B, mumps, cytomegatolovirus infection, adenovirus infection, a genetic syndrome, stiff person syndrome, anti-insulin receptor abnormalities, liver disease, and renal failure, and/or (iii) a subject exhibiting an increase in blood glucose concentration relative to a previous measurement of blood glucose in the blood of the subject, such as an increase of from about 10 mg/dL to about 200 mg/dL over the course of from about 1 week to about 5 years (e.g., an increase in blood glucose level of from about 10 mg/dL, 20 mg/dL, 30 mg/dL, 40 mg/dL, 50 mg/dL, 60 mg/dL, 70 mg/dL, 80 mg/dL, 90 mg/dL, 100 mg/dL, 110 mg/dL, 120 mg/dL, 130 mg/dL, 140 mg/dL, 150 mg/dL, 160 mg/dL, 170 mg/dL, 180 mg/dL, 190 mg/dL, 200 mg/dL, or more, over the course of 1 week, 1 month, 6 months, 1 year, 2 years, 3 years, 4 years, 5 years, or longer).

In some embodiments, the administration of BCG lowers the level of glucose in the blood of the subject by about 0.1%, 0.2%, 0.3%, 0.4%, 0.5%, 0.6%, 0.7%, 0.8%, 0.9%, 1%, 2%, 3%, 4%, 5%, or more (e.g., by about 0.1%, 0.5%, 1%, 2%, 3%, 4%, 5%, 6%, 7%, 8%, 9%, 10%, 20%, 30%, 40%, 50%, or more). In some embodiments, the administration of BCG lowers the level of glucose in the blood of the subject by from about 10% to about 40% (e.g., by about 10%, 20%, 30%, or 40%). The administration may lower the level of glucose in the blood of the subject within about 1 week to about 8 years (e.g., within about 1 week, 2 weeks, 3 weeks, 4 weeks, 6 months, 1 year, 2 years, 3 years, 4 years, 5 years, 6 years, 7 years, 8 years, or more, such as from about 1 week to about 8 years, from about 6 months to about 5 years, or from about 1 year to about 3 years) after being treated with the BCG. In some embodiments, the blood glucose level of the subject is stabilized following administration of BCG, for instance, such that it does not increase (e.g., by more than 15%, such as by not more than about 15%, 14%, 13%, 12%, 11%, 10%, 9%, 8%, 7%, 6%, 5%, or less) for a period of from about 1 week to about 8 years following said administration (e.g., 1 week, 2 weeks, 3 weeks, 4 weeks, 6 months, 1 year, 2 years, 3 years, 4 years, 5 years, 6 years, 7 years, 8 years, or more). In some embodiments, the invention features methods of stabilizing the level of glucose in the blood of a subject, for instance, by administration of BCG as described herein. In some embodiments, the invention features methods of preventing an increase in the level of glucose in the blood of a subject, for instance, by administration of BCG as described herein.

In some embodiments, the administration of BCG lowers the level of glycated hemoglobin in the blood of the subject, for instance, by about 5% or more (e.g., by about 5%, 6%, 7%, 8%, 9%, 10%, 20%, 30%, 40%, 50%, or more). In some embodiments, the administration of BCG lowers the level of glycated hemoglobin in the blood of the subject by about 15% or more (e.g., by about 20%, 30%, 40%, 50%, or more). The administration of BCG may lower the level of glycated hemoglobin in the blood of the subject within about 2 weeks to about 8 years after being treated with the BCG (e.g., within about 2 weeks, 3 weeks, 4 weeks, 6 months, 1 year, 2 years, 3 years, 4 years, 5 years, 6 years, 7 years, 8 years, or more).

Administration of BCG can cause an increase in the rate of glycolysis in the subject, for instance, by increasing the expression of one or more glycolytic enzymes in the subject. Administration of BCG can cause an increase in flux through the pentose phosphate shunt in the subject. BCG administration can cause a decrease in the rate of oxidative phosphorylation (e.g., of adenosine diphosphate) in the subject.

In some embodiments, administration of BCG increases the level of lactate and/or 1,5-anhydroglucitol in the blood of the subject. In some embodiments, administration of BCG lowers the level of α-ketobutyrate and/or 2-hydroxybutyrate in the blood of the subject.

In some embodiments, administration of BCG increases the expression of hypoxia-inducible factor 1-α (HIF1-α) in the blood of the subject, for instance, in a lymphocyte (e.g., a peripheral blood lymphocyte) or in a monocyte in the subject. Expression of HIF1-α may be assessed, for example, by monitoring HIF1-α mRNA or protein expression in a sample (e.g., a blood sample) isolated from the subject following BCG administration. In some embodiments, administration of BCG increases expression of HIF-1α mRNA by from about 3-fold to about 6-fold.

Administration of BCG to the subject may increase expression of a glucose transporter in the blood of the subject (e.g., relative to a measurement of the glucose transporter in the blood of the subject prior to administration to BCG and/or relative to a measurement of the glucose transporter in the blood of a healthy subject not suffering from hyperglycemia or a disease associated therewith, such as a healthy subject of the same age and/or gender as the subject), such as solute carrier family 2 member 6 (SLC2A6), for instance, by 1%, 5%, 10%, 15%, 20%, 25%, 30%, 35%, 40%, 45%, 50%, or more. Expression of the glucose transporter may be assessed, for example, by monitoring glucose transporter mRNA or protein expression in a sample isolated from the subject following BCG administration. In some embodiments, administration of BCG increases the expression of a glycolytic enzyme in the blood of the subject, such as hexokinase 2 (HK2), glucose-6-phosphate isomerase (G6PI), triosephosphate isomerase 1 (TPI1), galactokinase 1 (GALK1), and galactose mutarotase (GALM). Expression of the glycolytic enzyme may be assessed, for example, by monitoring glucose transporter mRNA or protein expression in a sample (e.g., a blood sample) isolated from the subject following BCG administration.

In some embodiments, administration of BCG to the subject reduces the expression of an enzyme that promotes flux through the Krebs cycle in the blood of the subject (e.g., relative to a measurement of the enzyme in the blood of the subject prior to administration to BCG and/or relative to a measurement of the enzyme in the blood of a healthy subject not suffering from hyperglycemia or a disease associated therewith, such as a healthy subject of the same age and/or gender as the subject), such as adenosine triphosphate citrate lyase (ACLY), aconitase 2 (ACO2), citrate synthase (CS), dihydrolipoamide dehydrogenase (DLD), oxoglutarate dehydrogenase (OGDH), succinate dehydrogenase iron-sulfur complex subunit κ (SDHB), and succinate-CoA ligase subunit α (SUCLG1), for instance, by 1%, 5%, 10%, 15%, 20%, 25%, 30%, 35%, 40%, 45%, 50%, or more. Expression of the enzyme that promotes flux through the Krebs cycle can be assessed, for instance, by monitoring enzyme mRNA or protein expression in a sample isolated from the subject following BCG administration.

The administration of BCG may lower the level of one or more of the above-referenced substances in the blood of the subject within about 2 weeks to about 8 years after being treated with the BCG (e.g., within about 2 weeks, 3 weeks, 4 weeks, 6 months, 1 year, 2 years, 3 years, 4 years, 5 years, 6 years, 7 years, 8 years, or more).

In some embodiments, the subject has a blood glucose level of about 100 mg/dL or greater prior to administration of the BCG (e.g., 100 mg/dL, 110 mg/dL, 120 mg/dL, 130 mg/dL, 140 mg/dL, 150 mg/dL, 160 mg/dL, 170 mg/dL, 180 mg/dL, 190 mg/dL, 200 mg/dL, 210 mg/dL, 220 mg/dL, 230 mg/dL, 240 mg/dL, 250 mg/dL, 260 mg/dL, 270 mg/dL, 280 mg/dL, 290 mg/dL, 300 mg/dL or more, such as a blood glucose level of about 126 mg/dL or greater (e.g., 130 mg/dL, 140 mg/dL, 150 mg/dL, 160 mg/dL, 170 mg/dL, 180 mg/dL, 190 mg/dL, 200 mg/dL, 210 mg/dL, 220 mg/dL, 230 mg/dL, 240 mg/dL, 250 mg/dL, 260 mg/dL, 270 mg/dL, 280 mg/dL, 290 mg/dL, 300 mg/dL or more). In some embodiments, the subject has a blood glucose level of about 200 mg/dL or more prior to administration of the BCG. The subject may have a blood glucose level that is higher than a blood glucose level that has previously been observed for the subject, such as prior to administration of the BCG. In some embodiments, the subject has previously been observed as having a blood glucose level of less than about 200 mg/dL, such as less than about 126 mg/dL, such as a blood glucose level of about 100 mg/dL or less, for instance, prior to administration of the BCG.

In some embodiments, the subject is suffering from a disease associated with an elevated blood glucose level, such as type 2 diabetes, noninsulin-dependent diabetes mellitus (NIDDM), nonalcoholic steatohepatitis (NASH), metabolic syndrome, cystic fibrosis, drug induced hyperglycemia, insulin resistance syndromes, diseases caused by genetic mutations in the pancreas, cancer, infection, Leprechaunism, Rabson Mandenhall syndrome, lipoatrophic diabetes, pancreatitis, trauma, hemochromatoisis, fibrocalculous pancreatopathy, acromegaly, Cushings syndrome, glucagonoma, pheochromocytoma, hyperthyroism, somatostatinoma, aldosteroma, infections associated with beta cell destruction, Rubella, coxsachie virus B, mumps, cytomegatolovirus infection, adenovirus infection, a genetic syndrome, stiff person syndrome, anti-insulin receptor abnormalities, liver disease, and renal failure. In some embodiments, the drug induced hyperglycemia is induced by one or more agents selected from the group consisting of steroids, cortisol, thiazides, diazocide, calcineurin inhibitors, oral contraceptives, beta adrenergic agonists, nicotinic acid, pentamidine, alpha interferon, anti-psychotic agents, anti-retroviral agents, and rodenticides (e.g., pyrinuron). In some embodiments, the cancer is pancreatic cancer. In some embodiments, the genetic syndrome is selected from the group consisting of Down's syndrome, Klinefelter's syndrome, Turner syndrome, Woldfram syndrome, and Friendreich ataxia. In some embodiments, the subject has undergone a pancreatectomy. The subject may exhibit one or more mutations in a mitochondrial gene, such as hepatic nuclear factor 1 (MODY3), glucokinase (MODY2), and hepatocyte nuclear factor 4-α (MODY1).

In some embodiments, BCG is administered to the subject in an amount sufficient to alleviate or reduce a symptom associated with the disease, such as polyphagia, polydipsia, polyuria, blurred vision, fatigue, cardiac arrhythmia, stupor, dry mouth, and poor wound healing.

In some embodiments, the BCG is administered in a unit dosage form containing between about $5 \times 10^5$ and about $1 \times 10^7$ cfu per 0.1 milligrams of BCG, such as a unit dosage form containing between about $1 \times 10^6$ and about $6 \times 10^6$ cfu per 0.1 milligrams of BCG (e.g., a unit dosage form containing between about $1.8 \times 10^6$ and about $3.9 \times 10^6$ cfu per 0.1 milligrams of BCG, such as $1.8 \times 10^6$ cfu per 0.1 miligrams of BCG, $1.9 \times 10^6$ cfu per 0.1 miligrams of BCG, $2.0 \times 10^6$ cfu per 0.1 miligrams of BCG, $2.1 \times 10^6$ cfu per 0.1 miligrams of BCG, $2.2 \times 10^6$ cfu per 0.1 miligrams of BCG, $2.3 \times 10^6$ cfu per 0.1 miligrams of BCG, $2.4 \times 10^6$ cfu per 0.1 miligrams of BCG, $2.5 \times 10^6$ cfu per 0.1 miligrams of BCG, $2.6 \times 10^6$ cfu per 0.1 miligrams of BCG, $2.7 \times 10^6$ cfu per 0.1 miligrams of BCG, $2.8 \times 10^6$ cfu per 0.1 miligrams of BCG, $2.9 \times 10^6$ cfu per 0.1 miligrams of BCG, $3.0 \times 10^6$ cfu per 0.1 miligrams of BCG, $3.1 \times 10^6$ cfu per 0.1 miligrams of BCG, $3.2 \times 10^6$ cfu per 0.1 miligrams of BCG, $3.3 \times 10^6$ cfu per 0.1 miligrams of BCG, $3.4 \times 10^6$ cfu per 0.1 miligrams of BCG, $3.5 \times 10^6$ cfu per 0.1 miligrams of BCG, $3.6 \times 10^6$ cfu per 0.1 miligrams of BCG, $3.7 \times 10^6$ cfu per 0.1 miligrams of BCG, $3.8 \times 10^6$ cfu per 0.1 miligrams of BCG, or $3.9 \times 10^6$ cfu per 0.1 miligrams of BCG).

In some embodiments, BCG is administered to the subject by a route of administration described herein or known in the art. For instance, BCG may be administered to the subject intradermally, subcutaneously, or percutaneously (i.e., by an intradermal or subcutaneous route). In some embodiments, BCG is not administered to the subject intravenously.

In some embodiments, the BCG is administered to the subject about once every 1-20 years, such as about once every 1-10 years (e.g., about once every 5 years). In some embodiments, the subject is administered a total of 1-20 doses of BCG, such as a total of 2-5 doses of BCG (e.g., a total of 2 doses of BCG). The subject may be administered a first dose of BCG followed by a second dose of BCG from about 2 weeks to about 8 weeks after administration of the first dose. For instance, the subject may be administered a first dose of BCG followed by a second dose of BCG about 4 weeks after administration of the first dose.

In some embodiments, subsequent doses of BCG (e.g., a second, third, fourth, or fifth, or greater) dose of BCG can be administered to the subject, for instance, if the blood glucose concentration in the subject has increased by 10% or more (e.g., by about 10%, 15%, 20%, 25%, 30%, 35%, 40%, 45%, 50%, or more) or by 20 mg/dL or more (e.g., by about 20 mg/dL, 30 mg/dL, 40 mg/dL, 50 mg/dL, 60 mg/dL, 70 mg/dL, 80 mg/dL, 90 mg/dL, 100 mg/dL, or more) over a period of from about 6 months to about 5 years (e.g., 6 months, 1 year, 2 years, 3 years, 4 years, 5 years, or more).

Additionally or alternatively, BCG administration can increase the expression of nuclear receptor subfamily 1 group H member 3 (NR1H3) in the subject (e.g., relative to a measurement of NR1H3 in the blood of the subject prior to administration to BCG and/or relative to a measurement of NR1H3 in the blood of a healthy subject not suffering from hyperglycemia or a disease associated therewith, such as a healthy subject of the same age and/or gender as the subject), for instance, by 1%, 5%, 10%, 15%, 20%, 25%, 30%, 35%, 40%, 45%, 50%, or more. NR1H3 expression can be assessed, for instance, by monitoring NR1H3 mRNA or protein expression. BCG administration can increase the expression of cholesterol-suppressing genes, such as adenosine triphosphate binding cassette subfamily A member 1 (ABCA1), adenosine triphosphate binding cassette subfamily G (ABCG), apolipoprotein E(APOE), Fas cell surface death receptor (FAS), and stearoyl-CoA desaturase (SCD1). Additionally or alternatively, BCG administration can reduce the expression of glucose-elevating genes, such as fructose-bisphosphatase 1 (FBP1), glucose-6-phosphate dehydrogenase (G6PD), and muscle pyruvate kinase (PKM).

In another aspect, the invention features a method of diagnosing a subject as having hyperglycemia or a disease associated therewith, the method comprising:
 a) i) determining a level of one or more substances selected from the group consisting of glucose, cholesterol, LDL, a triglyceride, glycated hemoglobin, an mRNA molecule encoding a protein selected from the group consisting of FBP1, G6PD, and PKM, a protein selected from the group consisting of FBP1, G6PD, and PKM, an mRNA molecule encoding an enzyme that promotes flux through the Krebs cycle, an enzyme that promotes flux through the Krebs cycle, α-ketobutyrate, and 2-hydroxybutyrate in a sample from the subject; and
 (ii) comparing the level of the one or more substances to the level of the one or more substances in a reference sample, wherein a determination that the level of the one or more substances in the sample from the subject is greater than the level of the one or more substances in the reference sample indicates that the subject has hyperglycemia or disease associated with hyperglycemia; or
 b) (i) determining a level of one or more substances selected from the group consisting of an mRNA molecule encoding a glycolytic enzyme, a glycolytic enzyme, an mRNA molecule encoding a glucose transporter, a glucose transporter, an mRNA molecule encoding HIF1-α, HIF1-α, an mRNA molecule encoding NR1H3, NR1H3, lactate, and 1,5-anhydroglucitol in a sample from the subject; and
 (ii) comparing the level of the one or more substances to the level of the one or more substances in a reference sample, wherein a determination that the level of the one or more substances in the sample from the subject is less than the level of the one or more substances in the reference sample indicates that the subject has hyperglycemia or disease associated with hyperglycemia.

In some embodiments, the method further comprising determining whether the subject is likely to respond to treatment with a therapeutic agent for the disease (e.g., BCG), wherein a determination that the level of the one or more substances listed in (a) in the sample from the subject having the hyperglycemia or disease associated therewith is greater than the level of the one or more substances in the reference sample indicates that the subject is likely to respond to the treatment, or wherein a determination that the level of the one or more substances listed in (b) in the sample from the subject having the disease is less than the level of the one or more substances in the reference sample indicates that the subject is likely to respond to the treatment.

In some embodiments, the reference sample is a sample isolated from a control subject not having the disease. In some embodiments, the control subject is a subject of the same age and/or gender of the subject having the disease.

In some embodiments, the reference sample is a prior sample that has been previously isolated from the subject. In some embodiments, the prior sample was isolated between about 24 hours and about 5 years before making the determination, such as between about 1 month and about 1 year prior to making the determination. In some embodiments, the prior sample was isolated prior to the subject being administered the therapeutic agent.

In another aspect, the invention features a method of determining whether a subject previously administered a therapeutic agent for the treatment of a disease would benefit from receiving one or more additional doses of the therapeutic agent, the method comprising:
 a) (i) determining a level of one or more substances selected from the group consisting of glucose, cholesterol, LDL, a triglyceride, glycated hemoglobin, an mRNA molecule encoding a protein selected from the group consisting of FBP1, G6PD, and PKM, a protein selected from the group consisting of FBP1, G6PD, and PKM, an mRNA molecule encoding an enzyme that promotes flux through the Krebs cycle, an enzyme that promotes flux through the Krebs cycle, α-ketobutyrate, and 2-hydroxybutyrate in a sample from the subject; and
 (ii) comparing the level of the one or more substances to the level of the one or more substances in a reference sample, wherein a determination that the level of the one or more substances in the sample from the subject is the same as or greater than the level of the one or more substances in the reference sample indicates that the subject would benefit from one or more additional doses of the therapeutic agent, or
 b) (i) determining a level of one or more substances selected from the group consisting of an mRNA molecule encoding a glycolytic enzyme, a glycolytic enzyme, an mRNA molecule encoding a glucose transporter, a glucose transporter, an mRNA molecule encoding HIF1-α, HIF1-α, an mRNA molecule encoding NR1H3, NR1H3, lactate, and 1,5-anhydroglucitol in a sample from the subject; and (ii) comparing the level of the one or more substances to the level of the one or more substances in a reference sample, wherein a determination that the level of the one or more substances in the sample from the subject is the same as or less than the level of the one or more substances in the reference sample indicates that the subject would benefit from one or more additional doses of the therapeutic agent.

In some embodiments, the reference sample is a sample isolated from a control subject not having the disease. In some embodiments, the control subject is a subject of the same age and/or gender of the subject having the disease.

In some embodiments, the reference sample is a prior sample that has been previously isolated from the subject. In some embodiments, the prior sample was isolated between about 24 hours and about 5 years before making the determination, such as between about 1 month and about 1 year prior to making the determination. In some embodiments, the prior sample was isolated prior to the subject being administered the therapeutic agent.

In some embodiments, the enzyme that promotes flux through the Krebs cycle is selected from the group consisting of ACLY, ACO2, CS, DLD, OGDH, SDHB, and SUCLG1. In some embodiments, the glycolytic enzyme is selected from the group consisting of HK2, G6PI, TPI1, GALK1, and GALM. In some embodiments, the glucose transporter is SLC2A6.

In some embodiments, the level of the mRNA molecule is determined by performing an assay selected from the group consisting of reverse transcription PCR (RT-PCR) and a Northern blot. In some embodiments, the level of the enzyme that promotes flux through the Krebs cycle, glycolytic enzyme, glucose transporter, HIF-1α, NR1H3, FBP1, G6PD, or PKM is determined by performing an assay selected from the group consisting of an immunoblot and an enzyme-linked immunosorbant assay (ELISA). In some embodiments, the level of the α-ketobutyrate, 2-hydroxybutyrate, lactate, or 1,5-anhydroglucitol is determined by nuclear magnetic resonance (NMR) spectroscopy.

In some embodiments, the disease associated with hyperglycemia is selected from the group consisting of type 2 diabetes, noninsulin-dependent diabetes mellitus (NIDDM), nonalcoholic steatohepatitis (NASH), metabolic syndrome, cystic fibrosis, drug induced hyperglycemia, insulin resistance syndromes, diseases caused by genetic mutations in the pancreas, cancer, infection, Leprechaunism, Rabson Mandenhall syndrome, lipoatrophic diabetes, pancreatitis, trauma, hemochromatoisis, fibrocalculous pancreatopathy, acromegaly, Cushings syndrome, glucagonoma, pheochromocytoma, hyperthyroism, somatostatinoma, aldosteroma, infections associated with beta cell destruction, Rubella, coxsachie virus B, mumps, cytomegatolovirus infection, adenovirus infection, a genetic syndrome, stiff person syndrome, anti-insulin receptor abnormalities, liver disease, and renal failure.

In some embodiments, the method comprising administering the therapeutic agent to the subject identified as a subject that would benefit from one or more additional doses of the therapeutic agent (e.g., BCG). In some embodiments, the method comprises administering BCG to the subject identified as having hyperglycemia or a disease associated therewith. In some embodiments, BCG is the only therapeutic agent administered to the subject (e.g., the sole therapeutic agent).

In some embodiments, the subject is not administered an agent that promotes the expression of IL-2. In some embodiments, the subject is not administered lymphotoxin or Lentinan. In some embodiments, the subject is not administered TNF-α, a TNF-α agonist antibody, or an agent that promotes the expression of TNF-α other than BCG.

In another embodiment of the methods of treating and/or diagnosing hyperglycemia or conditions related to hyperglycemia, the patient to be treated does not have type 1 diabetes.

In another aspect, the invention features a method of inducing an increase in the rate of aerobic glycolysis in a mammalian subject (e.g., a human), the method comprising administering to the subject BCG. The rate of aerobic glycolysis in the subject may be measured, for instance, by measuring the expression of one or more glycolytic enzymes, such as an early glycolytic enzyme described herein, or by measuring the level of a product of glycolysis or an associated fermentation pathway (e.g., pyruvate or lactate) in the blood of the subject. In some embodiments, the rate of aerobic glycolysis is increased relative to a measurement of aerobic glycolysis in the subject prior to administration of the BCG. The rate of aerobic glycolysis may be increased, for instance, by about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, or more, e.g., as assessed by measuring the increase in the expression of one or more early glycolytic enzymes or by measuring the increase in the level of one or more products of glycolysis or an associated fermentation pathway, such as pyruvate or lactate, or by measuring the increase in the level of HIF-1α or NR1H3 in the subject. In some embodiments, the administering reduces the rate of oxidative phosphorylation of adenosine diphosphate in the subject relative to a measurement of oxidative phosphorylation of adenosine diphosphate in the subject prior to administration of the BCG. The rate of oxidative phosphorylation may be decreased, for instance, by about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, or more, e.g., as assessed by measuring the decrease in the expression of one or more early enzymes that promote flux through the Krebs cycle or by measuring the change in the level of one or more metabolites involved in the Krebs cycle, such as a Krebs cycle metabolite described herein or known in the art.

In some embodiments, the administering reduces the level of one or more substances selected from the group consisting of glucose, cholesterol, LDL, a triglyceride, glycated hemoglobin, an mRNA molecule encoding a protein selected from the group consisting of FBP1, G6PD, and PKM, a protein selected from the group consisting of FBP1, G6PD, and PKM, an mRNA molecule encoding an enzyme that promotes flux through the Krebs cycle, an enzyme that promotes flux through the Krebs cycle, α-ketobutyrate, and 2-hydroxybutyrate in the subject relative to a measure of the substance in the subject prior to administration of the BCG.

In some embodiments, the administering increases the level of one or more substances selected from the group consisting of an mRNA molecule encoding a glycolytic enzyme, a glycolytic enzyme, an mRNA molecule encoding a glucose transporter, a glucose transporter, an mRNA molecule encoding HIF1-α, HIF1-α, an mRNA molecule encoding NR1H3, NR1H3, lactate, and 1,5-anhydroglucitol in the subject relative to a measure of the substance in the subject prior to administration of the BCG.

In some embodiments, the enzyme that promotes flux through the Krebs cycle is selected from the group consisting of ACLY, ACO2, CS, DLD, OGDH, SDHB, and SUCLG1.

In some embodiments, the glycolytic enzyme is selected from the group consisting of HK2, G6PI, TPI1, GALK1, and GALM.

In some embodiments, the glucose transporter is SLC2A6.

Definitions

As used herein, the term "about" refers to a value that is within 10% above or below the value being described.

As used herein, the term "agonist" refers to a compound capable of promoting the activation of a receptor so as to potentiate a downstream signal transduction pathway. For instance, the terms "tumor necrosis factor receptor 2 agonist" and "TNFR2 agonist" as used herein include compounds that specifically bind TNFR2 in such a way that induces the activation of this receptor which, in turn, promotes TRAF2/3- and/or NFκB-mediated cell proliferation. Agonists of TNFR2 include endogenous ligands that activate the receptor, such as TNFα, which is capable of binding TNFR2 and inducing a conformational change that propagates signal transduction events that lead to cell proliferation.

As used herein, "BCG" refers to Bacillus Calmette-Guerin, which is a preparation of *Mycobacterium bovis*, an attenuated strain of *Mycobacterium turberculosis* that is not virulent in humans. Examples of BCG include a variety of substrains that have been developed by genetic manipulation, including, e.g., the Pasteur, Phipps, Frappier, Mexico, Birkhaug, Sweden, Moreau, Japan-Tokyo, Copenhagen, TICE, Sanofi, Connaught, RIVM, Evans, MMC, and Glaxo substrains of BCG, among others, as well as genetic variants of these substrains. BCG substrains, as well as the genetic differences between these substrains, are known in the art and are described, e.g., in Castillo-Rodal, et al., Infect Immun. 74(3):1718-1724 (2006); as well as in Zhang, et al., Tubercle and Lung Disease 76(1):43-50 (1995); the disclosures of each of which are incorporated herein by reference.

As used herein, a "colony forming unit" (cfu) refers to at least one cell that is capable of giving rise to a population of genetically identical cells by mitotic cell proliferation. Colony forming units include a single cell, but may also be an aggregation of cells, such as a colony.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the terms "elevated blood glucose" and "hyperglycemic" are used interchangeably to characterize a subject having abnormally high blood glucose concentrations and/or that may benefit from therapy described herein. Hyperglycemic subjects include those that exhibit one or more, or all three, of the following characteristics: (i) a chronic, acute, or persistent blood glucose level of over 100 mg/dL (e.g., a chronic, acute, or persistent blood glucose level of over 126 mg/dL, such as a chronic, acute, or persistent blood glucose level of 130 mg/dL, 140 mg/dL, 150 mg/dL, 160 mg/dL, 170 mg/dL, 180 mg/dL, 190 mg/dL, 200 mg/dL, 210 mg/dL, 220 mg/dL, 230 mg/dL, 240 mg/dL, 250 mg/dL, or more), (ii) presenting with a disease associated with hyperglycemia, such as type 2 diabetes, noninsulin-dependent diabetes mellitus (NIDDM), nonalcoholic steatohepatitis (NASH), metabolic syndrome, cystic fibrosis, drug induced hyperglycemia, insulin resistance syndromes, diseases caused by genetic mutations in the pancreas, cancer, infection, Leprechaunism, Rabson Mandenhall syndrome, lipoatrophic diabetes, pancreatitis, trauma, hemochromatoisis, fibrocalculous pancreatopathy, acromegaly, Cushings syndrome, glucagonoma, pheochromocytoma, hyperthyroism, somatostatinoma, aldosteroma, infections associated with beta cell destruction, Rubella, coxsachie virus B, mumps, cytomegatolovirus infection, adenovirus infection, a genetic syndrome, stiff person syndrome, anti-insulin receptor abnormalities, liver disease, and renal failure, and/or (iii) an increase in blood glucose concentration relative to a previous measurement of blood glucose in the blood of the subject, such as an increase of from about 10 mg/dL to about 200 mg/dL over the course of from about 1 week to about 5 years (e.g., an increase in blood glucose level of from about 10 mg/dL, 20 mg/dL, 30 mg/dL, 40 mg/dL, 50 mg/dL, 60 mg/dL, 70 mg/dL, 80 mg/dL, 90 mg/dL, 100 mg/dL, 110 mg/dL, 120 mg/dL, 130 mg/dL, 140 mg/dL, 150 mg/dL, 160 mg/dL, 170 mg/dL, 180 mg/dL, 190 mg/dL, 200 mg/dL, or more, over the course of 1 week, 1 month, 6 months, 1 year, 2 years, 3 years, 4 years, 5 years, or longer).

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted therefrom.

As used herein, the term "fusion protein" refers to a protein that is joined via a covalent bond to another molecule. A fusion protein can be chemically synthesized by, e.g., an amide-bond forming reaction between the N-terminus of one protein to the C-terminus of another protein. Alternatively, a fusion protein containing one protein covalently bound to another protein can be expressed recombinantly in a cell (e.g., a eukaryotic cell or prokaryotic cell) by expression of a polynucleotide encoding the fusion protein, for example, from a vector or the genome of the cell. A fusion protein may contain one protein that is covalently bound to a linker, which in turn is covalently bound to another molecule. Examples of linkers that can be used for the formation of a fusion protein include peptide-containing linkers, such as those that contain naturally occurring or non-naturally occurring amino acids. In certain cases, it may be desirable to include D-amino acids in the linker, as these residues are not present in naturally-occurring proteins and are thus more resistant to degradation by endogenous proteases. Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage (Leriche et al., Bioorg. Med. Chem., 20:571-582, 2012).

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, the term "operatively linked" in the context of a polynucleotide fragment is intended to mean that the two polynucleotide fragments are joined such that the amino acid sequences encoded by the two polynucleotide fragments remain in-frame.

As used herein, the term "regulatory sequence" includes promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990); incorporated herein by reference.

As used herein, the term "reference sample" refers to a measurement of the quantity of one or more substances, such as cholesterol, glucose, methylated or demethylated cytosine residues in one or more DNA molecules, or the quantity of one or more mRNA molecules, proteins, acetylated amino acids, and/or methylated metabolites, that can be compared with a measurement of the same substance in a sample isolated from a subject, e.g., in order to assess the likelihood of the subject to respond to a particular therapy (such as BCG therapy) and/or to determine if the subject would benefit from one or more subsequent doses of a therapeutic agent after the subject has already received at least one initial dose of a medicament to treat a disease or condition in the subject. In the context of a method of determining whether a disease that the subject has been diagnosed as having is likely to be treated with a certain therapeutic regimen (e.g., administration of BCG), the reference sample may be a sample isolated from a healthy subject not suffering from the disease being assessed, optionally of the same age, sex, and/or weight as the subject suffering from the disease. The reference sample may alternatively be an accepted measurement of one or more substances (e.g., the quantity of cholesterol, glucose, methylated or demethylated cytosine residues in a DNA molecule, and/or the quantity of one or more mRNA molecules, proteins, acetylated amino acids, and/or methylated metabolites) that is indicative of a normal physiological state. In the context of a method of determining whether a patient suffering from a certain disease or condition and that has already been administered at least one therapeutic agent (BCG), e.g., for the treatment of the disease, would benefit from one or more additional doses of a medicament, the reference sample may be a sample previously isolated from the subject, such as a sample that was isolated from the subject prior to earlier administration of a therapeutic agent. The reference sample may alternatively be a measurement of one or more substances (e.g., the quantity of cholesterol, glucose, methylated or demethylated cytosine residues in a DNA molecule, and/or the quantity of one or more mRNA molecules, proteins, acetylated amino acids, and/or methylated metabolites) that is indicative of an abnormal physiological state, such as a physiological state that is characteristic of a particular disease.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject. Preferably, the sample is blood, a blood component (e.g., serum or plasma), or urine.

As used herein, the phrase "specifically binds" refers to a binding reaction which is determinative of the presence of a receptor in a heterogeneous population of proteins and other biological molecules that is recognized, e.g., by a ligand with particularity. A ligand that specifically binds to a receptor will bind to the receptor with a $K_D$ of less than 100 nM. For example, a ligand that specifically binds to a receptor will bind to the receptor with a $K_D$ of up to 100 nM (e.g., between 1 pM and 100 nM). A ligand that does not exhibit specific binding to a receptor or a domain thereof will exhibit a $K_D$ of greater than 100 nM (e.g., greater than 500 nm, 1 µM, 100 µM, 500 µM, or 1 mM) for that particular receptor or domain thereof. A variety of assay formats may be used to select ligands that specifically bind to a particular receptor. For example, solid-phase ELISA assays are routinely used to select ligands that specifically bind a receptor. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject" and "patient" are interchangeable and refer to an organism that receives treatment for a particular disease or condition as described herein (such as a condition associated with elevated levels of serum cholesterol or blood glucose) or that is diagnosed as having a disease or condition according to the methods described herein. Examples of subjects and patients include mammals, such as humans, primates, pigs, goats, rabbits, hamsters, cats, dogs, guinea pigs, members of the bovidae family (such as cattle, bison, buffalo, and yaks, among others), cows, sheep, horses, and bison, among others, receiving treatment for diseases or conditions, for example, elevated cholesterol, LDLs, triglycerides, or blood glucose.

As used herein, the term "transfection" refers to any of a wide variety of techniques commonly used for the introduction of exogenous DNA into a prokaryotic or eukaryotic host cell, e.g., electroporation, lipofection, calcium-phosphate precipitation, DEAE-dextran transfection and the like.

As used herein, the terms "treat" or "treatment" refer to therapeutic treatment, in which the object is to prevent or slow down (lessen) an undesired physiological change or disorder, such as the progression of a disease associated with an elevated level of cholesterol, such as heart disease, a disease associated with an elevated level of blood glucose, such as type-2 diabetes, or an autoimmune disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in which the condition or disorder is to be prevented.

As used herein, the term "vector" includes a nucleic acid vector, e.g., a DNA vector, such as a plasmid, a RNA vector, virus or other suitable replicon (e.g., viral vector). A variety of vectors have been developed for the delivery of polynucleotides encoding exogenous proteins into a prokaryotic or eukaryotic cell. Examples of such expression vectors are disclosed in, e.g., WO 1994/11026; incorporated herein by reference. Expression vectors of the invention contain a polynucleotide sequence as well as, e.g., additional sequence elements used for the expression of proteins and/or the integration of these polynucleotide sequences into the genome of a mammalian cell. Certain vectors that can be used for the recombinant expression of proteins include plasmids that contain regulatory sequences, such as promoter and enhancer regions, which direct gene transcription. Other useful vectors for recombinant protein expression contain polynucleotide sequences that enhance the rate of translation of these genes or improve the stability or nuclear export of the mRNA that results from gene transcription. These sequence elements include, e.g., 5' and 3' untranslated regions, an internal ribosomal entry site (IRES), and polyadenylation signal site in order to direct efficient transcription of the gene carried on the expression vector. The expression vectors of the invention may also contain a polynucleotide encoding a marker for selection of cells that contain such a vector. Examples of a suitable marker include genes that encode resistance to antibiotics, such as ampicillin, chloramphenicol, kanamycin, or nourseothricin.

BRIEF DESCRIPTION OF THE FIGURES

FIG. 4A is a table showing the average levels of various N-acetylated amino acids in a group of patients following administration with either BCG ("Avg(BCGpost)") or placebo ("Avg(Placebopost)"), as well as the p-value associated with the difference between these levels ("Ttest"). The data are shown as scaled levels such that all values are between 0 and 2.5.

FIG. 6 is a graph showing the effect of BCG treatment on the level of various lipogenic and lipolytic enzymes in patients with type I diabetes. The data demonstrate that BCG promotes an increase in the concentrations of cytokines, such as IL-6, TNFα, and interferon γ (IFNγ), as well as in the levels of lipolytic factors, such as carnitine palmitoyl transferases (e.g., CPT1A, CPT1B, and CPT1C), acyl-CoA oxidases (e.g., ACOX1, ACOX2, and ACOX3), and uncoupling protein (e.g., UCP2). The data further demonstrate the ability of BCG to attenuate endogenous levels of lipogenic factors, such as acetyl-CoA carboxylases (e.g., ACACA and ACACB), fatty acid synthase, stearoyl-CoA desaturase, malic enzyme, and glucose-6-phosphate dehydrogenase. BCG administration is additionally capable of promoting a decrease in the level of adiponectin receptors, such as ADIPOR1 and ADIPOR2, which modulate glucose metabolism and fatty acid oxidation.

FIG. 9I is a table reporting p-values for differences in metabolite levels for each of FIGS. 9B-9H. FIGS. 9J and 9K are graphs showing the ability of BCG to enhance hypoxia-inducible factor 1-α (HIF1-α) expression in BCG-treated peripheral blood lymphocytes in vitro and in BCG-treated monocytes in vitro. The conversion from a state of oxidative phosphorylation to a state of aerobic glycolysis is dictated in part by HIF1-α. Taken together, these data demonstrate the ability of BCG to potentiate this conversion by up-regulating HIF1-α expression.

DETAILED DESCRIPTION

Figure 1:
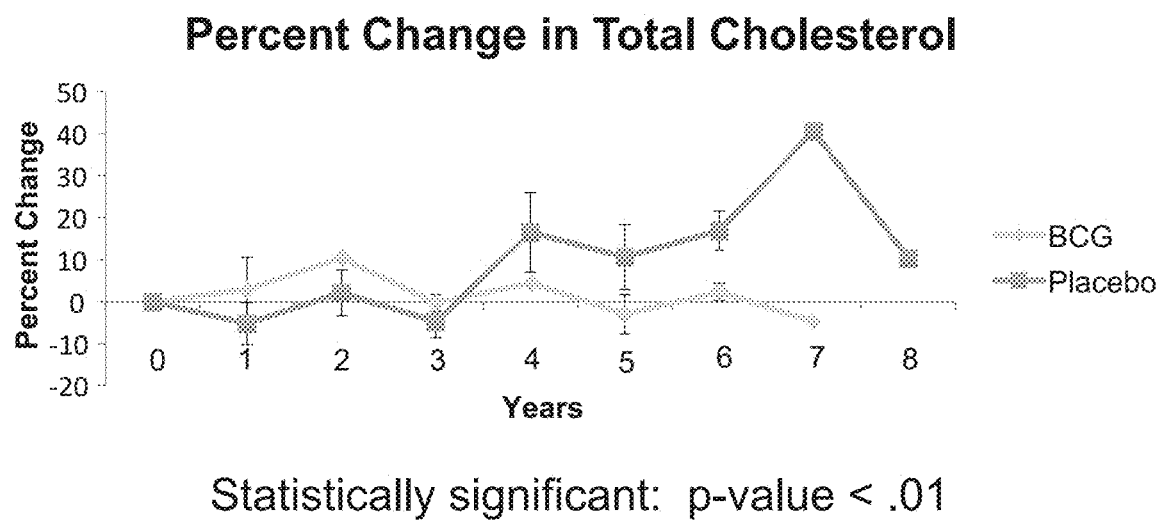
FIG. 1 is a graph showing the effect of BCG on serum cholesterol levels over the course of a multi-year study. The chart plots the percent change in total cholesterol level as a function of time, in years, following administration of either BCG or a placebo (control) to a group of patients presenting with high cholesterol levels. The data demonstrate that patients that were administered a placebo exhibited an average increase in total cholesterol of between about 10% and about 40% over the duration of the study, while patients that received BCG did not generally exhibit an increase in total serum cholesterol for up to seven years following the initial administration. These results support the finding that BCG can be used according to the methods of the invention to reduce or maintain serum cholesterol levels in patients (e.g., patients diagnosed as having elevated cholesterol).

The invention provides methods of treating diseases, such as those associated with elevated levels of cholesterol, by the administration of Bacillus Calmette-Guerin (BCG). Additionally, a variety of other diseases, such as autoimmune diseases, neurological conditions, allergies, allograft rejections, graft-versus-host diseases, asthma, macular degeneration, muscular atrophy, diseases related to miscarriage, atherosclerosis, bone loss, musculoskeletal diseases, and obesity can be treated according to the methods of the invention by administering an effective amount of BCG to a subject suffering from any of these diseases.

Methods of the invention also encompass procedures for diagnosing a disease in a subject and for determining whether a subject having a particular disease is likely to respond to treatment with a therapeutic agent (e.g., BCG) for the disease or would benefit from subsequent dosing of the therapeutic agent (e.g., BCG). The methods involve assessing the presence or level of one or more biomarkers in a subject (e.g., the level of cholesterol or blood glucose or analysis of DNA methylation patterns in the nuclear DNA isolated from a subject and/or determining the levels of one or more mRNA molecules, proteins, and/or metabolites in a sample isolated from the subject).

Diagnostic Methods of the Invention

Assessing Cytosine Methylation State

The invention is based in part on the discovery that BCG modulates the methylation and demethylation of cytosine residues within various endogenous DNA molecules, particularly DNA molecules within the nuclear genome of a mammalian cell. Cytosine residues that are adjacent to a guanine (e.g., a cytosine-guanine (CG, also referred to as CpG) dinucleotide are susceptible to methylation by DNA methyltransferases at the C-5 position of the cytosine nucleobase. Co-factors capable of donating a methyl group to the cytosine ring include S-adenosyl methionine (SAM), as shown in the biosynthetic scheme below:

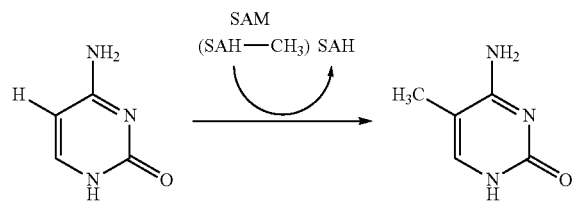

BCG is capable of modulating the methylation and demethylation of cytosine residues (e.g., increasing or decreasing the quantity of methylated cytosine residues within a particular DNA sequence), particularly within genes that encode transcription factors, such as FoxP3, or various cell-surface proteins, such as CD45. For instance, the administration of BCG to a subject may increase or decrease the quantity of methylated cytosine residues in a given DNA sequence, e.g., by about 5% or more (e.g., about 5%, 6%, 7%, 8%, 9%, 10%, 15%, 20%, 25%, 30%, 35%, 45%, 50%, or more) or by about 1.1-fold or more (e.g., about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) over the course of one or more hours, days, weeks, months, or years.

A physician of skill in the art can determine whether a patient (e.g., a patient that has already been diagnosed as having a particular disease, such as elevated cholesterol, LDLs, or triglycerides, reduced HDL levels, a disease associated with these altered serum lipid levels, or an immunological, neurological, or metabolic disease described herein) is likely to respond to BCG therapy by determining the quantity of methylated cytosine residues in a sample isolated from the subject and comparing this quantity to the amount of methylated cytosine residues in the DNA sequence of the same genetic locus in a reference sample. The reference sample may be a sample isolated from a healthy patient, optionally of the same age, sex, and/or weight, or the reference sample may be a standard quantity of methylated cytosine residues in a particular DNA sequence that is generally associated with a healthy physiological state or observed in healthy subjects, such as between 1 and 100 methylated cytosine residues (e.g., between 1 and 50 methylated cytosine residues, between 1 and 25 methylated cytosine residues, or between 1 and 10 methylated cytosine residues per molecule of DNA). A determination that the quantity of methylated cytosine residues in the sample isolated from the patient is greater than or less than the amount of methylated cytosine residues in the same DNA sequence within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject is likely to respond to treatment with a therapeutic agent, such as BCG, in order to treat the disease. In preferred embodiments, the gene that is analyzed encodes a transcription factor, such as FoxP3, or a cell-surface protein, such as CD45. In these cases, a determination that the quantity of methylated cytosine residues in the sample isolated from the subject is greater than the quantity of methylated cytosine residues in the same DNA sequence within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject is likely to respond to administration of a therapeutic agent, such as BCG, in order to treat the disease.

Methods of determining cytosine methylation state in a DNA sequence are known in the art and often include chemically modifying DNA from the subject and reference samples in order to convert unmethylated cytosine residues to uracil by incubating the DNA of interest with bisulfite. Bisulfite sequencing exploits the preferential deamination of cytosine bases to uracil bases in the presence of sodium hydroxide (NaOH) and sodium bisulfite. Methylated cytosine bases (5-methylcytosine), if present, are found almost exclusively at the cytosine position of a CG dinucleotide pair (e.g., 5'-CG-3'). Under acidic conditions, sodium bisulfite preferentially deaminates cytosine to uracil in a nucleophilic attack while the methyl group on 5-methylcytosine protects the amino group from the deamination. As a result, methylated cytosine is not converted under these conditions. Accordingly, the DNA's original methylation state can be analyzed by sequencing the bisulfite converted DNA and comparing the cytosine position of each cytosine-guanine (CG) dinucleotide pair of an unconverted nucleic acid to bases at the corresponding positions in the sequence of a bisulfite converted nucleic acid of interest. The cytosine position of a cytosine-guanine (CG) dinucleotide pair of the unconverted nucleic acid is identified as having been unmethylated if the corresponding position in the sequence of a bisulfite converted nucleic acid of interest is now occupied by thymine. The cytosine position of a cytosine-guanine (CG) dinucleotide pair of the unconverted nucleic acid is identified as having been methylated if the corresponding position in the sequence of a bisulfite converted nucleic acid of interest is occupied by cytosine. Exemplary protocols for determining the methylation state of cytosine residues in a DNA molecule of interest are described, e.g., in U.S. Pat. Nos. 8,577,615; 7,851,154; WO 2014/149356; and WO 2015/014759; the disclosures of each of which are incorporated herein by reference.

Analysis of mRNA and Protein Levels

In addition to modulating cytosine methylation state, BCG administration is capable of modulating the levels of various mRNA molecules and proteins, such as those associated with lipid and glucose metabolism and with regulating histone acetylation state. For instance, administration of BCG to a subject is capable of increasing the level of various cytokines, such as interleukin-6 (IL-6), tumor necrosis factor (TNFα), and interferon-gamma (IFNγ), as well as the mRNA molecules that encode these proteins. BCG is additionally capable of increasing the levels of lipolytic proteins in a subject, such as acyl co-enzyme A oxidase, carnitine palmitoyltransferase, lipase, and uncoupling protein, as well as the mRNA molecules that encode these proteins, e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more (e.g., about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) relative to the quantity of these substances in a reference sample, such as a sample isolated from a subject prior to administration of BCG. Additionally, BCG administration reduces the levels of adiponectin receptors (e.g., adiponectin receptors 1 and 2) and lipogenic proteins, such as acetyl co-enzyme A carboxylase α, acetyl co-enzyme A carboxylase β, fatty acid synthase, glyceraldehydes-6-phosphate dehydrogenase, stearoyl-CoA saturase, malic enzyme, and glucose-6-phosphate dehydrogenase, as well as the mRNA molecules that encode these proteins. BCG administration is additionally capable of decreasing the levels of one or more lysine acetyltransferases (KATs), such as KAT2A, KAT2B, KAT5, KAT6A, KAT6B, KAT7, and KAT8, as well as histone acetyltransferases and histone deacetylases (HDACs, such as HDAC1, HDAC2, HDAC3, HDAC4, HDAC5, HDAC6, HDAC7, HDAC8, HDAC9, HDAC10, HDAC11, HDAC1P1, HDAC1P2, SIRT1, SIRT2, SIRT3, SIRT4, SIRT5, SIRT6, and SIRT7) and histones (e.g., H2A, H2B, H3, and H4), as well as the mRNA molecules that encode these proteins, e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more (e.g., about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) relative to the quantity of these substances in a reference sample, such as a sample isolated from a subject prior to administration of BCG.

A physician of skill in the art can determine whether a patient (e.g., a patient that has already been diagnosed as having a particular disease, such as elevated cholesterol, LDLs, or triglycerides, reduced HDL levels, a disease associated with these altered serum lipid levels, or an immunological, neurological, or metabolic disease described herein) is likely to respond to BCG therapy by determining the quantity of one or more mRNA molecules or proteins in a sample isolated from the subject and comparing this quantity to the amount of the same mRNA molecule or protein in a reference sample. The reference sample may be a sample isolated from a healthy patient, optionally of the same age, sex, and/or weight, or the reference sample may be a standard concentration of the mRNA molecule or protein being analyzed that is generally associated with a healthy physiological state or observed in healthy subjects, such as between 1 pM and 10 mM (e.g., between 1 nM and 100 µM, between 1 nM and 10 µM, or between 1 nM and 1 µM). For instance, the reference sample may contain between 1 and 100,000 copies, or more, of an mRNA transcript (e.g., an mRNA transcript described herein). A reference sample may contain one or more cells, such as a cell of the hematopoietic lineage (e.g., a CD4+, CD25+ T-reg cell) that each contain between 1 and 100,000 copies, or more (e.g., about 1, 2, 3, 4, 5, 6, 7, 8, 9, 10, 20, 30, 40, 50, 60, 70, 80, 90, 100, 200, 300, 400, 500, 600, 700, 800, 900, 1,000, 5,000, 10,000, 50,000, or 100,000 copies, or more) of an mRNA transcript of interest, such as an mRNA transcript that encodes the CD45 or FoxP3 proteins. A determination that the quantity of lipolytic proteins or cytokines, such as those described herein, or the mRNA molecules that encode any one of these proteins, in the sample isolated from the patient is less than (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) the amount of the same lipolytic protein or cytokine within a reference sample indicates that the subject is likely to respond to treatment with a therapeutic agent, such as BCG, in order to treat the disease. Conversely, a determination that the quantity of lipogenic proteins, adiponectin receptors, KATs, histone acetyltransferases, HDACs, or histones, such as those described herein, or the mRNA molecules that encode any one of these proteins, in the sample isolated from the patient is greater than (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) the amount of the same protein or mRNA molecule within a reference sample indicates that the subject is likely to respond to treatment with a therapeutic agent, such as BCG, in order to treat the disease.

Methods for determining the concentration of proteins are known in the art and include, without limitation, ELISA-based assays, immunoblot assays, such as Western blot experiments, as well as HPLC, mass spectrometry, and UV-Vis spectroscopy, among others.

Standard methods for the detection and quantitation of mRNA molecules are additionally known in the art. Exemplary techniques for this analysis include Northern blot experiments and quantitative reverse-transcription polymerase chain reaction (PCR) techniques. Using this technique, it is possible to determine the quantity of a target mRNA molecule in a sample (e.g., in lysate obtained from a population of cells isolated from a patient, such as from the blood of a patient) by first reverse-transcribing the target mRNA to produce cDNA molecules encoding the protein that is obtained by translation of the target mRNA sequence. This technique involves lysing a population of cells isolated from a patient (e.g., T-lymphocytes, such as T-reg cells) that contain one or more copies of an mRNA molecule of interest. Optionally, the lysis can be performed in the presence of a chaotropic agent, such as between about 0.05 M and 1 M of a chaotropic agent. These are substances capable of disrupting the three dimensional structure of macromolecules such as proteins, DNA, or RNA and denatures them. Chaotropic agents interfere with stabilizing intramolecular interactions mediated by non-covalent forces such as hydrogen bonds, Van der Waals forces, and hydrophobic effects. Chaotropic reagents include but are not limited to urea, various lithium salts such lithium perchlorate, and guanidinium salts, such as guanidinium chloride. The cDNA is subsequently amplified using standard thermocycling techniques, e.g., as described in U.S. Pat. No. 8,623,602, the disclosure of which is incorporated herein by reference.

In certain cases, it may be advantageous to remove genomic DNA from a cell lysate to avoid the possibility of amplifying endogenous DNA in combination with cDNA during the thermocycling procedure. To this end, an effective technique for the removal of genomic DNA is enzymatic digestion. This can be achieved by treating the lysate sample with a DNAse, such as DNAse I or Shrimp DNAse, e.g., as disclosed in U.S. Pat. No. 6,541,204, the disclosure of which is incorporated herein by reference. In these cases, the DNAse is desirably inactivated following the degradation of genomic cDNA so as to prevent enzymatic cleavage of the cDNA synthesized from the target mRNA molecule. DNAse inactivation can be achieved, e.g., by incubating the reaction mixture containing the DNAse and the cell lysate at an elevated temperature, such as at between 80° C. and 90° C. for about 10 minutes.

To amplify the first cDNA strand from a target mRNA molecule, a primer complimentary to a sequence located at the 3' end of the target mRNA molecule can be designed, e.g., based on sequence elements present in mammalian mRNAs, such as poly-adenyl (pA) tails. Oligomeric deoxyribothymidine (dT) primers, which site-specifically bind to the pA tail of an mRNA, can be used as a primer to initiate the synthesis of the initial cDNA strand. To synthesize the subsequent cDNA strand, a primer complimentary to the 5' end of the initial cDNA strand is desirably included in the reaction mixture. This primer may be, e.g., a primer of between 10 and 30 nucleotides in length that has the corresponding DNA sequence of the target mRNA molecule in a 5'-to-3' direction. Examples of RNA dependent DNA polymerases that can be used for these cDNA synthesis steps include AMV Reverse Transcriptase (Roche Applied Science Cat. No. 11 495 062), MMuLV Reverse Transcriptase (Roche Applied Science Cat No. 011 062 603), and the recombinant Transcriptor Reverse Transcriptase (Roche Applied Science Cat. No. 03 531 317). Subsequently, all reagents are added that are required to amplify the generated single stranded cDNA by means of PCR, such as a thermostable DNA dependent DNA polymerases as well as target-specific forward and reverse amplification primers. The amplified DNA sequence is then quantitated using one of a variety of techniques, such as fluorescence resonant energy transfer (FRET)-based techniques, described in detail, e.g., in U.S. Pat. Nos. 5,210,015; 5,538,848; 5,487,972; 5,804,375, 5,118,801; WO 1997/046707; WO 1997/046712; and WO 1997/046714, the disclosures of each of which are incorporated herein by reference.

Determination of Amino Acid and Metabolite Levels

In addition to modulating mRNA and protein concentrations, BCG administration is capable of regulating the levels of various acetylated amino acids and methylated metabolites. For instance, administration of BCG to a subject is capable of increasing the level of various N-acetylated amino acids, such as N-acetylalanine, N-acetylaspartic acid, N-acetylserine, N-acetylthreonine, N-acetylhistidine, N-acetyl-3-methylhistidine, N-acetylvaline, and N-α-acetyllysine, and N-acetylmethionine (e.g., by promoting acetylation of alanine, aspartic acid, serine, threonine, histidine, 3-methylhistidine, valine, lysine, and methionine) e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more, relative to the quantity of these substances in a reference sample, such as a sample isolated from a subject prior to administration of BCG. BCG is additionally capable of increasing the levels of various methylated metabolites in a subject, such as N-α-acetyl-3-methylhistidine, 3-methylglutaconic acid, 3-methylglutarylcarnitine, and N-ε-trimethyllysine (e.g., by promoting the methylation of N-α-acetylhistidine, glutaconic acid, glutarylcarnitine, lysine, and cysteine), e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more, relative to the quantity of these substances in a reference sample, such as a sample isolated from a subject prior to administration of BCG.

Additionally, BCG administration reduces the levels of certain methylated metabolites, such as 4-methyl-2-oxopentanoic acid and 3-methyl-2-oxobutyric acid (e.g., by promoting demethylation of these metabolites) e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more, relative to the quantity of these substances in a reference sample, such as a sample isolated from a subject prior to administration of BCG.

A physician of skill in the art can determine whether a patient (e.g., a patient that has already been diagnosed as having a particular disease, such as elevated cholesterol, LDLs, or triglycerides, reduced HDL levels, a disease associated with these altered serum lipid levels, or an immunological, neurological, or metabolic disease described herein) is likely to respond to BCG therapy by determining the quantity of one or more acetylated amino acids or methylated metabolites in a sample isolated from the subject and comparing this quantity to the amount of the same substance in a reference sample. The reference sample may be a sample isolated from a healthy patient, optionally of the same age, sex, and/or weight, or the reference sample may be a standard concentration of the amino acid or metabolite being analyzed that is generally associated with a healthy physiological state or observed in healthy subjects, such as between 1 pM and 10 mM (e.g., between 1 nM and 100 µM, between 1 nM and 10 µM, or between 1 nM and 1 µM). A determination that the quantity of N-acetylalanine, N-acetylaspartic acid, N-acetylserine, N-acetylthreonine, N-acetylhistidine, N-acetyl-3-methylhistidine, N-acetylvaline, and N-α-acetyllysine, N-acetylmethionine, N-α-acetyl-3-methylhistidine, 3-methylglutaconic acid, 3-methylglutarylcarnitine, and/or N-ε-trimethyllysine in the sample isolated from the patient is less than the amount of the same substance within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject is likely to respond to treatment with a therapeutic agent, such as BCG, in order to treat the disease. Conversely, a determination that the quantity of 4-methyl-2-oxopentanoic acid and/or 3-methyl-2-oxobutyric acid in the sample isolated from the patient is greater than the amount of the same substance within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject is likely to respond to treatment with a therapeutic agent, such as BCG, in order to treat the disease.

Methods for determining the concentration of acetylated amino acids and methylated metabolites are known in the art and include, without limitation, nuclear magnetic resonance (NMR) spectroscopy, HPLC, mass spectrometry, and UV-Vis spectroscopy, among others.

Biomarkers for Diagnosing a Patient as Having a Disease

In addition to determining whether a patient is likely to respond to therapy (e.g., by administration of BCG), the methods of the invention can also be used to render a diagnosis of a particular disease (e.g., an immunological or neurological condition, or a disease associated with an elevated level of serum cholesterol, as described herein). For instance, a physician of skill in the art may analyze the level of cytosine methylation in a nuclear gene of interest in a sample isolated from a subject (e.g., a blood sample, such as a blood sample containing one or more T-reg cells from which the DNA is isolated and analyzed) in order to determine if the subject has a particular disorder. The quantity of methylated cytosine residues in a nuclear gene isolated from one or more cells of the sample can then be compared to the quantity of methylated cytosine residues in the same gene isolated from a reference sample. The reference sample may be a sample isolated from a healthy patient, optionally of the same age, sex, and/or weight as the subject being assessed. Alternatively, the reference sample may be a standard quantity of methylated cytosine residues in a particular DNA sequence that is generally associated with a healthy physiological state or observed in healthy subjects, such as between 1 and 100 methylated cytosine residues (e.g., between 1 and 50 methylated cytosine residues, between 1 and 25 methylated cytosine residues, or between 1 and 10 methylated cytosine residues per molecule of DNA). A determination that the quantity of methylated cytosine residues in the sample isolated from the patient is greater than or less than the amount of methylated cytosine residues in the same DNA sequence within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject may have a particular disease, such as an immunological or neurological disease, or a disorder associated with an elevated serum cholesterol concentration, as described herein. This determination may alternatively indicate that the patient would benefit from administration of BCG to prevent the onset of such a disease or condition. The gene that is analyzed may encode a transcription factor, such as FoxP3, or a cell-surface protein, such as CD45. In these cases, a determination that the quantity of methylated cytosine residues in the sample isolated from the subject is greater than the quantity of methylated cytosine residues in the same DNA sequence within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject may have a immunological, neurological, or cholesterol-related disorder. This determination may alternatively indicate that the patient would benefit from administration of BCG to prevent the onset of such a disease or condition.

In addition to rendering a diagnosis of a particular disease on the basis of cytosine methylation state, the methods of the invention additionally provide procedures for diagnosing a patient as having an immunological, neurological, or cholesterol-related disorder based on the levels of various mRNA molecules and proteins, such as those associated with lipid and glucose metabolism and with regulating histone acetylation state. For instance, a physician of skill in the art can use the methods of the invention to measure the level of one or more cytokines, such as IL-6, TNFα, and IFNγ, as well as the mRNA molecules that encode these proteins, in order to diagnose a patient as having a particular disorder. A physician may additionally or alternatively monitor the level of one or more lipolytic proteins in a subject, such as acyl co-enzyme A oxidase, carnitine palmitoyltransferase, lipase, and uncoupling protein, as well as the mRNA molecules that encode these proteins. A determination that the quantity of one or more of these lipolytic proteins or cytokines, or one or more of the mRNA molecules that encode these proteins, in the sample isolated from the patient is less than (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) the amount of the same lipolytic protein or cytokine within a reference sample (such as a sample isolated from a healthy subject as described above) indicates that the subject being assessed may have an immunological, neurological, or cholesterol-related disorder as described herein. Conversely, a determination that the quantity of lipogenic proteins, adiponectin receptors, KATs, histone acetyltransferases, HDACs, or histones, such as those described herein, or the mRNA molecules that encode any one of these proteins, in the sample isolated from the patient is greater than (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) the amount of the same protein or mRNA molecule within a reference sample indicates that the subject may have an immunological, neurological, or cholesterol-related disorder as described herein. These determinations, individually or collectively, may alternatively indicate that the patient would benefit from administration of BCG to prevent the onset of such a disease or condition.

A physician of skill in the art can also determine whether a patient has a particular disease (e.g., a disease associated with elevated cholesterol, LDLs, or triglycerides, reduced HDL levels, a disease associated with these altered serum lipid levels, or an immunological, neurological, or metabolic disease described herein) by determining the quantity of one or more acetylated amino acids or methylated metabolites in a sample isolated from the subject and comparing this quantity to the amount of the same substance in a reference sample. As described for the methods of diagnosis on the basis of DNA methylation patterns and mRNA/protein levels, the reference sample may be a sample isolated from a healthy patient, optionally of the same age, sex, and/or weight, or the reference sample may be a standard concentration of the amino acid or metabolite being analyzed that is generally associated with a healthy physiological state or observed in healthy subjects, such as between 1 pM and 10 mM (e.g., between 1 nM and 100 μM, between 1 nM and 10 μM, or between 1 nM and 1 μM). A determination that the quantity of N-acetylalanine, N-acetylaspartic acid, N-acetylserine, N-acetylthreonine, N-acetylhistidine, N-acetyl-3-methylhistidine, N-acetylvaline, and N-α-acetyllysine, N-acetylmethionine, N-α-acetyl-3-methylhistidine, 3-methylglutaconic acid, 3-methylglutarylcarnitine, and/or N-ε-trimethyllysine in the sample isolated from the patient is less than the amount of the same substance within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject may have an immunological, neurological, or cholesterol-related disease, e.g., as described herein. Conversely, a determination that the quantity of 4-methyl-2-oxopentanoic acid and/or 3-methyl-2-oxobutyric acid in the sample isolated from the patient is greater than the amount of the same substance within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject may have an immunological, neurological, or cholesterol-related disease, e.g., as described herein. These determinations, individually or collectively, may alternatively indicate that the patient would benefit from administration of BCG to prevent the onset of such a disease or condition.

In addition to the above, the methods of the invention additionally provide procedures for diagnosing a patient as having hyperglycemia or a disease associated with hyperglycemia, such as type-2 diabetes, as well as methods of predicting whether such patients would benefit from BCG treatment. I have discovered that BCG is capable of suppressing cholesterol levels, for instance, by increasing the expression of NR1H3, thereby promoting the expression of cholesterol-suppressing genes such as ABCA1, ABCG, APOE, FAS, and SCD1 and down-regulating the expression of glucose-elevating genes such as FBP1, G6PD, and PKM. I have also discovered that BCG reduces the expression of enzymes that promote flux through the Krebs cycle, such as ACLY, ACO2, CS, DLD, OGDH, SDHB, and SUCLG1, while enhancing the expression of glycolytic enzymes such as HK2, G6P1, TP12, GALK1, and GALM, as well as glucose transporters, such as SLC2A6. BCG additionally increases the expression of HIF1-α, inducing glucose depletion by promoting a transition from oxidative phosphorylation to aerobic glycolysis, which consumes glucose much more rapidly so as to produce adenosine triphosphate. A physician of skill in the art can use the methods of the invention to measure the level of one or more the preceding substances, or an mRNA molecule encoding such substances, so as to determine whether a patient has a hyperglycemic condition or may benefit from BCG therapy. For instance, a determination that the quantity of one or more of the preceding enzymes that promotes flux through the Krebs cycle, α-ketobutyrate, 2-hydroxybutyrate, FBP1, G6PD, or PKM is increased (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) relative to the amount of the same substance within a reference sample (such as a sample isolated from a healthy subject as described above) indicates that the subject being assessed may have hyperglycemia or a disease associated with hyperglycemia, and/or may benefit from BCG therapy. Conversely, a determination that the quantity a glycolytic enzyme, glucose transporter, HIF1-α, NR1H3, lactate, or 1,5-anhydroglucitol is reduced (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as by about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) relative to the amount of the substance within a reference sample indicates that the subject may have hyperglycemia or a disease associated with hyperglycemia, and/or may benefit from BCG therapy. These determinations, individually or collectively, may indicate that the patient would benefit from subsequent administration of BCG in one or more additional doses.

Methods of Treatment and Prevention

Administration of BCG to Modulate Serum Lipid Levels

The invention provides methods of treating a subject that has one or more diseases by administering an effective amount of BCG to the subject. According to the methods of the invention, BCG can be administered to a subject in order to reduce the level of cholesterol, low-density lipoproteins (LDLs), and/or triglycerides. The subject may be one that has already been diagnosed as having elevated levels of cholesterol, LDLs, and/or triglycerides. The subject may also be one that is prone to development of hypercholesteremia in the future; as such, BCG can also be used as a prophylactic therapy according to the methods of the invention. Cholesterol levels in a healthy human subject are typically about 129 mg/dL, and therefore a serum cholesterol concentration above this threshold may be considered an elevated level of cholesterol. For instance, a subject that has a serum cholesterol level of about 135 mg/dL, 140 mg/dL, 145 mg/dL, 150 mg/dL, 155 mg/dL, 160 mg/dL, 165 mg/dL, 170 mg/dL, 175 mg/dL, 180 mg/dL, 185 mg/dL, 190 mg/dL, 195 mg/dL, 200 mg/dL, or greater, can be considered to have elevated an level of cholesterol. A subject may be classified as having an elevated level of LDLs if the subject has an LDL level of about 80 mg/dL or greater (e.g., about 80 mg/dL, 85 mg/dL, 90 mg/dL, 95 mg/dL, 100 mg/dL, 105 mg/dL, 110 mg/dL, 115 mg/dL, 120 mg/dL, 125 mg/dL, 130 mg/dL, 135 mg/dL, 140 mg/dL, 145 mg/dL, 150 mg/dL, or greater). A subject may be classified as having an elevated level of triglycerides if the subject has a serum triglyceride level of about 100 mg/dL or more (e.g., about 100 mg/dL, 105 mg/dL, 110 mg/dL, 115 mg/dL, 120 mg/dL, 125 mg/dL, 130 mg/dL, 145 mg/dL, 150 mg/dL, 155 mg/dL, 160 mg/dL, 165 mg/dL, 170 mg/dL, 175 mg/dL, 180 mg/dL, 195 mg/dL, 200 mg/dL, 205 mg/dL, 210 mg/dL, 215 mg/dL, 220 mg/dL, 225 mg/dL, 230 mg/dL, 235 mg/dL, 240 mg/dL, 245 mg/dL, 250 mg/dL, 255 mg/dL, 260 mg/dL, 265 mg/dL, 270 mg/dL, 275 mg/dL, 280 mg/dL, 285 mg/dL, 290 mg/dL, 300 mg/dL, 305 mg/dL, 310 mg/dL, 315 mg/dL, 320 mg/dL, 325 mg/dL, 330 mg/dL, 335 mg/dL, 340 mg/dL, 345 mg/dL, 350 mg/dL, 355 mg/dL, 360 mg/dL, 365 mg/dL, 370 mg/dL, 375 mg/dL, 380 mg/dL, 385 mg/dL, 390 mg/dL, 400 mg/dL, 405 mg/dL, 410 mg/dL, 415 mg/dL, 420 mg/dL, 425 mg/dL, 430 mg/dL, 435 mg/dL, 440 mg/dL, 445 mg/dL, 450 mg/dL, 455 mg/dL, 460 mg/dL, 465 mg/dL, 470 mg/dL, 480 mg/dL, 485 mg/dL, 490 mg/dL, 495 mg/dL, 500 mg/dL, or greater).

In addition, a subject may be classified as having an elevated level of cholesterol, LDLs, or triglycerides if the subject currently has a serum level of one or more of these substances that is higher than that which has previously been observed in a sample isolated from the subject. For instance, even though a subject may have a serum cholesterol level of less than 129 mg/dL (e.g., about 100 mg/dL, 105 mg/dL, 110 mg/dL, 115 mg/dL, 120 mg/dL, or 125 mg/dL), the subject can be considered to have an elevated level of cholesterol if the subject has a serum cholesterol level that is higher than a serum cholesterol level that was previously observed in a sample isolated from the subject (e.g., between about 1 day and about 5-20 years ago). The elevated cholesterol level may be increased, for instance, by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the level of serum cholesterol previously measured in a sample from the subject. Likewise, a subject can be considered to have an elevated level of serum LDLs if the subject has a higher serum LDL level that that which has been previously observed in a sample from the subject, e.g., even if the subject currently has a serum LDL level that is less than about 80 mg/dL (e.g., about 75 mg/dL, 70 mg/dL, 65 mg/dL, 60 mg/dL, 55 mg/dL, 50 mg/dL, 45 mg/dL, 40 mg/dL, or lower). The elevated LDL level may be increased, for instance, by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the level of serum LDLs previously measured in a sample from the subject. Additionally, a subject can be considered to have elevated levels of serum triglycerides if the subject has a higher serum triglyceride level that that which has been previously observed in a sample from the subject, e.g., even if the subject currently has a serum triglyceride level that is less than about 100 mg/dL (e.g., about 95 mg/dL, 90 mg/dL, 85 mg/dL, 80 mg/dL, 75 mg/dL, 70 mg/dL, 65 mg/dL, 60 mg/dL, 55 mg/dL, 50 mg/dL, 45 mg/dL, 40 mg/dL, or lower). The elevated triglyceride level may be increased, for instance, by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the level of serum triglycerides previously measured in a sample from the subject or relative to a healthy level of serum triglycerides (e.g., less than about 150 mg/dL).

A subject can be considered to be in need of an increase in the level of serum HDLs if the subject has a serum HDL level of about 40 mg/dL or lower (e.g., about 40 mg/dL, 35 mg/dL, 30 mg/dL, 25 mg/dL, 20 mg/dL, 15 mg/dL, or lower). Additionally, a subject can be considered to be in need of an increase in the level of serum HDLs if the subject has a serum HDL level that is lower than that which has previously been measured in a sample from the subject. For instance, a subject can be considered to be in need of an increase in the level of serum HDLs even if the subject has a serum HDL level that is about 40 mg/dL or greater. It is known in the art that higher HDL levels more effectively protect a subject against developing elevated serum cholesterol and diseases associated therewith, such as a disease described herein. A subject in need of an increase in serum HDLs may have a current serum HDL level that is reduced, e.g., by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the level of serum HDLs previously measured in a sample from the subject.

According to the methods of the invention, BCG can be administered to a subject in order to decrease the level of cholesterol, LDLs, and/or triglycerides in the subject. Administration of BCG may reduce the level of serum cholesterol, LDLs, and/or triglycerides by about 5% or more. For instance, a subject that has been diagnosed as having an elevated level of cholesterol can be administered BCG in order to lower the level of serum cholesterol in the subject, e.g., by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the subject's level of serum cholesterol at the time the BCG is administered. BCG may effectively reduce the subject's serum cholesterol level to a healthy value of about 129 mg/dL or lower, e.g., administration of BCG may reduce a subject's serum cholesterol level to about 200 mg/dL, 195 mg/dL, 190 mg/dL, 185 mg/dL, 180 mg/dL, 185 mg/dL, 180 mg/dL, 175 mg/dL, 170 mg/dL, 165 mg/dL, 160 mg/dL, 155 mg/dL, 150 mg/dL, 145 mg/dL, 140 mg/dL, 135 mg/dL, 130 mg/dL, 125 mg/dL, 120 mg/dL, 115 mg/dL, 110 mg/dL, 105 mg/dL, 100 mg/dL, or lower. Additionally or alternatively, a subject that has been diagnosed as having an elevated level of serum LDLs can be administered BCG in order to lower the level of serum LDLs in the subject, e.g., by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the subject's level of serum LDLs at the time the BCG is administered. BCG may effectively reduce the subject's serum LDL level to a healthy value of about 80 mg/dL or lower, e.g., administration of BCG may reduce a subject's serum cholesterol level to about 150 mg/dL, 145 mg/dL, 140 mg/dL, 135 mg/dL, 130 mg/dL, 125 mg/dL, 120 mg/dL, 115 mg/dL, 110 mg/dL, 105 mg/dL, 100 mg/dL, 95 mg/dL, 90 mg/dL, 85 mg/dL, 80 mg/dL, 75 mg/dL, 70 mg/dL, 65 mg/dL, 60 mg/dL, 55 mg/dL, 50 mg/dL, 45 mg/dL, 40 mg/dL, or lower. According to the methods of the invention, a subject that has been diagnosed as having an elevated level of serum triglycerides can be administered BCG in order to lower the level of serum triglycerides in the subject, e.g., by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the subject's level of serum triglycerides at the time the BCG is administered. Administration of BCG may effectively reduce the subject's serum triglyceride level to a healthy value of about 100 mg/dL or lower, e.g., administration of BCG may reduce the subject's serum triglyceride level to about 500 mg/dL, 495 mg/dL, 490 mg/dL, 485 mg/dL, 480 mg/dL, 475 mg/dL, 470 mg/dL, 465 mg/dL, 460 mg/dL, 455 mg/dL, 450 mg/dL, 445 mg/dL, 440 mg/dL, 435 mg/dL, 430 mg/dL, 425 mg/dL, 420 mg/dL, 415 mg/dL, 410 mg/dL, 405 mg/dL, 400 mg/dL, 395 mg/dL, 390 mg/dL, 385 mg/dL, 380 mg/dL, 375 mg/dL, 370 mg/dL, 365 mg/dL, 360 mg/dL, 355 mg/dL, 350 mg/dL, 355 mg/dL, 350 mg/dL, 345 mg/dL, 340 mg/dL, 335 mg/dL, 330 mg/dL, 325 mg/dL, 320 mg/dL, 315 mg/dL, 310 mg/dL, 305 mg/dL, 300 mg/dL, 295 mg/dL, 290 mg/dL, 285 mg/dL, 280 mg/dL, 275 mg/dL, 270 mg/dL, 265 mg/dL, 260 mg/dL, 255 mg/dL, 250 mg/dL, 245 mg/dL, 240 mg/dL, 235 mg/dL, 230 mg/dL, 225 mg/dL, 220 mg/dL, 215 mg/dL, 210 mg/dL, 205 mg/dL, 200 mg/dL, 195 mg/dL, 190 mg/dL, 185 mg/dL, 180 mg/dL, 175 mg/dL, 170 mg/dL, 165 mg/dL, 160 mg/dL, 155 mg/dL, 150 mg/dL, 145 mg/dL, 140 mg/dL, 135 mg/dL, 130 mg/dL, 125 mg/dL, 120 mg/dL, 115 mg/dL, 110 mg/dL, 105 mg/dL, 100 mg/dL, 95 mg/dL, 90 mg/dL, 85 mg/dL, 80 mg/dL, 75 mg/dL, 70 mg/dL, 65 mg/dL, 60 mg/dL, 55 mg/dL, 50 mg/dL, 45 mg/dL, 40 mg/dL, or lower.

Additionally or alternatively, BCG can be administered to a subject that is prone to develop elevated levels of serum cholesterol, LDLs, and/or triglycerides, even though the patient may not currently exhibit elevated serum concentrations of these lipids. For instance, BCG can be administered to a subject that currently has a serum cholesterol level that is less than 129 mg/dL (e.g., about 100 mg/dL, 105 mg/dL, 110 mg/dL, 115 mg/dL, 120 mg/dL, or 125 mg/dL) and that is not considered to presently have elevated levels of serum cholesterol (e.g., the subject's current serum cholesterol level is within the range (e.g., within 10%-25%) of a cholesterol level previously observed for the subject). The administration of BCG may prevent the subject from developing, or may reduce the likelihood that the subject will develop, elevated serum cholesterol levels, such that upon future examination of the subject, e.g., between about 1 day and 20 years, or more, following the administration (such as about 1 day, 1 week, 1 month, 6 months, 1 year, 2 years, 3 years, 4 years, 5 years, 10 years, 15 years, or 20 years, or more, following the administration of BCG), the subject may present serum cholesterol levels that are not considered elevated (e.g., based on the description of an elevated cholesterol level described above. In the same manner, BCG can be used as a prophylactic therapy for preventing the development of elevated serum LDL and/or triglyceride levels, such that following the administration of BCG, the subject may exhibit serum LDL and/or triglyceride levels that are not considered elevated (e.g., based on the descriptions of elevated serum LDLs and triglycerides described above). Prophylactic BCG therapy may be indicated in a subject that has a family history of, or a genetic predisposition to develop, elevated levels of serum cholesterol, LDLs, and/or triglycerides.

The methods of the invention can also be used to elevate the level of serum HDLs in a subject by administration of BCG. According to these methods, the BCG may induce an increase in the level of serum HDLs, e.g., by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the subject's level of serum HDLs at the time the BCG is administered. Administration of BCG may effectively increase the subject's serum HDL level to a healthy value of about 40 mg/dL, e.g., administration of BCG may increase the subject's serum HDL level to about 40 mg/dL, 45 mg/dL, 50 mg/dL, 55 mg/dL, 60 mg/dL, 65 mg/dL, 70 mg/dL, 75 mg/dL, 80 mg/dL, 85 mg/dL, 90 mg/dL, 95 mg/dL, 100 mg/dL, or greater.

Additionally or alternatively, BCG can be administered to a subject that is prone to develop attenuated levels of serum HDLs, even though the patient may not currently exhibit decreased serum concentrations of these lipids. For instance, BCG can be administered to a subject that currently has a serum HDL level that is between about 40 mg/dL and about 80 mg/dL (e.g., about 40 mg/dL, 45 mg/dL, 50 mg/dL, 55 mg/dL, 60 mg/dL, 65 mg/dL, 70 mg/dL, 75 mg/dL, and 80 mg/dL) and that is not considered to presently be in need of an increase in the level of serum HDLs (e.g., the subject's current serum HDL level is within the range (e.g., within 10%-25%) of a serum HDL level previously observed for the subject). The administration of BCG may prevent the subject from developing decreased serum HDL level, such that upon future examination of the subject, e.g., between about 1 day and 20 years, or more, following the administration (such as about 1 day, 1 week, 1 month, 6 months, 1 year, 2 years, 3 years, 4 years, 5 years, 10 years, 15 years, or 20 years, or more, following the administration of BCG), the subject may exhibit serum HDL levels that are not considered attenuated (e.g., the subject may not be in need of an increased HDL level as described above). Prophylactic BCG therapy may be indicated in a subject that has a family history of, or a genetic predisposition to develop, attenuated (e.g., lower) levels of serum HDLs.

In addition to methods of modulating serum lipid levels, the invention provides methods of treating a variety of diseases associated with elevated serum cholesterol, LDL, and/or triglyceride concentrations. For instance, BCG can be administered to a subject in order to treat hypercholesterolemia, hyperlipidemia, coronary heart disease, peripheral arterial disease (PAD), peripheral vascular disease, hypertension, stroke, diabetes, metabolic syndrome, obesity, and/or insulin resistance in the subject. BCG administration can also be performed according to the methods of the invention in order to alleviate one or more symptoms associated with such diseases, including elevated levels of lactate dehydrogenase (LDH), LDL, and triglycerides in the subject. For instance, BCG administration may be capable of reducing LDH levels in a subject, e.g., by about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to the subject's level of serum HDLs at the time the BCG is administered. Additional symptoms that can be alleviated by administration of BCG include angina, arrhythmia, and heart failure. BCG can also be administered as a prophylactic to prevent these diseases and symptoms associated therewith or to reduce the likelihood that these diseases and/or one or more of their symptoms may develop. The sections below provide a description of exemplary diseases that can be treated and prevented by administration of BCG.

Effect of BCG on NR1H3 Expression

Figure 7A:
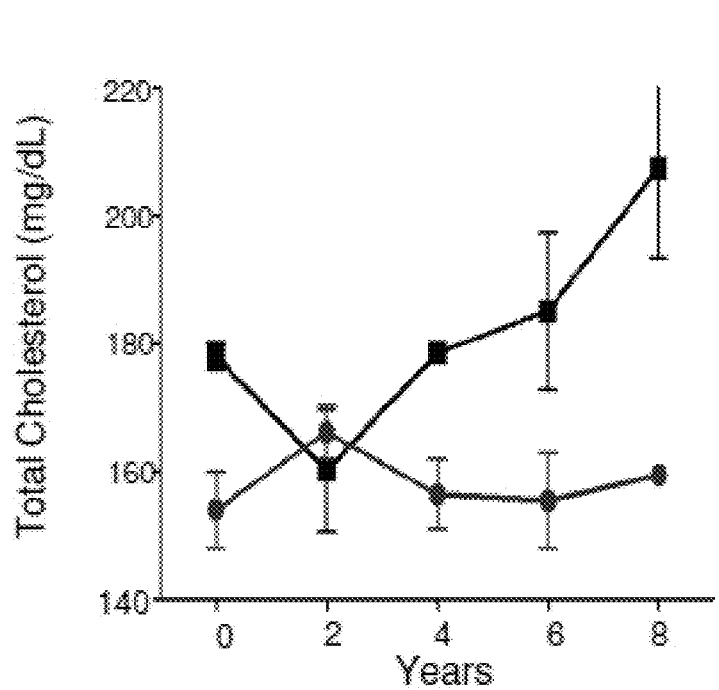
FIG. 7A is a graph showing the ability of intradermally-administered BCG (circles) to stabilize and lower cholesterol levels in human subjects over the course of an 8-year investigation relative to subjects not treated with BCG (squares).
Figure 7B:
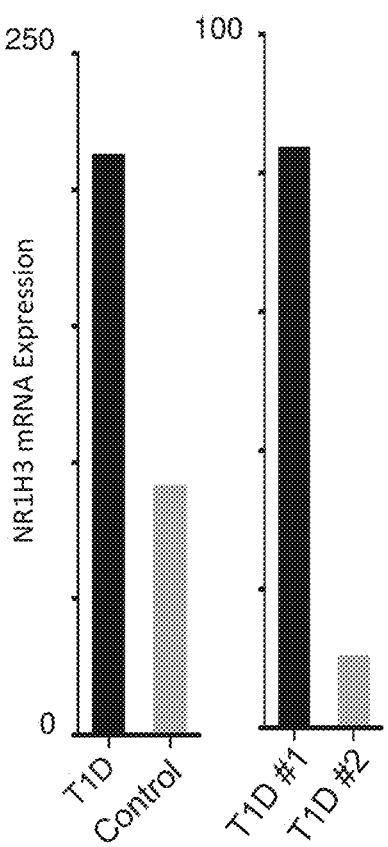
FIG. 7B is a graph showing the ability of BCG to promote the expression of nuclear receptor subfamily 1 group H member 3 (NR1H3) in cultured human peripheral blood lymphocytes (left) and in vivo in human subjects with type 1 diabetes (right). Cultured cells were monitored for NR1H3 expression prior to and 48 hours following exposure to BCG. Human subjects were assessed for NR1H3 expression prior to and 8 weeks following BCG administration.
Figure 7C:
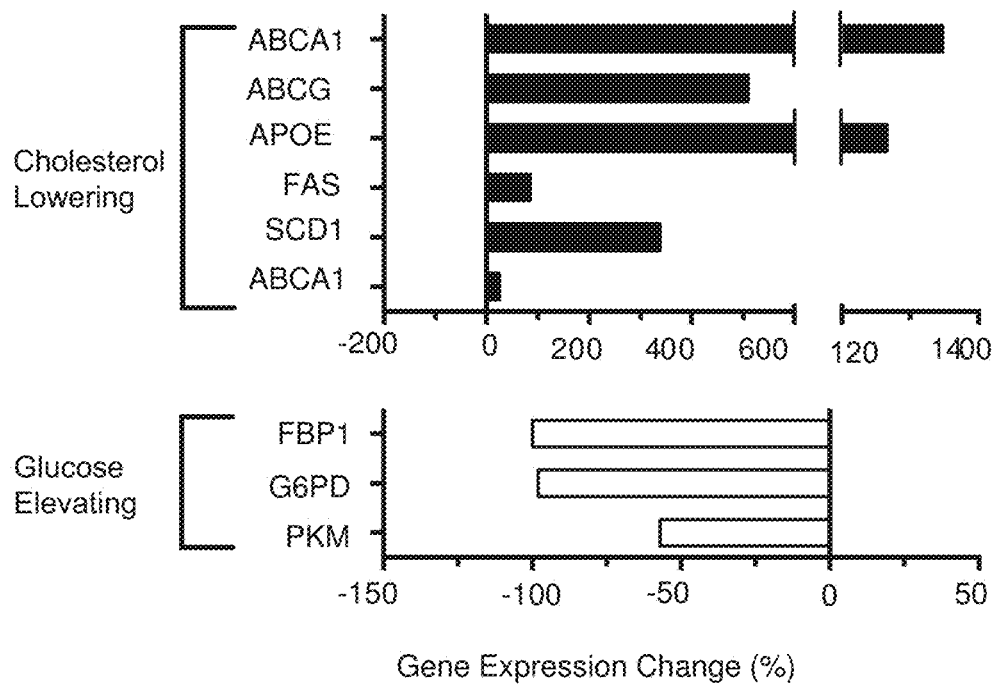
FIG. 7C is a graph showing the ability of BCG to promote the expression of the cholesterol-suppressing genes adenosine triphosphate binding cassette subfamily A member 1 (ABCA1), adenosine triphosphate binding cassette subfamily G (ABCG), apolipoprotein E(APOE), Fas cell surface death receptor (FAS), and stearoyl-CoA desaturase (SCD1) and reduce the expression of the glucose-elevating genes fructose-bisphosphatase 1 (FBP1), glucose-6-phosphate dehydrogenase (G6PD), and muscle pyruvate kinase (PKM) in human type-1 diabetes patients. Taken together, these data demonstrate the capacity of BCG to confer multiple beneficial effects by suppressing total cholesterol and blood glucose concentrations.

The present invention is based in part on the discovery that BCG is capable of promoting the expression of nuclear receptor subfamily 1 group H member 3 (NR1H3). NR1H3 is a nuclear receptor protein capable of κp-regulating the expression of cholesterol-suppressing genes, such as adenosine triphosphate binding cassette subfamily A member 1 (ABCA1), adenosine triphosphate binding cassette subfamily G (ABCG), apolipoprotein E(APOE), Fas cell surface death receptor (FAS), and stearoyl-CoA desaturase (SCD1). NR1H3 additionally reduces the expression of glucose-elevating genes, such as fructose-bisphosphatase 1 (FBP1), glucose-6-phosphate dehydrogenase (G6PD), and muscle pyruvate kinase (PKM). As demonstrated in FIGS. 7A-7C, BCG is therefore capable of conferring multiple beneficial effects at the molecular level, including the rapid consumption of glucose and the attenuation of cholesterol.

Methods of Ttreating and Preventing Immunological, Neurological, and Metabolic Conditions In addition to methods of modulating serum lipid levels, the invention provides methods of treating a variety of other diseases and conditions by administration of BCG. For instance, the methods of the invention can be used to diagnose the presence of an immunological and/or neurological disorder (e.g., by assessing the level and/or presence of one or more of the biomarkers described herein), and, once diagnosed, the subject can be treated by administration of BCG. BCG induces the secretion of TNFα, a TNFR2 agonist, which activates the proliferation of regulatory T-cells (T-reg) that attenuate the growth of T- and B-lymphocytes that cross-react with self antigens and epitopes from other non-threatening molecules. Exemplary disorders that can be treated by administration of BCG include autoimmune diseases, such as type I diabetes, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Essential Mixed Cryoglobulinemia, Fibromyalgia-Fibromyositis, Graves' Disease, Guillain-Barré, Hashimoto's Thyroiditis, Hypothyroidism, Idiopathic Pulmonary Fibrosis, Idiopathic Thrombocytopenia Purpura (ITP), IgA Nephropathy, Juvenile Arthritis, Lichen Planus, Lupus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Takayasu Arteritis, Temporal Arteritis/Giant Cell Arteritis, Ulcerative Colitis, Uveitis, Vasculitis, Vitiligo, and Wegener's Granulomatosis. In some embodiments of the invention, subjects that are treated for any of these autoimmune diseases are administered BCG and are not administered a TNFR2 agonist.

Other diseases that can be treated by administration of BCG include neurological conditions, such as a brain tumor, a brain metastasis, a spinal cord injury, schizophrenia, epilepsy, Amyotrophic lateral sclerosis (ALS), Parkinson's disease, Autism, Alzheimer's disease, Huntington's disease, and stroke. In some embodiments of the invention, subjects that are treated for any of these neurological conditions are administered BCG and are not administered a TNFR2 agonist.

Additionally, BCG can be administered to a subject in order to treat an allergy, such as a food allergy, seasonal allergy, pet allergy, hives, hay fever, allergic conjunctivitis, poison ivy allergy oak allergy, mold allergy, drug allergy, dust allergy, cosmetic allergy, or chemical allergy. In some embodiments of the invention, subjects that are treated for any of these allergies are administered BCG and are not administered a TNFR2 agonist.

BCG can be administered to a subject, e.g., a mammalian subject, such as a human, suffering from a graft rejection. BCG may treat graft rejections, e.g., by stimulating the production of TNFα, which in turn may bind TNFR2 receptors on the surface of autoreactive CD8+ T-cells that cross-react with antigens presented on the surface of the graft and induce apoptosis in these CD8+ T-cells, or may stimulate the expansion of T-reg cells that may subsequently eliminate autoreactive CD8+ T-cells. Examples of graft rejections that can be treated by administration of BCG include, without limitation, skin graft rejection, bone graft rejection, vascular tissue graft rejection, ligament graft rejection, or organ graft rejection. Exemplary ligament graft rejections that can be treated according to the methods of the invention include cricothyroid ligament graft rejection, periodontal ligament graft rejection, suspensory ligament of the lens graft rejection, palmar radiocarpal ligament graft rejection, dorsal radiocarpal ligament graft rejection, ulnar collateral ligament graft rejection, radial collateral ligament graft rejection, suspensory ligament of the breast graft rejection, anterior sacroiliac ligament graft rejection, posterior sacroiliac ligament graft rejection, sacrotuberous ligament graft rejection, sacrospinous ligament graft rejection, inferior pubic ligament graft rejection, superior pubic ligament graft rejection, anterior cruciate ligament graft rejection, lateral collateral ligament graft rejection, posterior cruciate ligament graft rejection, medial collateral ligament graft rejection, cranial cruciate ligament graft rejection, caudal cruciate ligament graft rejection, and patellar ligament graft rejection. Example of organ graft rejections that can be treated according to the methods of the invention include heart graft rejection, lung graft rejection, kidney graft rejection, liver graft rejection, pancreas graft rejection, intestine graft rejection, and thymus graft rejection. In some embodiments of the invention, subjects that are treated for any of these graft rejections are administered BCG and are not administered a TNFR2 agonist.

BCG can also be used to treat a patient in need of organ repair or regeneration, e.g., by inducing the proliferation of cells within a damaged tissue or organ. BCG can be administered to a mammalian subject, such as a human, to stimulate TNFα secretion, which may in turn bind TNFR2 on the surface of cells within damaged tissue so as to induce TRAF2/3− and/or NFκB-mediated cell proliferation. The growth of T-reg cells (e.g., CD4+, CD25+, FOXP3+ T-reg cells) that is induced by BCG administration can subsequently modulate the activity of T- and B-lymphocytes that cross-react with cells of endogenous organs or tissues. For instance, the stimulation of TNFα secretion can have the effect of reducing populations of cytotoxic T-lymphocytes (e.g., CD8+ T-cells) that are often associated with mounting an inappropriate immune response that can cause an immunological disorder. In certain cases, BCG may be capable of reducing the growth of a population of CD8+ T-cells, e.g., by about 50% to about 200% relative to untreated cells (e.g., 50%, 75%, 100%, 125%, 150%, 175%, or 200%). Examples of tissues and organs that may be induced to regenerate by administration of BCG to a subject (e.g., a mammalian subject, such as a human) include the pancreas, salivary gland, pituitary gland, kidney, heart, lung, hematopoietic system, cranial nerves, heart, blood vessels including the aorta, olfactory gland, ear, nerves, structures of the head, eye, thymus, tongue, bone, liver, small intestine, large intestine, gut, lung, brain, skin, peripheral nervous system, central nervous system, spinal cord, breast, embryonic structures, embryos, and testes. In some embodiments of the invention, subjects that are administered BCG to stimulate organ repair or regeneration are administered BCG and are not administered a TNFR2 agonist.

In each case, the subject may be diagnosed as having a disease by detecting one or more of the biomarkers described herein, such as methylated cytosine residues within a nuclear gene (e.g., FoxP3 or CD45), a cytokine (e.g., IL-6, TNFα, or IFNγ), a lipolytic protein (e.g., acyl co-enzyme A oxidase, carnitine palmitoyltransferase, lipase, or uncoupling protein), a lipogenic protein (e.g., acetyl co-enzyme A carboxylase α, acetyl co-enzyme A carboxylase β, fatty acid synthase, glyceraldehydes-6-phosphate dehydrogenase, stearoyl-CoA saturase, malic enzyme, or glucose-6-phosphate dehydrogenase), adiponectin receptor (e.g., adiponectin receptor 1 or adiponectin receptor 2), lysine acetyltransferase (e.g., KAT2A, KAT2B, KAT5, KAT6A, KAT6B, KAT7, or KAT8), histone acetyltransferase, histone deacetylase (e.g., HDAC1, HDAC2, HDAC3, HDAC4, HDAC5, HDAC6, HDAC7, HDAC8, HDAC9, HDAC10, HDAC11, HDAC1P1, HDAC1P2, SIRT1, SIRT2, SIRT3, SIRT4, SIRT5, SIRT6, or SIRT7), histone (e.g., H2A, H2B, H3, or H4), an mRNA molecule encoding any of these proteins, an acetylated amino acid (e.g., N-acetylalanine, N-acetylaspartic acid, N-acetylserine, N-acetylthreonine, N-acetylhistidine, N-acetyl-3-methylhistidine, N-acetylvaline, and N-α-acetyllysine, and N-acetylmethionine), or a methylated metabolite (e.g., N-α-acetyl-3-methylhistidine, 3-methylglutaconic acid, 3-methylglutarylcarnitine, N-ε-trimethyllysine, 4-methyl-2-oxopentanoic acid, and 3-methyl-2-oxobutyric acid).

Methods of Treating Hyperglycemia and Associated Disorders

Figure 8A:
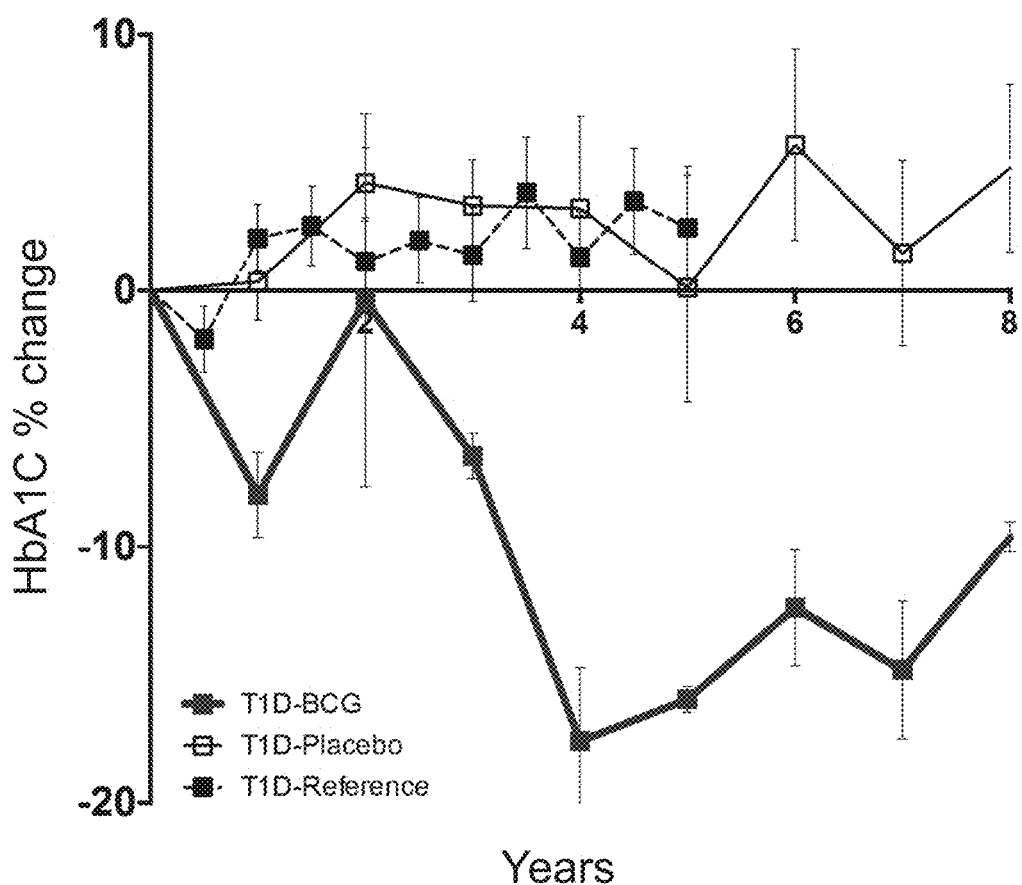
FIG. 8A is a graph showing the ability of BCG to lower glycated hemoglobin levels relative to untreated and to placebo-treated subjects in long-term human type-1 diabetic patients receiving two doses of BCG separated by 4 weeks.
Figure 8B:
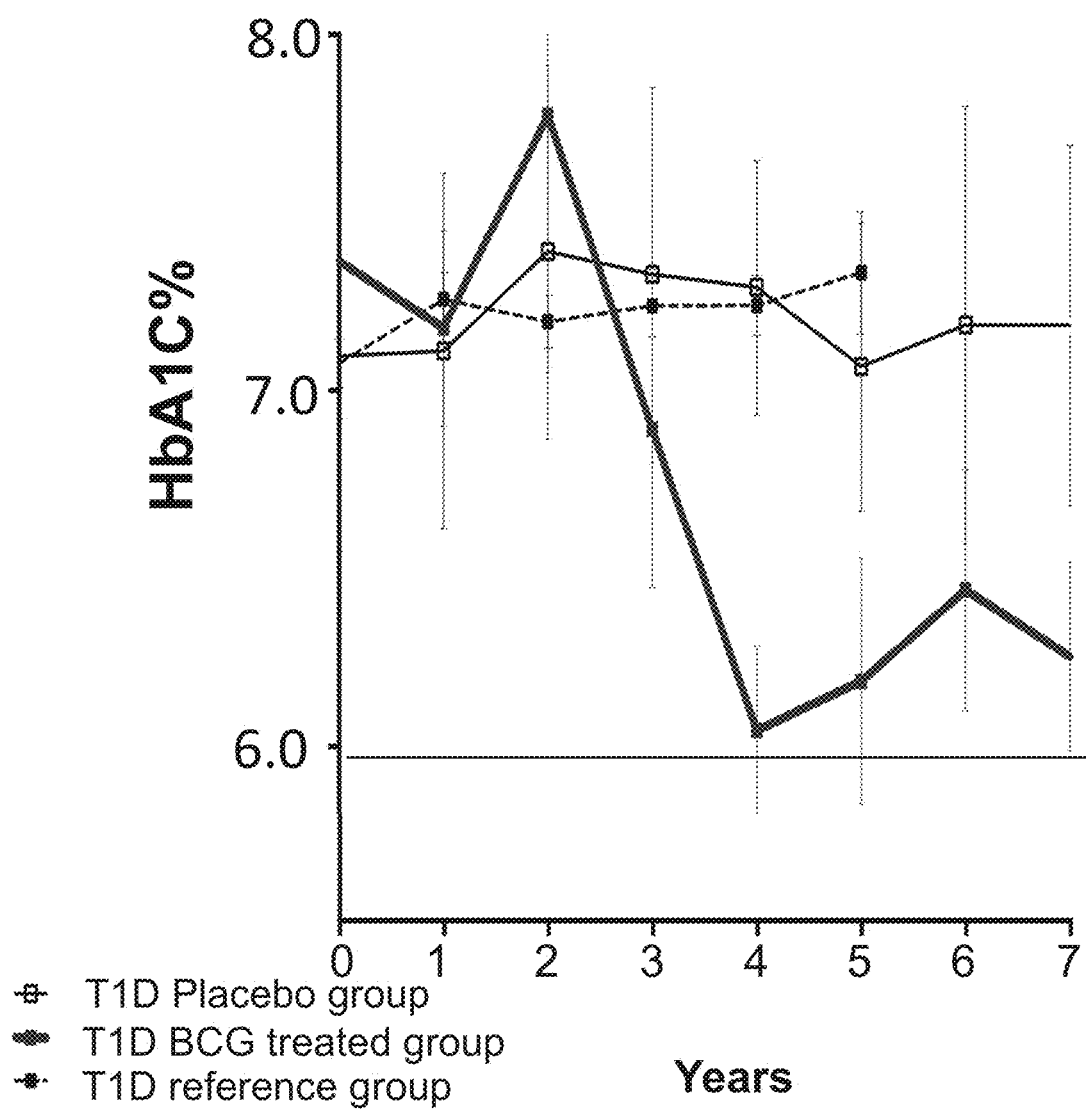
FIG. 8B is a graph demonstrating the ability of BCG to promote a decrease in glycated hemoglobin levels in hyperglycemic human patients and to stabilize glycated hemoglobin near normal physiologic levels.
Figure 9A:
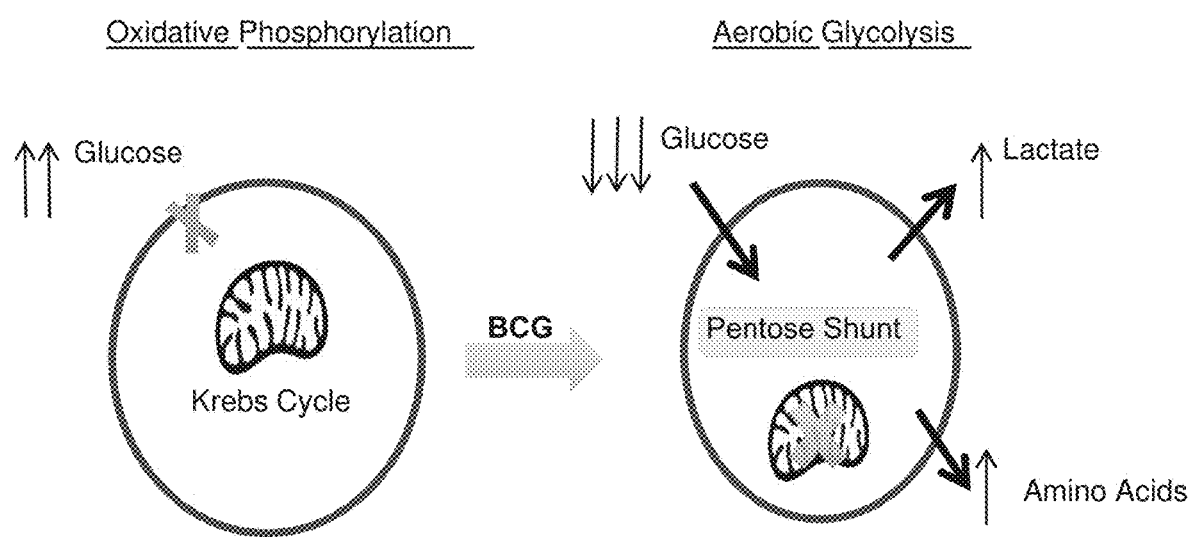
FIG. 9A is a schematic depicting the metabolic conversion from oxidative phosphorylation to a state of aerobic glycolysis induced by BCG.
Figure 9B:
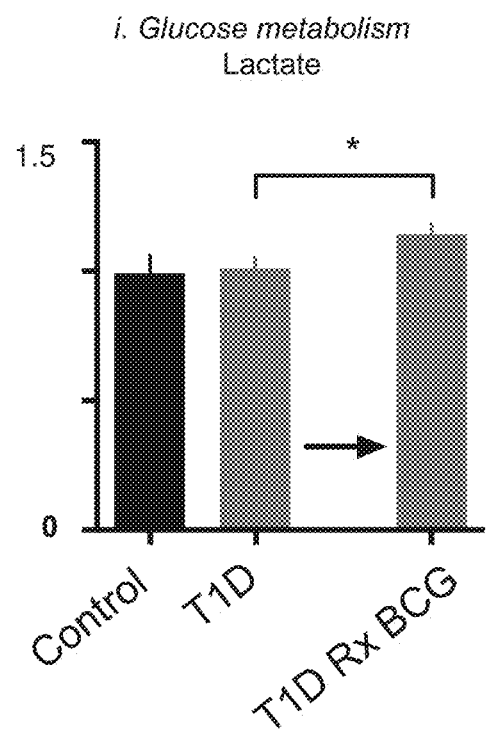
FIGS. 9B-9H are a series of graphs showing the ability of BCG to induce an increase in flux through glycolysis (as shown, for instance, by an increase in lactate levels) in human patients suffering from type-1 diabetes. The glucose-suppressing effect of BCG is independent of pancreas regeneration, as BCG did not promote an increase in the rate of purine biosynthesis as assessed by monitoring adenine, N6-carbamoylthreonyadenosine, and methylguanine.
Figure 9C:
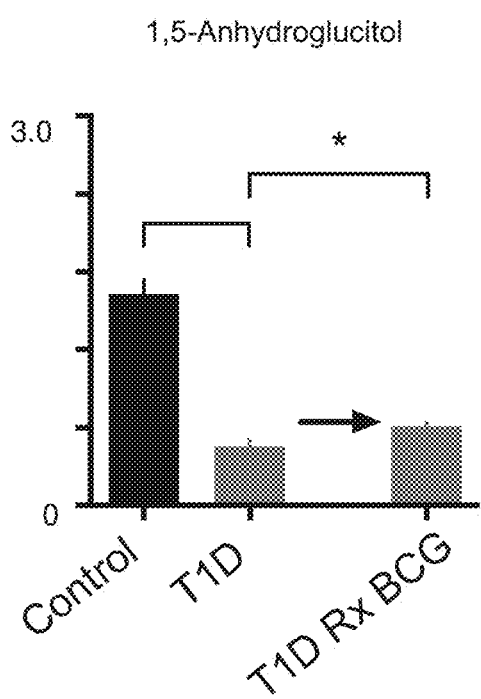
Figure 9D:
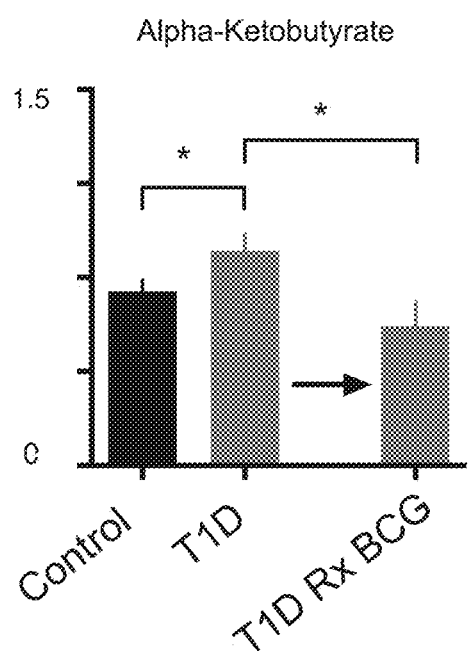
Figure 9E:
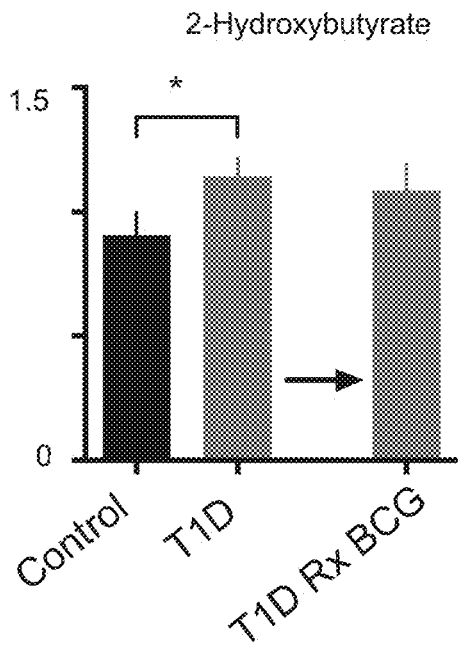
Figure 9F:
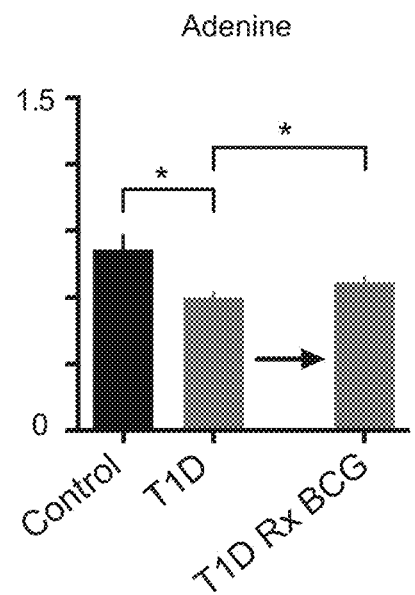
Figure 9G:
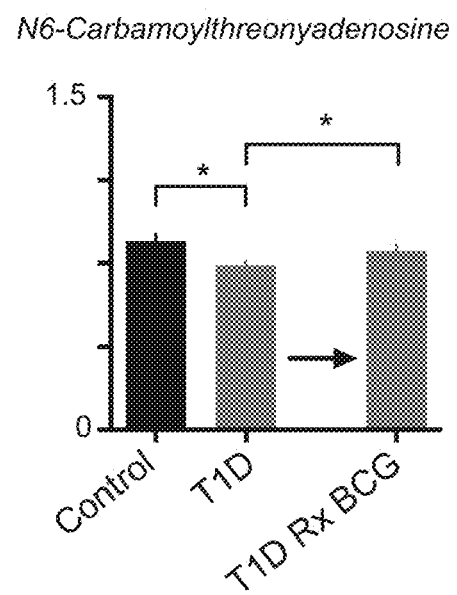
Figure 9H:
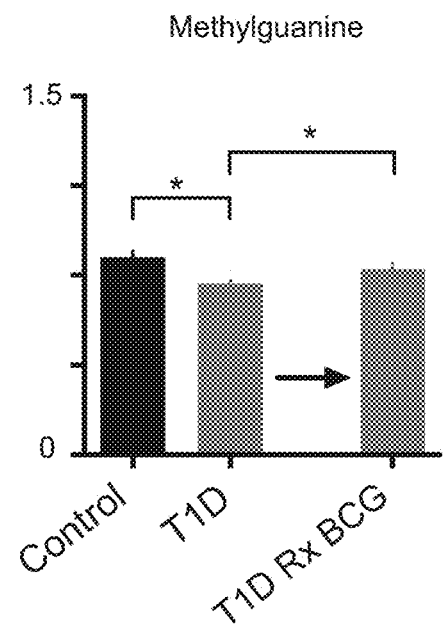
Figure 10A:
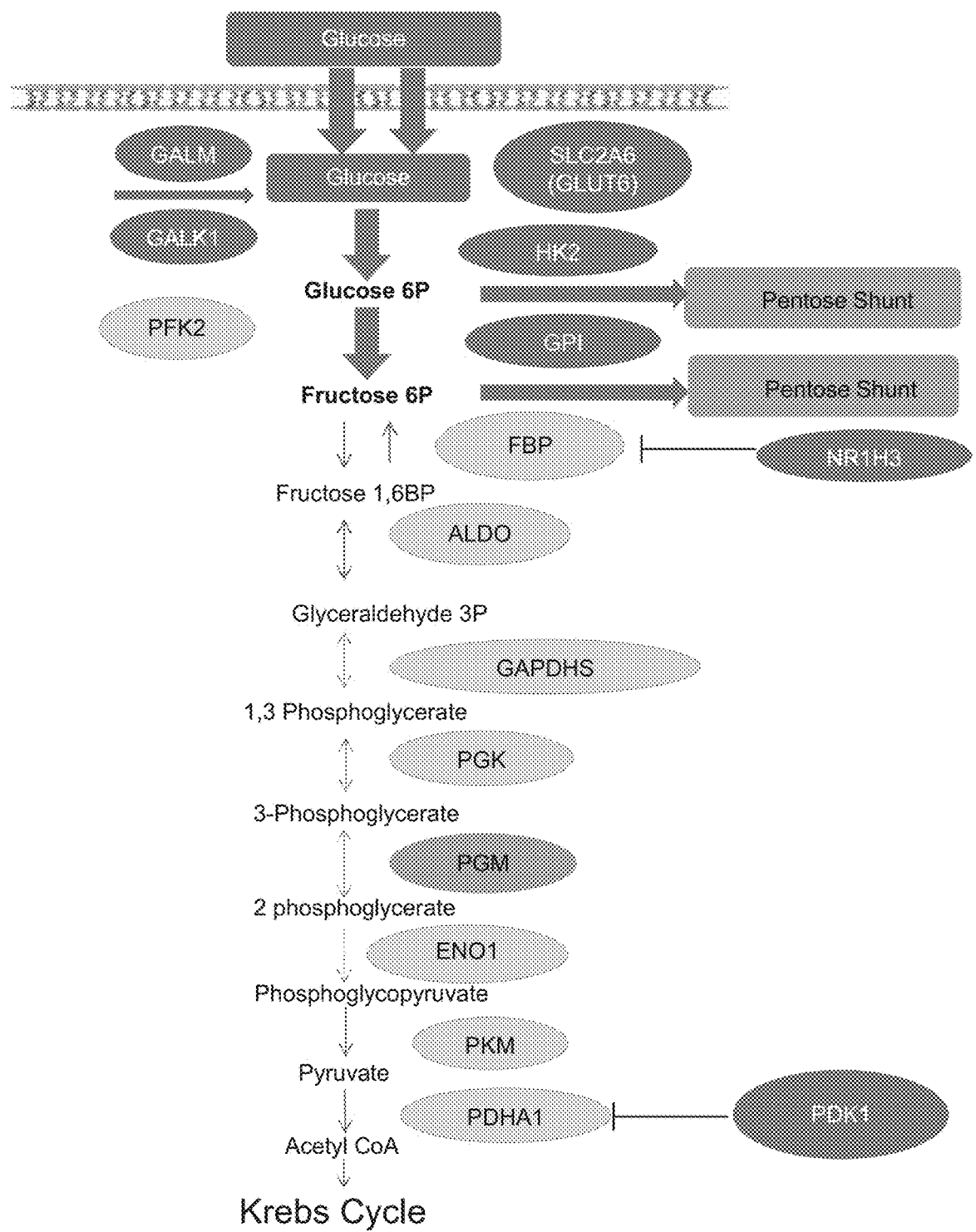
FIG. 10A is a schematic illustrating the metabolism of glucose by the pentose phosphate shunt, glycolysis, and the Krebs cycle.
Figure 10B:
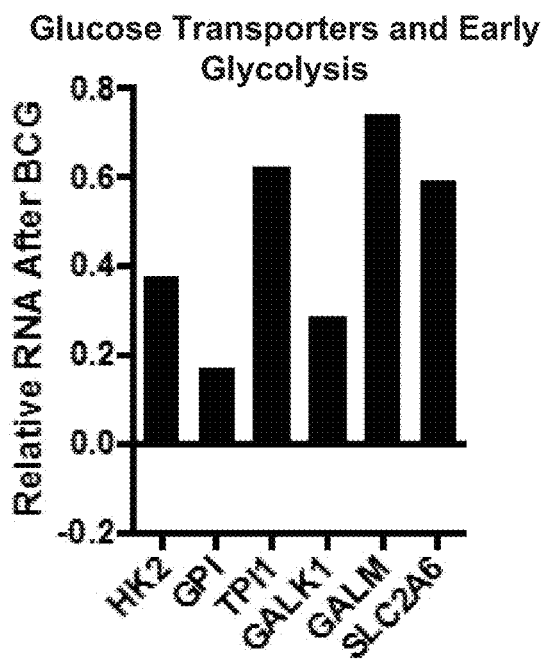
FIGS. 10B-10D are a series of graphs demonstrating the ability of BCG to up-regulate the glycolytic enzymes hexokinase 2 (HK2), glucose-6-phosphate isomerase (G6PI), triosephosphate isomerase 1 (TPI1), galactokinase 1 (GALK1), and galactose mutarotase (GALM), as well as the glucose transporter solute carrier family 2 member 6 (SLC2A6), as well as to modulate the expression of various proteins involved in the Krebs cycle. Gene expression data are from mRNA quantitation experiments conducted using cultured peripheral blood lymphocytes. Taken together, these data demonstrate the ability of BCG to promote processes that result in sugar uptake and glucose consumption.
Figure 10C:
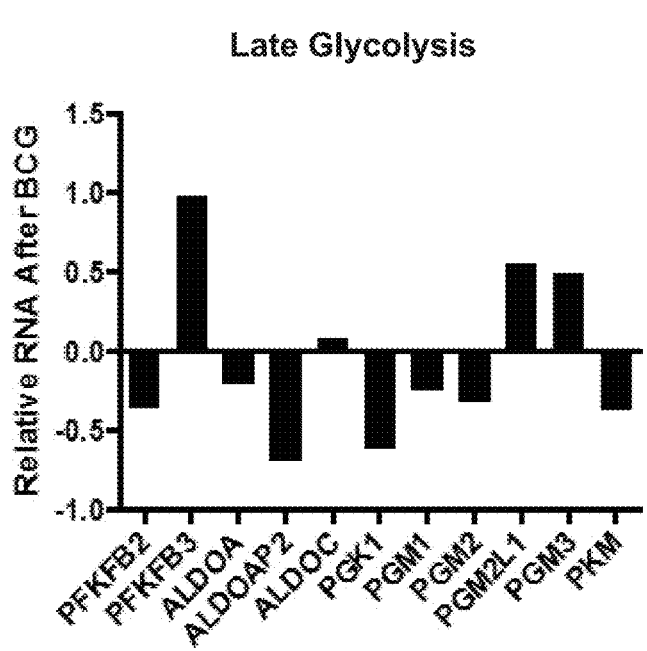
Figure 10D:
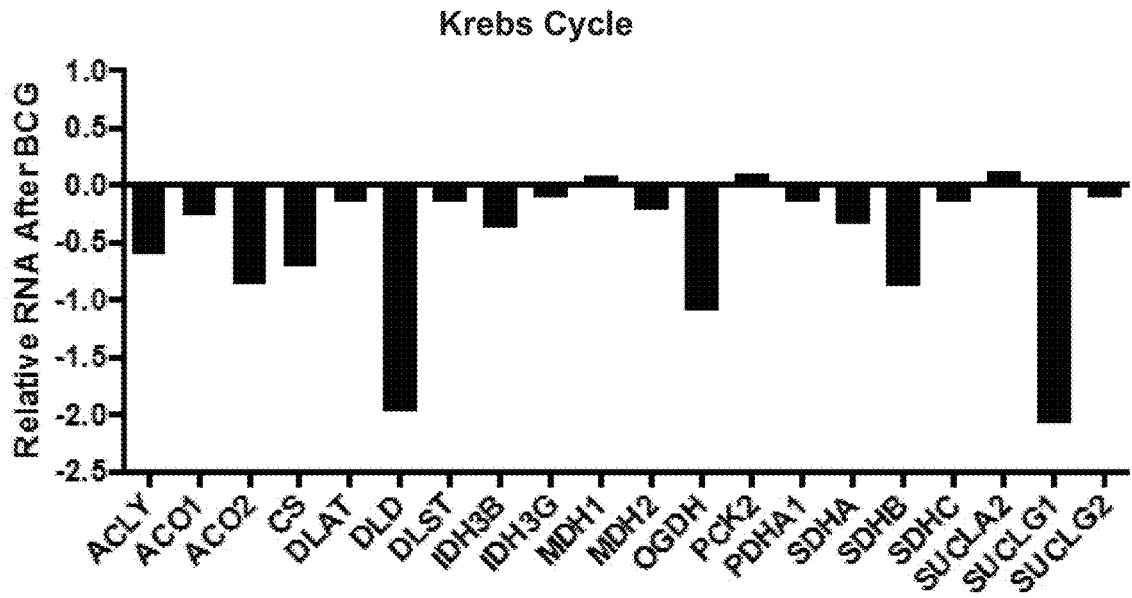
Figure 11A:
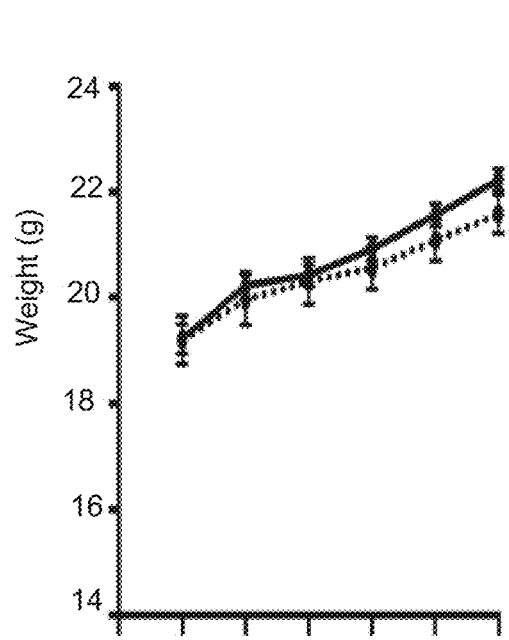
FIGS. 11A-11D are a series of graphs demonstrating the ability of BCG to modulate weight and blood sugar levels in hyperglycemic mouse models. Normal BALB/c mice (FIGS. 11A and 11C) were treated with or without BCG. For normal mice, this administration had no consequences on blood sugar level or on weight. Weight was measured in these investigations since elevated blood sugar levels are associated with weight loss. Chemically induced hyperglycemic BALB/c mice (FIGS. 11B and 11D) were treated with either BCG or saline. Following BCG administration, hyperglycemic mice exhibited an improved ability to maintain weight (FIG. 11B) and reduced blood glucose relative to mice not treated with BCG (FIG. 11D). Hyperglycemia was induced in BALB/c mice by administration of streptozotocin, an agent that non-specifically elevates blood glucose. This is important, as the mice treated in this study were not suffering from a specific disease, but were rather suffering from a non-specific increase in blood sugar. Taken together, these data demonstrate the ability of BCG to reduce blood glucose concentrations in hyperglycemic subjects in any disease state, regardless of the underlying etiology.
Figure 11B:
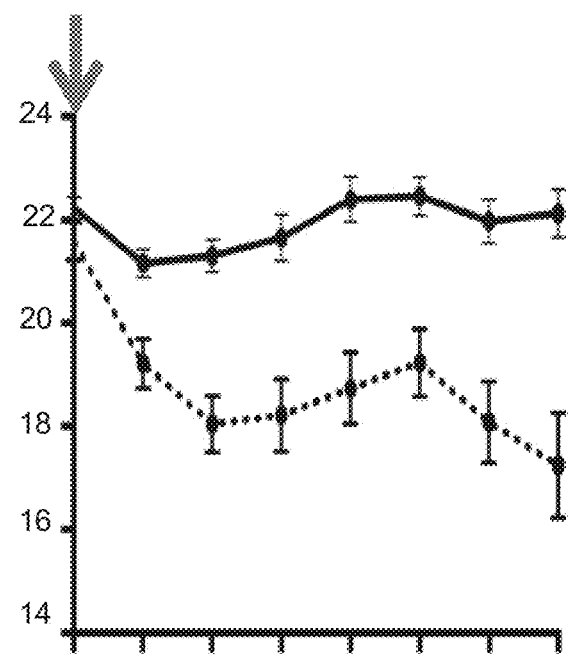
Figure 11C:
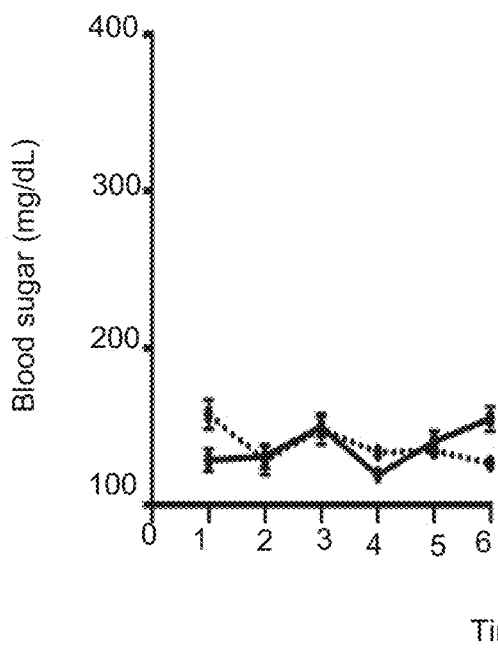
Figure 11D:
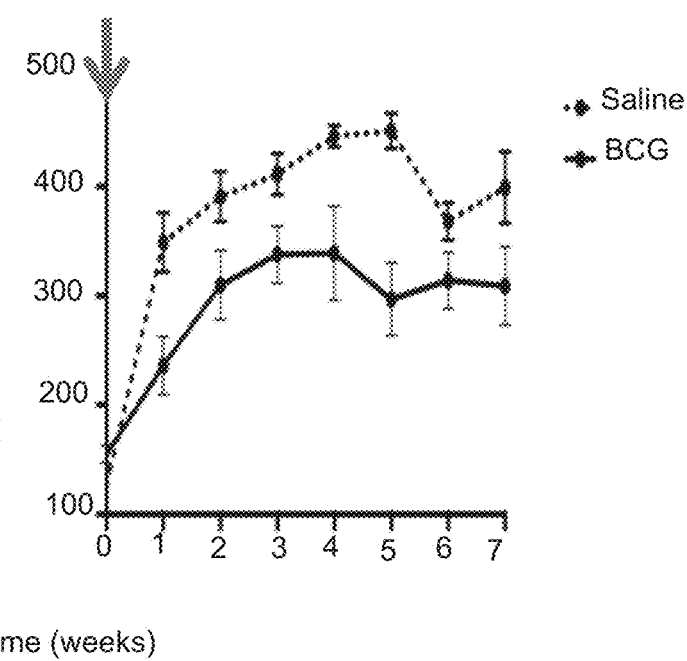
Figure 11E:
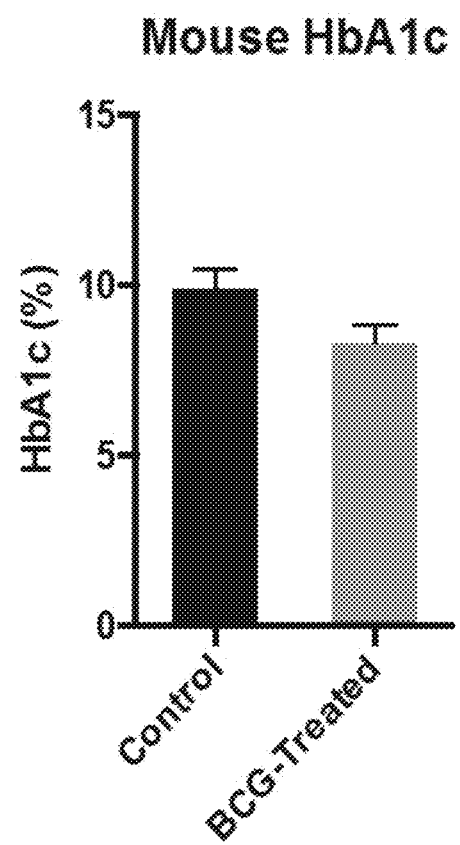
FIG. 11E is a graph showing the ability of BCG to reduce glycated hemoglobin in streptozotocin-treated BALB/c mice. As glycated hemoglobin is an indicator of total blood glucose, these data further demonstrate the ability of BCG to reduce blood glucose concentrations in subjects exhibiting elevated blood sugar regardless of the underlying biochemical cause.

Another basis for the present invention is the discovery that BCG is capable of suppressing blood glucose levels in patients in need thereof (e.g., mammalian patients, such as human patients), such as hyperglycemic patients. I have discovered that BCG is capable of inducing a metabolic conversion from a state of oxidative phosphorylation to a state of aerobic glycolysis. A result of this conversion is the rapid consumption of glucose in vivo. This beneficial effect of BCG is shown, for instance, in FIGS. 3, 8A, and 8B, which demonstrate the ability of BCG to suppress and stabilize glycated hemoglobin levels in human subjects. Glycated hemoglobin is an indicator of total blood glucose concentration and can be used to detect hyperglycemic subjects. BCG is capable of inducing this conversion, known as the Warburg Effect, by augmenting the expression of hypoxia-inducible factor 1-α (HIF1-α). As shown in FIGS. 9 and 10, BCG administration is capable of κp-regulating HIF1-α and promotes the expression of glucose transporters and early glycolytic enzymes. As glycolysis is less thermodynamically efficient than oxidative phosphorylation, this conversion increases glucose consumption substantially to meet the demand for adenosine triphosphate. Administration of BCG thus provides an innovative method to lower blood sugar. This mechanism is unique and provides advantages over insulin treatment, as no hypoglycemia occurs due to administration of BCG and the blood sugar lowering effect due to BCG treatment is more robust than that achieved with standard insulin therapy. The use of BCG thus represents a method for reducing blood glucose or to replace the use of insulin to control blood sugar, regardless of underlying etiology.

Patients that may be suitably treated (e.g., to reduce blood sugar level) using BCG include those suffering from a disease associated with an elevated blood glucose level, such as type 2 diabetes, noninsulin-dependent diabetes mellitus (NIDDM), nonalcoholic steatohepatitis (NASH), metabolic syndrome, cystic fibrosis, drug induced hyperglycemia, insulin resistance syndromes, diseases caused by genetic mutations in the pancreas, cancer, infection, Leprechaunism, Rabson Mandenhall syndrome, lipoatrophic diabetes, pancreatitis, trauma, hemochromatoisis, fibrocalculous pancreatopathy, acromegaly, Cushings syndrome, glucagonoma, pheochromocytoma, hyperthyroism, somatostatinoma, aldosteroma, infections associated with beta cell destruction, Rubella, coxsachie virus B, mumps, cytomegatolovirus infection, adenovirus infection, a genetic syndrome, stiff person syndrome, anti-insulin receptor abnormalities, liver disease, and renal failure. In some embodiments, the drug induced hyperglycemia is induced by one or more agents selected from the group consisting of steroids, cortisol, thiazides, diazocide, calcineurin inhibitors, oral contraceptives, beta adrenergic agonists, nicotinic acid, pentamidine, alpha interferon, anti-psychotic agents, anti-retroviral agents, and rodenticides (e.g., pyrinuron). In some embodiments, the cancer is pancreatic cancer. In some embodiments, the genetic syndrome is selected from the group consisting of Down's syndrome, Klinefelter's syndrome, Turner syndrome, Woldfram syndrome, and Friendreich ataxia. In some embodiments, the subject has undergone a pancreatectomy. The subject may exhibit one or more mutations in a mitochondrial gene, such as hepatic nuclear factor 1 (MODY3), glucokinase (MODY2), and hepatocyte nuclear factor 4-α (MODY1).

Additionally or alternatively, BCG administration can alleviate or reduce a symptom associated with the disease, such as polyphagia, polydipsia, polyuria, blurred vision, fatigue, cardiac arrhythmia, stupor, dry mouth, and poor wound healing.

Methods of Combination Therapy

In order to treat a subject having one of the conditions described herein (e.g., a subject that has already been diagnosed as having one of the conditions described herein), BCG may be administered to the subject in conjunction with another therapeutic agent. For instance, a subject that has an elevated level of serum cholesterol, LDLs, and/or triglycerides, and/or that is in need of an increase in serum HDL levels, may be administered a hypolipidemic agent in addition to BCG. This can be performed by admixing BCG together with a hypolipidemic agent or by administering an effective amount of BCG separately from the hypolipidemic agent. Exemplary hypolipidemic agents for use with the methods of the invention include HMG-CoA reductase inhibitors, niacin, fibric acid derivatives, cholesterol absorption inhibitors, and lipolytic agents. For instance, a HMG-CoA reductase inhibitors that may be admixed with or administered separately from BCG in order to treat a subject with elevated levels of cholesterol, LDLs, and/or triglycerides, and/or that is in need of an increase in the level of serum HDLs, include atorvastatin, cerivastatin, fluvastatin, lovastatin, mevastatin, pitavastatin, pravastatin, rosuvastatin, simvastatin, and combinations thereof. Examples of fibric acid derivatives that can be admixed with or administered separately from BCG and administered to a subject according to the methods of the invention include fenofibrate and gemfibrozil. Additionally, ezetimibe ((3R,4S)-1-(4-fluorophenyl)-3-[(3S)-3-(4-fluorophenyl)-3-hydroxypropyl]-4-(4-hydroxyphenyl)azetidin-2-one) is a fibric acid derivative that can be admixed with or administered separately from BCG to modulate serum lipid levels (e.g., to reduce serum cholesterol, LDL, and/or triglyceride levels, and/or to increase serum HDL levels) in a subject according to the methods of the invention. Exemplary lipolytic agents that can be admixed with or administered separately from BCG to modulate serum lipid levels in a subject include norepinephrine, isoproterenol, forskolin, bucladesine, and theophylline.

In addition to agents that directly regulate lipid metabolism, other agents that can synergize with BCG in the treatment of a subject having elevated serum cholesterol, LDL, and/or triglyceride levels, and/or that is in need of an increase in serum HDL levels, include TNFR2 agonists, such as TNFα. These agents are capable of potentiating the proliferation of various cells, such as T-reg cells, and can be administered in conjunction with BCG to a subject in order to reduce serum cholesterol, LDLs, and/or triglycerides, and/or to elevate serum HDLs. Additional agents that can be admixed, conjugated, or administered with, or administered separately from BCG to stimulate TNFR2 activity include e.g., IL-2, TNFα, as well as agonistic TNFR2 antibodies (see, e.g., WO 2014/124134, the disclosure of which is incorporated herein by reference).

Additionally, BCG may be admixed with or administered separately from an immunotherapy agent in order to reduce serum cholesterol, LDLs, and/or triglycerides, and/or to elevate serum HDLs. Exemplary immunotherapy agents include antibodies, fragments thereof, and other proteins capable of binding a particular epitope or target molecule. Exemplary immunotherapy agents useful in conjunction with the compositions and methods of the invention include an anti-CTLA-4 agent, an anti-PD-1 agent, an anti-PD-L1 agent, an anti-PD-L2 agent, a TNFα cross-linking agent, a TRAIL cross-linking agent, a CD27 agent, a CD30 agent, a CD40 agent, a 4-1BB agent, a GITR agent, an OX40 agent, a TRAILR1 agent, a TRAILR2 agent, a TWEAKR agent, and, e.g., agents directed toward the immunological targets described in Table 1 of Mahoney et al., Cancer Immunotherapy, 14:561-584 (2015), the disclosure of which is incorporated herein by reference. For example, immunological target 4-1BB ligand may be targeted with an anti-4-1BB ligand antibody; immunological target OX40L may be targeted with an anti-OX40L antibody; immunological target GITR may be targeted with an anti-GITR antibody; immunological target CD27 may be targeted with an anti-CD27 antibody; immunological target TL1A may be targeted with an anti-TL1A antibody; immunological target CD40L may be targeted with an anti-CD40L antibody; immunological target LIGHT may be targeted with an anti-LIGHT antibody; immunological target BTLA may be targeted with an anti-BTLA antibody; immunological target LAGS may be targeted with an anti-LAG3 antibody; immunological target TIM3 may be targeted with an anti-TIM3 antibody; immunological target Singlecs may be targeted with an anti-Singlecs antibody; immunological target ICOS ligand may be targeted with an anti-ICOS ligand antibody; immunological target B7-H3 may be targeted with an anti-B7-H3 antibody; immunological target B7-H4 may be targeted with an anti-B7-H4 antibody; immunological target VISTA may be targeted with an anti-VISTA antibody; immunological target TMIGD2 may be targeted with an anti-TMIGD2 antibody; immunological target BTNL2 may be targeted with an anti-BTNL2 antibody; immunological target CD48 may be targeted with an anti-CD48 antibody; immunological target KIR may be targeted with an anti-KIR antibody; immunological target LIR may be targeted with an anti-LIR antibody; immunological target ILT may be targeted with an anti-ILT antibody; immunological target NKG2D may be targeted with an anti-NKG2D antibody; immunological target NKG2A may be targeted with an anti-NKG2A antibody; immunological target MICA may be targeted with an anti-MICA antibody; immunological target MICB may be targeted with an anti-MICB antibody; immunological target CD244 may be targeted with an anti-CD244 antibody; immunological target CSF1R may be targeted with an anti-CSF1R antibody; immunological target IDO may be targeted with an anti-IDO antibody; immunological target TGFβ may be targeted with an anti-TGFβ antibody; immunological target CD39 may be targeted with an anti-CD39 antibody; immunological target CD73 may be targeted with an anti-CD73 antibody; immunological target CXCR4 may be targeted with an anti-CXCR4 antibody; immunological target CXCL12 may be targeted with an anti-CXCL12 antibody; immunological target SIRPA may be targeted with an anti-SIRPA antibody; immunological target CD47 may be targeted with an anti-CD47 antibody; immunological target VEGF may be targeted with an anti-VEGF antibody; and immunological target neuropilin may be targeted with an anti-neuropilin antibody (see, e.g., Table 1 of Mahoney et al.)

Immunotherapy agents described herein may be expressed recombinantly, e.g., from cultured cells (such as mammalian cells, e.g., CHO cells or HEK293 cells), or bacterial cells, such as *E. coli*. Immunotherapy agents can be expressed using standard recombinant DNA techniques known in the art, e.g., by transfecting a population of cultured cells with a plasmid containing one or more genes encoding an immunotherapy agent operably linked to a regulatory sequence known in the art, such as a promoter or enhancer capable of directing transcription of the gene of interest. Suitable vectors for the transfection of eukaryotic and prokaryotic cells are known in the art. Immunotherapy agents may optionally be produced as fusion proteins containing more than one therapeutic or biologically active moiety chemically bound together, e.g., by a linker known in the art or described herein.

Pharmaceutical Compositions

Therapeutic compositions containing BCG can be prepared, e.g., using methods known in the art or described herein. For instance, BCG formulations can be prepared using physiologically acceptable carriers, excipients, and/or stabilizers (*Remington's Pharmaceutical Sciences* 16th edition, Osol, A. Ed. (1980); the disclosure of which is incorporated herein by reference), and in a desired form, e.g., in the form of aqueous solutions or suspensions. The compositions can also be prepared so as to contain BCG at a desired concentration or cell count. BCG compositions of the invention also include lyophilized compositions that can be rehydrated prior to administration. The sections that follow describe useful additives that can be included in a BCG formulation for administration to a subject or for long-term storage.

Cryopreserved Formulations of BCG

Pharmaceutical compositions of BCG can be prepared for storage by cryopreservation, e.g., by contacting BCG with a cryoprotectant known in the art, such as dimethylsulfoxide (DMSO). Suitable DMSO concentrations in BCG stock solutions range from 0.01% to about 1% DMSO. Cryopreserved solutions can include acceptable carriers, excipients or stabilizers typically employed in the art, e.g., buffering agents, stabilizing agents, preservatives, isotonifiers, non-ionic detergents, antioxidants, and other miscellaneous additives. See, e.g., *Remington's Pharmaceutical Sciences*, 16th edition (Osol, ed. 1980; incorporated herein by reference). Such additives are generally nontoxic to the subject that is ultimately treated at the dosages and concentrations employed.

Buffering Agents

A wide array of buffering agents can be included in a BCG formulation useful in conjunction with the methods of the invention. These substances serve to maintain the pH of the formulation in a desirable range, e.g., a range that approximates physiological conditions. Buffering agents can be present at concentration ranging from, e.g., about 2 mM to about 50 mM. Suitable buffering agents for use with BCG formulations include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives

Preservatives can be added to a formulation of BCG and, optionally, an additional therapeutic agent, in order to retard the growth of other potential microbes in the pharmaceutical composition. For instance, preservatives can be present in a BCG-containing formulation in a wide range of concentrations, e.g., ranging from 0.02%-1% (w/v). Suitable preservatives for use in a pharmaceutical composition of the invention include phenol, benzyl alcohol, meta-cresol, methyl paraben, propyl paraben, octadecyldimethylbenzyl ammonium chloride, benzalconium halides {e.g., chloride, bromide, and iodide), hexamethonium chloride, and alkyl parabens such as methyl or propyl paraben, catechol, resorcinol, cyclohexanol, and 3-pentanol. Isotonicifiers can be added to ensure isotonicity of BCG formulations and include polhydric sugar alcohols, for example trihydric or higher sugar alcohols, such as glycerin, arabitol, xylitol, sorbitol and mannitol.

BCG formulations useful in conjunction with the methods of the invention may include stabilizers. Stabilizers represent a broad category of excipients which can range in function from a bulking agent to an additive which solubilizes an additional therapeutic agent or helps to prevent denaturation or adherence of the therapeutic agent to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. Stabilizers can be present in a BCG formulation in a wide range of concentrations, e.g., from 0.001% to 10.0% (w/w).

Detergents

Non-ionic surfactants or detergents (also known as "wetting agents") can be added to help solubilize the therapeutic agent (e.g., an additional therapeutic agent co-formulated with BCG) as well as to protect the therapeutic agent against agitation-induced aggregation, which also permits the formulation to be exposed to shear surface stressed without causing denaturation of a therapeutic protein (e.g., an immunotherapy agent). Suitable non-ionic surfactants that can be added to a formulation containing BCG and, optionally, an additional therapeutic agent include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/mL to about 1.0 mg/mL, for example about 0.07 mg/mL to about 0.2 mg/mL. Additional miscellaneous excipients that can be added to a formulation containing BCG and, optionally, an additional therapeutic agent include bulking agents (e.g., starch), chelating agents (e.g., EDTA), antioxidants (e.g., ascorbic acid, methionine, vitamin E), and cosolvents.

Other Pharmaceutical Carriers

Alternative pharmaceutically acceptable carriers that can be incorporated into a BCG formulation may include dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methyl hydroxy benzoate, propylhydroxy benzoate, talc, magnesium stearate, and mineral oils. A composition containing BCG may further include a lubricant, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

Blood-brain barrier penetration

In certain embodiments, therapeutic agents described herein can be formulated to ensure proper distribution in vivo. For example, the blood-brain barrier (BBB) excludes many high-molecular weight compounds, as well as those with elevated hydrophilicity. To ensure that the therapeutic agents useful with the methods of the invention cross the BBB (if desired), they can be formulated, for example, in liposomes. Methods of manufacturing liposomes have been described, e.g., U.S. Pat. Nos. 4,522,811; 5,374,548; and 5,399,331. The liposomes may comprise one or more moieties that are selectively transported into specific cells or organs, thereby enhancing targeted drug delivery (see, e.g., V. V. Ranade, J. Clin. Pharmacol. 29:685, 1989)). Exemplary targeting moieties include, e.g., folate or biotin (see, e.g., U.S. Pat. No. 5,416,016); mannosides (Umezawa et al. (Biochem. Biophys. Res. Commun. 153:1038, 1988)); antibodies (P. G. Bloeman et al. (FEBS Lett. 357:140, 1995); M. Owais et al. (Antimicrob. Agents Chemother. 39:180, 1995)); and surfactant protein A receptor (Briscoe et al. (Am. J. Physiol. 1233:134, 1995)); the disclosures of each of which are incorporated herein by reference.

Routes of Administration and Dosing

Unit Dosage Forms

Desirably, the methods of the invention include administering BCG to a subject in a unit dosage form that contains a low quantity of BCG that is capable of inducing a therapeutic response (e.g., lowering serum cholesterol, LDL, and/or triglyceride levels, increasing serum HDL levels, and/or lowering blood glucose levels). A BCG formulation useful in conjunction with the methods of the invention may contain, e.g., between $1 \times 10^4$ and $1 \times 10^9$ cfu per 0.1 milligrams of BCG (e.g., $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $8 \times 10^8$, $5 \times 10^8$, $6 \times 10^8$, $7 \times 10^8$, $8 \times 10^8$, $9 \times 10^8$, or $1 \times 10^9$ cfu per 0.1 milligrams of BCG.

In preferred embodiments, BCG is administered to a subject in a unit dosage form containing between about $5 \times 10^5$ and about $1 \times 10^7$ cfu per 0.1 milligrams of BCG. For instance, preferred unit dosage forms of BCG useful in conjunction with the methods of the invention contain $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, or $1 \times 10^7$ cfu per 0.1 milligrams of BCG. In particularly preferred embodiments, BCG is administered to a subject in a unit dosage form containing between about $1 \times 10^6$ and $6 \times 10^6$ cfu per 0.1 milligrams of BCG. Desirably, unit dosage forms useful with the methods of the invention may contain about $3.9 \times 10^6$ cfu per 0.1 milligrams of BCG.

BCG can be used in conjunction with the compositions and methods of the invention, as well as any other form of *Mycobacterium*. Exemplary mycobacteria useful in conjunction with the compositions and methods of the invention include substrains of BCG. Substrains of BCG include those that can be cultured under good manufacturing protocols, such as the Pasteur, Japan-Tokyo, Pasteur, Copenhagen, TICE, Sanofi, Connaught, RIVM, Evans, MMC, and Glaxo substrains of BCG, as well as attenuated and genetically modified versions of these strains. Mycobacteria for use with the compositions and methods of the invention may be live, attenuated, or inactivated such that the bacteria retain certain antigen expression patterns but are no longer virulent.

Re-Dosing Based on Diagnostic Methods of the Invention

In various cases, it may be desirable to administer BCG to a subject multiple times (e.g., between 2 and 20 times, such as 2, 3, 4, 5, 6, 7, 8, 9, or 10 times) based on the response of a subject to BCG therapy. For instance, a subject may be administered BCG according to the methods of the invention in order to reduce serum cholesterol levels or to treat one or more of the diseases described herein. After a period of time following this initial administration (e.g., one or more days, weeks, months, or years), the subject may be re-evaluated in order to determine the continued effectiveness of the initial BCG administration on the disease or conditions being treated. For example, a subject that is administered BCG or another therapeutic agent in order to reduce serum cholesterol levels may be examined using one or more analytical tests (such as those described herein) in order to assess the responsiveness of the subject to administration of BCG or another therapeutic agent and/or to determine if the subject would benefit from additional doses of BCG or another medicament. The subject may be administered BCG or another therapeutic agent and may subsequently have a blood sample withdrawn in order to determine if the methylation state of one or more cytosine residues in the nuclear DNA within a cell of the subject has changed in response to administration of BCG or another therapeutic agent. For instance, a physician of skill in the art can withdraw a blood sample from a subject having previously been administered BCG or another therapeutic agent and may analyze the nuclear DNA within a cell of the sample (e.g., within a T-lymphocyte of the sample, such as a CD4+, CD25+ T-reg cell) to determine if one or more cytosine residues has been methylated or demethylated in response to treatment with BCG or another therapeutic agent. Preferably, the one or more cytosine residues are located within a gene that encodes a transcription factor, such as FoxP3, or within a gene that encodes CD45. A determination that the quantity of methylated cytosine residues in one or more of both of these genetic loci has decreased indicates that the patient is responding to treatment with BCG or another therapeutic agent and may not require subsequent doses. For instance, a determination that one or more particular cytosine residues within the FoxP3 and/or CD45 genes that was previously methylated in the subject prior to treatment with BCG or another therapeutic agent treatment and has since undergone demethylation indicates that the subject is responding to the therapy and may not require subsequent doses of BCG or another medicament.

In contrast, a determination that the quantity of methylated cytosine residues in one or both of these genetic loci has stayed the same or increased indicates that the subject would likely benefit from one or more additional doses of BCG or another therapeutic agent. For example, a determination that one or more particular cytosine residues within the FoxP3 and/or CD45 genes that was previously methylated in the subject prior to treatment with BCG or another therapeutic agent and remains methylated following administration of BCG or another therapeutic agent indicates that the subject would likely benefit from one or more subsequent doses of BCG or another therapeutic agent. Alternatively, a determination that that one or more particular cytosine residues within the FoxP3 and/or CD45 genes that was previously demethylated in the subject prior to administration of BCG or another therapeutic agent and has since undergone methylation following administration of BCG or another therapeutic agent indicates that the subject would likely benefit from one or more subsequent doses of BCG or another therapeutic agent.

In addition to analysis of cytosine methylation state, one of skill in the art may examine the level of one or more mRNA molecules, proteins, acetylated amino acids, and/or methylated metabolites in a sample isolated from a subject having previously been administered BCG or another therapeutic agent in order to determine if the subject is responding to the therapy or if he/she would benefit from receiving additional doses of BCG or another medicament. For instance, according to the methods of the invention, one of skill in the art may determine the level of one or more mRNA molecules encoding a cytokine or lipolytic protein in order to assess whether a subject previously administered BCG or another therapeutic agent would likely benefit from receiving additional doses. A determination that the level of one or more mRNA molecules encoding a cytokine (e.g., IL-6, TNFα, or IFNγ) or a lipolytic protein (e.g., acyl co-enzyme A oxidase, carnitine palmitoyltransferase, lipase, or uncoupling protein) in a sample isolated from a subject that has been previously administered BCG or another therapeutic agent is about the same as or is less than the level of the same mRNA molecules in a sample previously isolated from the subject (e.g., between about 24 hours and about 5 years prior to the subject having been administered BCG or another therapeutic agent, preferably between about 24 hours and about 5 years prior to administration of BCG or the other therapeutic agent, and desirably between about 1 month and 1 year prior to the subject having been administered BCG or the other therapeutic agent) indicates that the subject would likely benefit from receiving one or more additional doses of BCG or another therapeutic agent.

Alternatively, one of skill in the art may determine the level of one or more mRNA molecules encoding a lipogenic protein, an adiponectin receptor, a lysine acetyltransferase (KAT), a histone acetyltransferase, a histone deacetylase (HDAC), or a histone in order to assess whether a subject previously administered BCG or another therapeutic agent would likely benefit from receiving additional doses of BCG or the previously administered therapeutic agent (in particular, BCG). A determination that the level of one or more mRNA molecules encoding a lipogenic protein (e.g., acetyl co-enzyme A carboxylase α, acetyl co-enzyme A carboxylase β, fatty acid synthase, glyceraldehydes-6-phosphate dehydrogenase, stearoyl-CoA saturase, malic enzyme, or glucose-6-phosphate dehydrogenase), adiponectin receptor (e.g., adiponectin receptor 1 or adiponectin receptor 2), lysine acetyltransferase (e.g., KAT2A, KAT2B, KAT5, KAT6A, KAT6B, KAT7, or KAT8), histone acetyltransferase, histone deacetylase (e.g., HDAC1, HDAC2, HDAC3, HDAC4, HDAC5, HDAC6, HDAC7, HDAC8, HDAC9, HDAC10, HDAC11, HDAC1P1, HDAC1P2, SIRT1, SIRT2, SIRT3, SIRT4, SIRT5, SIRT6, or SIRT7), or histone (e.g., H2A, H2B, H3, or H4) in a sample isolated from a subject that has been previously administered BCG or another therapeutic agent is about the same as or is greater than the level of the same mRNA molecules in a sample previously isolated from the subject (e.g., between about 24 hours and about 5 years prior to the subject having been administered BCG or another therapeutic agent, preferably between about 24 hours and about 5 years prior to administration of BCG or the other therapeutic agent, and desirably between about 1 month and 1 year prior to the subject having been administered BCG or the other therapeutic agent) indicates that the subject would likely benefit from receiving one or more additional doses of BCG or another therapeutic agent (preferably BCG).

The levels of mRNA molecules in a sample isolated from a subject (e.g., from one or more cells, such as T-lymphocytes, isolated from a subject) can be determined using methods known in the art, such as by Northern blot analysis or by standard quantitative reverse-transcription polymerase chain reaction (PCR) techniques.

Additionally or alternatively, one of skill in the art may determine the level of one or more proteins, such as a cytokine or lipolytic protein, in order to assess whether a subject previously administered BCG or another therapeutic agent would likely benefit from receiving additional doses. A determination that the level of the one or more cytokines (e.g., IL-6, TNFα, or IFNγ) or lipolytic proteins (e.g., acyl co-enzyme A oxidase, carnitine palmitoyltransferase, lipase, or uncoupling protein) in a sample isolated from a subject that has been previously administered BCG or another therapeutic agent is about the same as or is less than the level of the same proteins in a sample previously isolated from the subject (e.g., between about 24 hours and about 5 years prior to the subject having been administered BCG or another therapeutic agent, preferably between about 24 hours and about 5 years prior to BCG or another therapeutic agent administration, and desirably between about 1 month and 1 year prior to the subject having been administered BCG or another therapeutic agent) indicates that the subject would likely benefit from receiving one or more additional doses of BCG or another therapeutic agent.

Alternatively, one of skill in the art may determine the level of one or more different proteins, such as a lipogenic protein, an adiponectin receptor, a lysine acetyltransferase (KAT), a histone acetyltransferase, a histone deacetylase (HDAC), or a histone in order to assess whether a subject previously administered BCG or another therapeutic agent would likely benefit from receiving additional doses of BCG or the previously administered therapeutic agent (in particular, BCG). A determination that the level of one or more lipogenic proteins (e.g., acetyl co-enzyme A carboxylase α, acetyl co-enzyme A carboxylase β, fatty acid synthase, glyceraldehydes-6-phosphate dehydrogenase, stearoyl-CoA saturase, malic enzyme, or glucose-6-phosphate dehydrogenase), adiponectin receptors (e.g., adiponectin receptor 1 or adiponectin receptor 2), lysine acetyltransferases (e.g., KAT2A, KAT2B, KAT5, KAT6A, KAT6B, KAT7, or KAT8), histone acetyltransferases, histone deacetylases (e.g., HDAC1, HDAC2, HDAC3, HDAC4, HDAC5, HDAC6, HDAC7, HDAC8, HDAC9, HDAC10, HDAC11, HDAC1P1, HDAC1P2, SIRT1, SIRT2, SIRT3, SIRT4, SIRT5, SIRT6, or SIRT7), or histones (e.g., H2A, H2B, H3, or H4) in a sample isolated from a subject that has been previously administered BCG or another therapeutic agent is about the same as or is greater than the level of the same proteins a sample previously isolated from the subject (e.g., between about 24 hours and about 5 years prior to the subject having been administered BCG or another therapeutic agent, preferably between about 24 hours and about 5 years prior to treatment with BCG or another therapeutic agent, and desirably between about 1 month and 1 year prior to the subject having been administered BCG or the other therapeutic agent) indicates that the subject would likely benefit from receiving one or more additional doses of BCG or another therapeutic agent (preferably BCG).

The levels of the proteins described herein can be monitored using standard techniques know in the art, such as by solution phase ELISA assays or by immunoblot assays, such as Western blot experiments known in the field.

In addition to monitoring mRNA and protein levels to assess the likelihood that a subject would benefit from one or more subsequent doses of BCG or another therapeutic agent, one of skill in the art can also monitor the level of one or more acetylated amino acids or methylated metabolites in order to make this determination. For instance, one of skill in the art can monitor the level of one or more acetylated amino acids, such as n-acetylalanine, N-acetylaspartic acid, N-acetylserine, N-acetylthreonine, N-acetylhistidine, N-acetyl-3-methylhistidine, N-acetylvaline, and N-α-acetyllysine, or N-acetylmethionine, in a sample isolated from a subject that has previously been administered BCG or another therapeutic agent. Additionally or alternatively, one of skill in the art may determine the level of one or more methylated metabolites, such as N-α-acetyl-3-methylhistidine, 3-methylglutaconic acid, 3-methylglutarylcarnitine, or N-ε-trimethyllysine, in a sample isolated from the subject. A determination that the level of one or more of these acetylated amino acids and/or methylated metabolites in the sample isolated from the subject is about the same as or less than the levels of the same acetylated amino acids and/or methylated metabolites in a sample previously isolated from the subject (e.g., between about 24 hours and about 5 years prior to the subject having been administered BCG or another therapeutic agent, preferably between about 24 hours and about 5 years prior to BCG or another therapeutic agent administration, and desirably between about 1 month and 1 year prior to the subject having been administered BCG or the other therapeutic agent) indicates that the subject would likely benefit from receiving one or more additional doses of BCG or another therapeutic agent.

Additionally or alternatively, one of skill in the art can monitor the level of one or more different methylated metabolites in order to assess the likelihood of the subject to benefit from additional doses of BCG or another therapeutic agent. For instance, one of skill in the art can monitor the level of one or both of 4-methyl-2-oxopentanoic acid and 3-methyl-2-oxobutyric acid in a sample isolated from a subject that has previously been administered BCG or another therapeutic agent. A determination that the level of one or more of these methylated metabolites in the sample isolated from the subject is about the same as or less than the levels of the same methylated metabolites in a sample previously isolated from the subject (e.g., between about 24 hours and about 5 years prior to the subject having been administered BCG or another therapeutic agent, preferably between about 24 hours and about 5 years prior to treatment with BCG or another therapeutic agent administration, and desirably between about 1 month and 1 year prior to the subject having been administered BCG or the other therapeutic agent) indicates that the subject would likely benefit from receiving one or more additional doses of BCG or another therapeutic agent. The levels of acetylated amino acids and methylated metabolites described herein can be determined quantitatively using established techniques known in the art, including by the use of nuclear magnetic resonance (NMR), high-performance liquid chromatography (HPLC), mass-spectrometry (MS), UV-Vis spectroscopy, among others.

Upon determining that a subject would likely benefit from one or more additional doses of BCG or another therapeutic agent, a physician of skill in the art can administer treatment to the subject, e.g., one or more doses of BCG. Using the methods of the invention, a physician may administer, e.g., between one and 20 total doses of BCG, or more, to the subject over the course of treatment. For instance, a physician may administer an initial dose of BCG to the subject and, following the genomic, proteomic, or metabolomic analyses described herein, the subject may subsequently be administered one or more additional doses of BCG a certain time after receiving the initial dose. The time that passes between the initial dose and any subsequent doses may vary depending on the patient and the conditions being treated. For example, a patient may receive an initial dose of BCG and, after a physician assesses the subject using, e.g., one or more of the diagnostic biomarkers described herein, and concludes that the subject would likely benefit from one or more subsequent doses of BCG, the subject may then be administered additional doses of BCG, e.g., between about 1 week and about 20 years following the initial dose. For instance, a patient may be administered one or more doses of BCG about once every 1-10 years, such as about once every 5 years. In preferred embodiments, the subject receives a total of two doses of BCG: an initial dose and a follow-on dose after a physician makes the determination that the subject would likely benefit from the additional administration.

As an alternative to receiving another dose of BCG, the subject can instead be administered another therapeutic agent, depending on the disease being treated. If the patient is being treated for elevated serum cholesterol, LDL, or triglyceride levels, and/or for reduced HDL levels, the patient may be administered, e.g., a hypolipidemic agent, such as those described herein or known in the art. If the patient is being treated for an immunological, neurological, or metabolic disorder (e.g., an autoimmune disease, a neurological condition, an allergy, allograft rejection, graft-versus-host disease, asthma, macular degeneration, muscular atrophy, a disease related to miscarriage, atherosclerosis, bone loss, a musculoskeletal disease, and obesity), the patient may be administered a TNFR2 agonist as a subsequent therapeutic agent, e.g., in order to stimulate the proliferation of different cell populations, such as T-reg cells. Additionally or alternatively, a patient being treated for one or more of these conditions may receive as a subsequent medicament an immunotherapy agent, such as an anti-CTLA-4 agent, an anti-PD-1 agent, an anti-PD-L1 agent, an anti-PD-L2 agent, a TNFα cross-linking agent, a TRAIL cross-linking agent, a CD27 agent, a CD30 agent, a CD40 agent, a 4-1BB agent, a GITR agent, an OX40 agent, a TRAILR1 agent, a TRAILR2 agent, or a TWEAKR agent.

Routes of Administration

According to the methods of the invention, BCG can be administered to a subject (e.g., a mammalian subject, such as a human) by a variety of routes. Using the methods of the invention, BCG is preferably administered to a subject intradermally, subcutaneously, orally, transdermally, intranasally, intravenously, intramuscularly, intraocularly, parenterally, intrathecally, or intracerebroventricularly (e.g., intradermally or subcutaneously). In some embodiments, BCG is not administered to the subject (e.g., a human subject) intravenously. The most suitable route for administration in any given case will depend on the nature and severity of the particular disease being treated, the patient, pharmaceutical formulation methods, the patient's age, body weight, sex, the patient's diet, and the patient's excretion rate.

Therapeutic formulations of BCG can be administered with medical devices known in the art. For example, a therapeutic formulation of BCG can be administered with a needleless hypodermic injection device, such as the devices disclosed in U.S. Pat. Nos. 5,399,163; 5,383,851; 5,312,335; 5,064,413; 4,941,880; 4,790,824; or 4,596,556; the disclosures of each of which are incorporated herein by reference. Examples of well-known implants and modules useful in the invention include those described in U.S. Pat. No. 4,487,603; which discloses an implantable micro-infusion pump for dispensing medication at a controlled rate; U.S. Pat. No. 4,486,194; which discloses a therapeutic device for administering medicaments through the skin; U.S. Pat. No. 4,447,233; which discloses a medication infusion pump for delivering medication at a precise infusion rate; U.S. Pat. No. 4,447,224; which discloses a variable flow implantable infusion apparatus for continuous drug delivery; U.S. Pat. No. 4,439,196; which discloses an osmotic drug delivery system having multi-chamber compartments; and U.S. Pat. No. 4,475,196; which discloses an osmotic drug delivery system. These patents are incorporated herein by reference. Many other such implants, delivery systems, and modules are known to those skilled in the art.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventor regards as her invention.

Example 1

Administration of BCG Promotes Sustained Decrease in Serum Lipids

Figure 2:
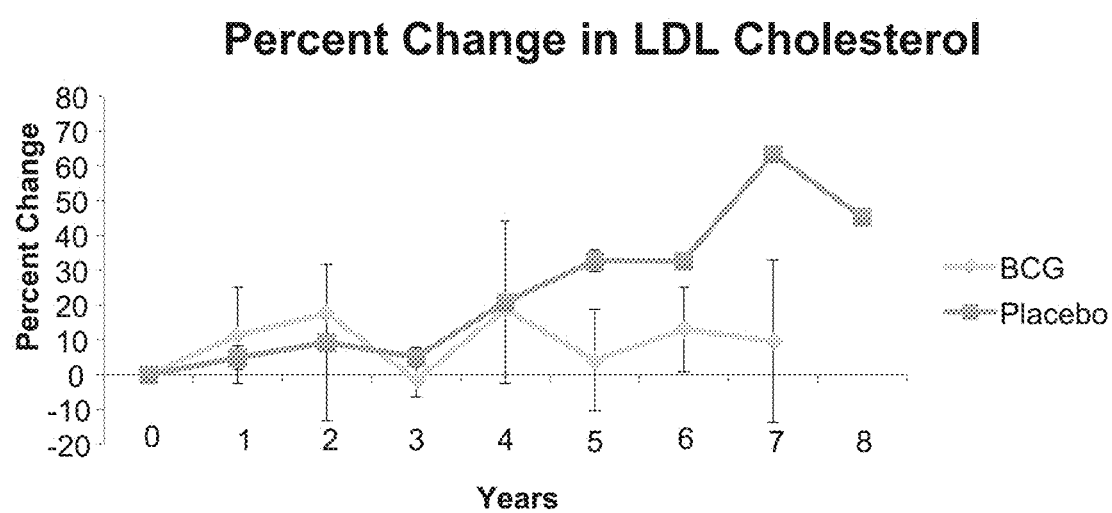
FIG. 2 is a graph showing the effect of BCG treatment on serum LDL concentrations over the course of a multi-year study. The chart plots the percent change in LDL level as a function of time, in years, following administration of either BCG or a placebo (control) to a group of patients presenting with high cholesterol levels. The data demonstrate the ability of BCG to promote a sustained reduction in LDL levels, as patients that were administered BCG generally exhibited an increase in LDL levels of 10% or less over the duration of the study, while patients that were administered a placebo typically exhibited an increase in LDL levels of between 10% and 60%.
Figure 3:
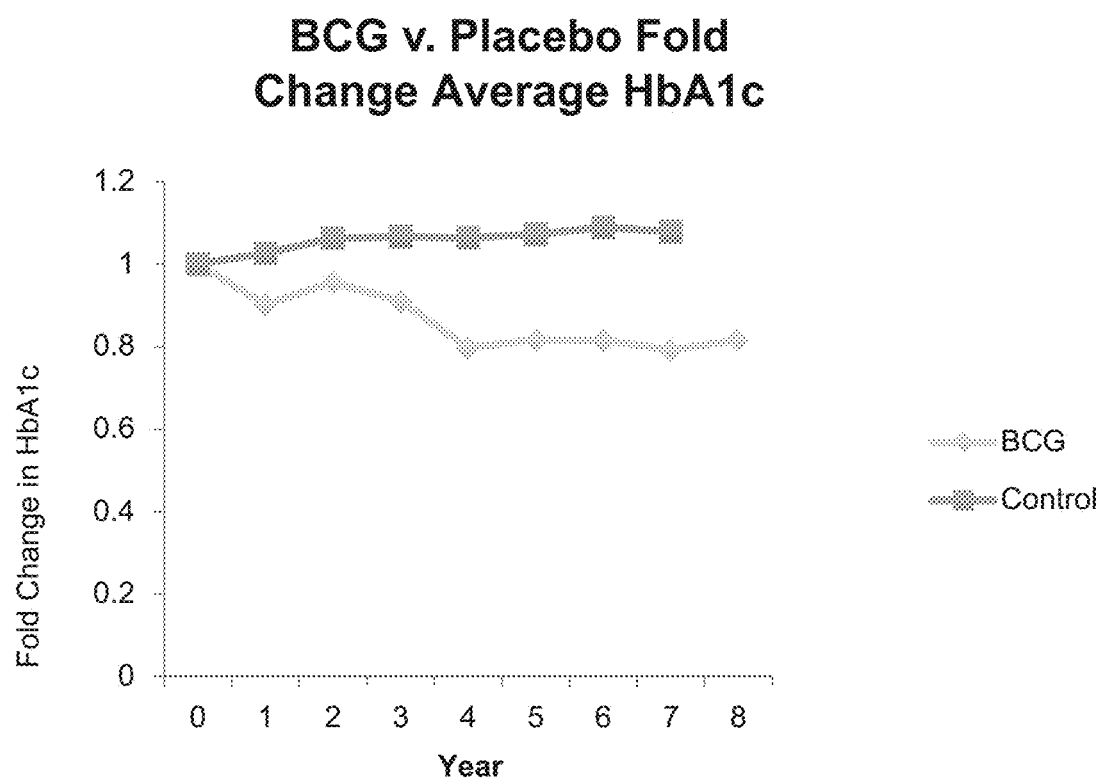
FIG. 3 is a graph showing the ability of BCG to induce a reduction in average glycated hemoglobin (HbA1c) levels in patients presenting with high serum cholesterol over the course of a multi-year investigation. The chart plots the fold change in HbA1c as a function of time, in years, following administration of either BCG or a placebo (control) to a group of patients presenting with high serum cholesterol. The readout, HbA1c level, is an indicator of total blood glucose concentration and can therefore be used to detect patients at risk of developing type I diabetes. The data demonstrate that patients administered BCG exhibited an average decrease in HbA1c levels of between 10% and 30% over the course of the study. Moreover, this reduction was generally sustained over the eight-year measurement period. Taken together, the data provided in FIGS. 1-3 demonstrate the ability of BCG to lower cholesterol and HDL levels and to promote a long-term reduction in blood glucose concentrations.

BCG can be administered to a subject, such as a subject (e.g., a human) that has previously been diagnosed as having elevated levels of serum cholesterol, LDLs, and/or triglycerides in order to reduce the concentrations of one or more of these lipids and restore healthy lipid metabolism in the subject. As shown in FIG. 1, administration of BCG to a group of subjects with elevated cholesterol promoted a decrease in serum cholesterol relative to subjects treated with a placebo instead of BCG. Moreover, the data in FIG. 1 demonstrates that the decrease in serum cholesterol was sustained over the course of up to 7 years following administration of BCG. Likewise, the data shown in FIG. 2 demonstrate that BCG is similarly capable of attenuating serum LDL levels over a prolonged period of time. FIG. 3 shows that BCG is additionally capable of reducing serum levels of glycated hemoglobin, which serves as an indicator of serum glucose concentration and can often signal an aberration in glucose metabolism. Taken together, the data presented in FIGS. 1-3 demonstrate that BCG induces a prolonged attenuation in serum cholesterol, LDL, and HbA1c levels and represents a robust therapeutic regimen for treating these indications and diseases associated with elevated levels of these substances.

Example 2

Figure 4B:
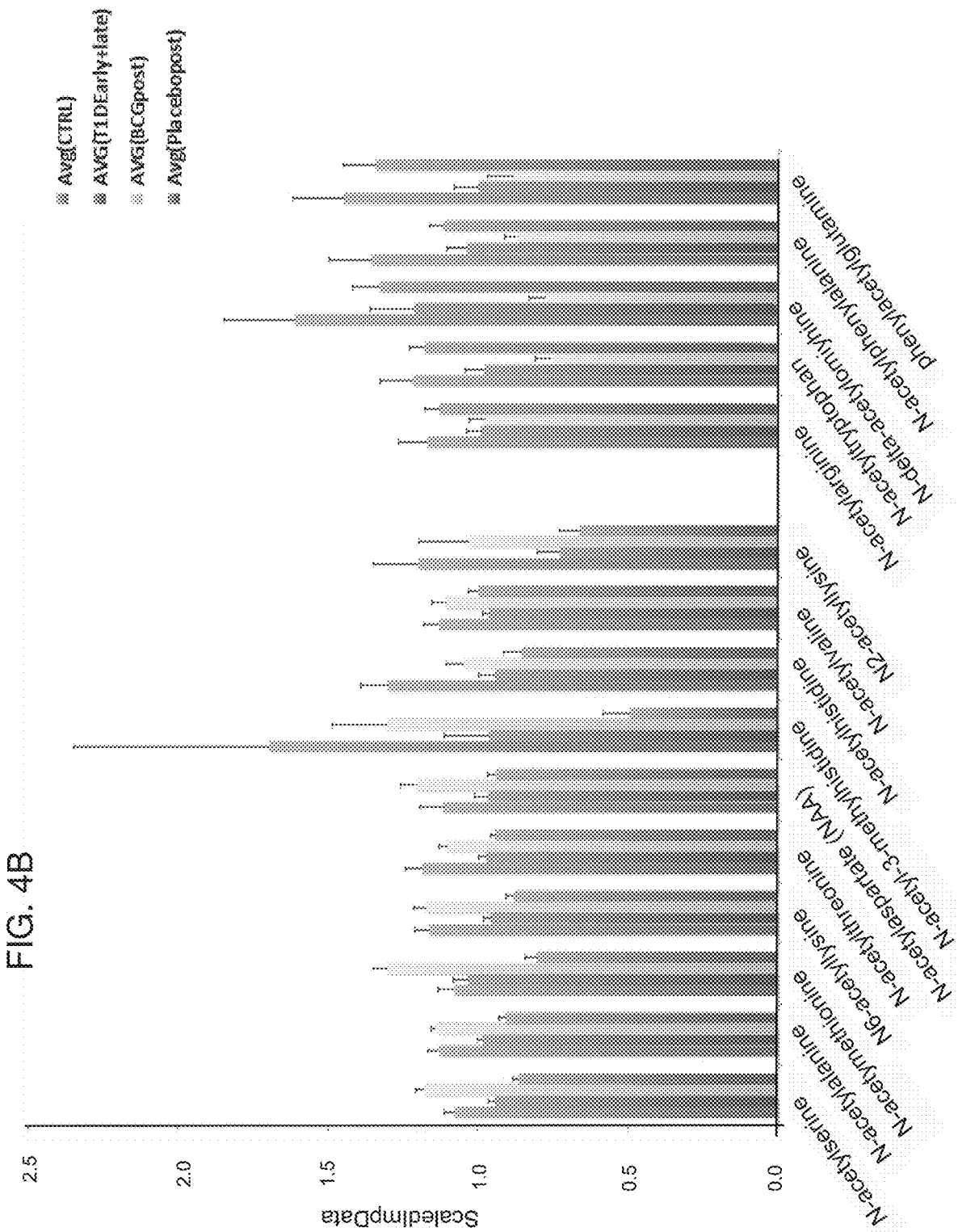
FIG. 4B is a graph showing the changes in N-acetylated amino acid concentrations listed in FIG. 4A. From left to right, vertical bars for each N-acetylated amino acid appear in the order of average among control subjects (Avg(CTRL)), average among type-1 diabetes subjects suffering from early or late onset of the disease (AVG (T1Dearly+late)), average following BCG treatment of type-1 diabetes subjects (AVG(BCGpost)), and average among placebo-treated subjects following administration of the placebo (Avg(Placebopost)). Taken together, these data demonstrate the ability of BCG to restore healthy levels of N-acetylated amino acids in patients with type I diabetes as opposed to patients treated with a placebo. As shown in each figure, BCG is capable of promoting an increase in the concentrations of N-acetylalanine, N-acetylaspartate, N-acetylserine, N-acetylthreonine, N-acetyl-3-methylhistidine, N-acetylhistidine, N-acetylvaline, Nα-acetyllysine, and N-acetylmethionine, which are depleted in patients suffering from type I diabetes. BCG induces a decrease in the concentrations of N-acetylphenylalanine, N-acetyltryptophan, and N-acetylarginine, which are elevated in patients with type I diabetes. Therefore, the changes promoted by BCG serve to restore N-acetylated amino acid concentrations to healthy levels in patients suffering from disease associated with lipid and/or cholesterol metabolism, such as type I diabetes.

Administration of BCG Restores Healthy Levels of N-Acetylated Amino Acids and Methylated Metabolites Administration of BCG to a subject suffering from elevated serum cholesterol, LDLs, and/or triglycerides, reduced levels of serum HDLs, and/or an immunological, neurological, or metabolic disease described herein is capable of regulating the levels of various acetylated amino acids and methylated metabolites. As shown in FIGS. 4A and 4B, a subject presenting with one or more of these diseases (e.g., type I diabetes) can be treated with BCG in order to increase the level of various N-acetylated amino acids, such as N-acetylalanine, N-acetylaspartic acid, N-acetylserine, N-acetylthreonine, N-acetylhistidine, N-acetyl-3-methylhistidine, N-acetylvaline, and N-α-acetyllysine, and N-acetylmethionine. BCG may promote an increase in one or more of these substances by inducing the acetylation of, e.g., alanine, aspartic acid, serine, threonine, histidine, 3-methylhistidine, valine, lysine, and/or methionine. As a result, one of skill in the art may use NMR spectroscopy to determine whether the quantity of the one or more acetylated amino acids listed above has increased, e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more, relative to the quantity of these substances in a reference sample, such as a sample isolated from a subject prior to administration of BCG.

Figure 5:
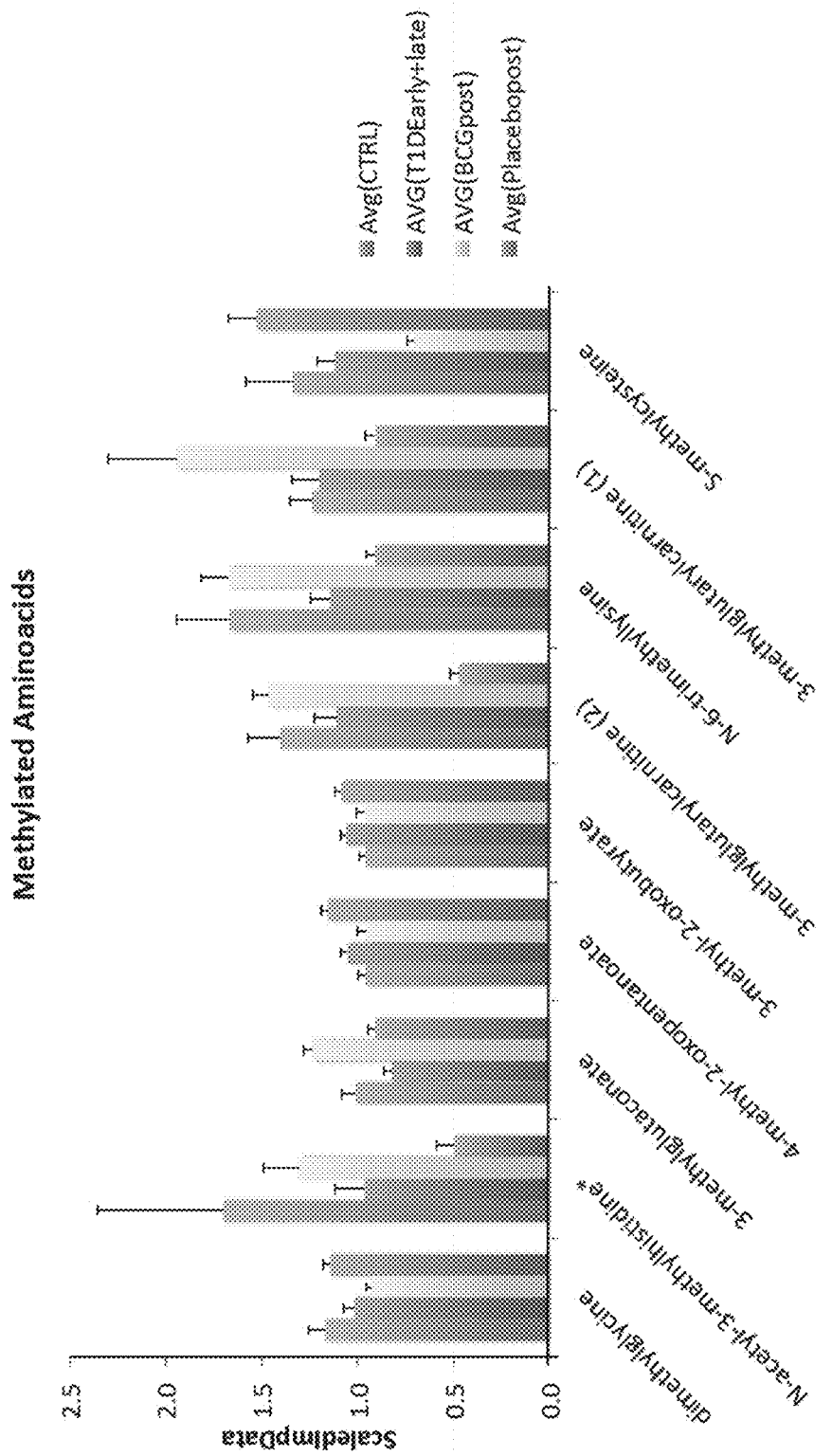
FIG. 5 is a graph showing the ability of BCG to restore healthy levels of methylated metabolites in patients with type I diabetes relative to patients treated with a placebo. The chart shows the average levels of various N-methylated metabolites amino acids in a group of patients following administration with either BCG ("Avg(BCGpost)") or placebo ("Avg(Placebopost)") relative to patients before receiving treatment of any kind ("AVG(T1Dearly+late)") and relative to control patients not suffering from type I diabetes ("Avg(CTRL)"). From left to right, vertical bars for each N-acetylated amino acid appear in the order of average among control subjects (Avg(CTRL)), average among type-1 diabetes subjects suffering from early or late onset of the disease (AVG(T1Dearly+late)), average following BCG treatment of type-1 diabetes subjects (AVG(BCGpost)), and average among placebo-treated subjects following administration of the placebo (Avg(Placebopost)). The data are shown as scaled levels such that all values are between 0 and 2.5. The data demonstrate that BCG is capable of promoting an increase in the concentrations of N-acetyl-3-methylhistidine, 3-methylglutaconate, 3-methylglutarylcarnitine, and Nε-trimethyllysine, which are depleted in patients suffering from type I diabetes. BCG induces a decrease in the concentrations of 4-methyl-2-oxopentanoate and 3-methyl-2-oxobutyrate, which are elevated in patients with type I diabetes. Therefore, the changes promoted by BCG serve to restore N-methylated metabolite concentrations to healthy levels.

As shown in FIG. 5, a subject presenting with a disease described above (e.g., type I diabetes) can additionally be administered BCG in order to regulate methylated metabolite levels. For instance, BCG can be administered to a subject in order to increase the levels of various methylated metabolites, such as N-α-acetyl-3-methylhistidine, 3-methylglutaconic acid, 3-methylglutarylcarnitine, and N-ε-trimethyllysine (e.g., by promoting the methylation of N-α-acetylhistidine, glutaconic acid, glutarylcarnitine, lysine, and cysteine), e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more, relative to the quantity of these substances in a reference sample, such as a sample isolated from a subject prior to administration of BCG. Additionally, BCG administration reduces the levels of certain methylated metabolites, such as 4-methyl-2-oxopentanoic acid and 3-methyl-2-oxobutyric acid (e.g., by promoting demethylation of these metabolites) e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more, such as about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more, relative to the quantity of these substances in a reference sample, such as a sample isolated from a subject prior to administration of BCG. The levels of these metabolites can be quantified using techniques known in the art, such as NMR spectroscopy, HPLC, MS, and other standard procedures.

The effect of BCG on protein expression is also manifested in the up-regulation and down-regulation of various enzymes and receptors involved in glucose and lipid metabolism upon administration of BCG to a subject. As the data in FIG. 6 shows, subjects suffering from type I diabetes that were administered BCG exhibited an increase in various cytokines (e.g., IL-6, TNFα, and IFNγ) as well as lipolytic factors (e.g., acyl co-enzyme A oxidase, carnitine palmitoyltransferase, lipase, and uncoupling protein). BCG also resulted in a marked decrease in various adiponectin receptors (e.g., adiponectin receptors 1 and 2) and lipogenic proteins (e.g., uncoupling protein, carnitine palmitoyl transferase A, B, and C, and acetyl-CoA carboxylase 1, 2, and 3). Thus, the levels of these biomarkers can be assessed to determine (1) whether a patient is responsive to BCG treatment, and (2) whether administration of one or more subsequent doses of BCG is necessary to achieve a therapeutic effect (e.g., to restore the serum concentration of cholesterol, LDLs, HDLs, triglycerides, and/or HbA1c to a healthy level in a patient).

Example 3

Diagnosing a Patient Presenting with or Prone to Elevated Cholesterol as Likely to Respond to BCG Therapy A physician of skill in the art can determine whether a patient (e.g., a patient that has already been diagnosed as having a particular disease, such as elevated cholesterol, LDLs, or triglycerides, reduced HDL levels, a disease associated with these altered serum lipid levels, or an immunological, neurological, or metabolic disease described herein) is likely to respond to BCG therapy by determining the quantity of methylated cytosine residues in a sample isolated from the subject and comparing this quantity to the amount of methylated cytosine residues in the DNA sequence of the same genetic locus in a reference sample. The reference sample may be a sample isolated from a healthy patient, optionally of the same age, sex, and/or weight, or the reference sample may be a standard quantity of methylated cytosine residues in a particular DNA sequence that is generally associated with a healthy physiological state or observed in healthy subjects, such as between 1 and 100 methylated cytosine residues (e.g., between 1 and 50 methylated cytosine residues, between 1 and 25 methylated cytosine residues, or between 1 and 10 methylated cytosine residues). A determination that the quantity of methylated cytosine residues in the sample isolated from the patient is greater than or less than the amount of methylated cytosine residues in the same DNA sequence within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more (e.g., about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject is likely to respond to treatment with a therapeutic agent, such as BCG, in order to treat the disease. In preferred embodiments, the gene that is analyzed encodes a transcription factor, such as FoxP3, or a cell-surface protein, such as CD45. In these cases, a determination that the quantity of methylated cytosine residues in the sample isolated from the subject is greater than the quantity of methylated cytosine residues in the same DNA sequence within a reference sample (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more (e.g., about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) indicates that the subject is likely to respond to administration of a therapeutic agent, such as BCG, in order to treat the disease.

Example 4

Determining the Likelihood that a Patient Presenting with Elevated Cholesterol Would Benefit from Additional Doses of BCG A subject that is administered BCG or another therapeutic agent in order to reduce serum cholesterol levels may be examined using one or more analytical tests in order to assess the responsiveness of the subject to administration of BCG or another therapeutic agent and to determine if the subject would benefit from additional doses of BCG or another medicament. The subject may be administered BCG or another therapeutic agent and may subsequently have a blood sample withdrawn in order to determine if the methylation state of one or more cytosine residues in the nuclear DNA within a cell of the subject has changed in response to administration of BCG or another therapeutic agent. For instance, a physician of skill in the art can withdraw a blood sample from a subject having previously been administered BCG or another therapeutic agent and may analyze the nuclear DNA within a cell of the sample (e.g., within a T-lymphocyte of the sample, such as a CD4+, CD25+ T-reg cell) to determine if one or more cytosine residues has been methylated or demethylated in response to treatment with BCG or another therapeutic agent. Preferably, the one or more cytosine residues are located within a gene that encodes a transcription factor, such as FoxP3, or within a gene that encodes CD45. A determination that the quantity of methylated cytosine residues in one or more of both of these genetic loci has decreased indicates that the patient is responding to treatment with BCG or another therapeutic agent and may not require subsequently doses. For instance, a determination that one or more particular cytosine residues within the FoxP3 and/or CD45 genes that was previously methylated in the subject prior to treatment with BCG or another therapeutic agent treatment and has since undergone demethylation indicates that the subject is responding to the therapy and may not require subsequent doses of BCG or another medicament.

In contrast, a determination that the quantity of methylated cytosine residues in one or both of these genetic loci has stayed the same or increased indicates that the subject would benefit from one or more additional doses of BCG or another therapeutic agent. For example, a determination that one or more particular cytosine residues within the FoxP3 and/or CD45 genes that was previously methylated in the subject prior to treatment with BCG or another therapeutic agent and remains methylated following administration of BCG or another therapeutic agent indicates that the subject would benefit from one or more subsequent doses of BCG or another therapeutic agent. Alternatively, a determination that that one or more particular cytosine residues within the FoxP3 and/or CD45 genes that was previously demethylated in the subject prior to administration of BCG or another therapeutic agent and has since undergone methylation following administration of BCG or another therapeutic agent indicates that the subject would benefit from one or more subsequent doses of BCG or another therapeutic agent.

Example 5

Administering BCG to a Subject in Order to Treat an Immunological Disorder

A subject presenting with an immunological disorder, such as an allergy, can be treated by administering BCG to the subject in a unit dosage form as described herein. For instance, a subject with an allergy, such as a food allergy, seasonal allergy, chemical allergy, or other allergy described herein can be treated by administering BCG to the subject in a unit dosage form containing, e.g., between about $1.8 \times 10^6$ and about $3.9 \times 10^6$ cfu per 0.1 milligrams of BCG. The subject can subsequently be monitored by a physician of skill in the art in order to assess the efficacy of BCG in treating the allergy and, if necessary, the likelihood that the subject would benefit from one or more additional doses of BCG. For instance, a physician of skill in the art can withdraw a blood sample from the subject after administering the initial dose of BCG (e.g., about 1 week, 1 month, 1 year, 5 years, or 10 years after the initial administration) and can determine the quantity of methylated cytosine residues in a gene of interest within a cell from the blood sample, such as a gene encoding FoxP3 or CD45. This quantity can be compared to the quantity of methylated cytosine residues in the same gene of interest within the same cell type of a blood sample isolated from the subject. The cell from which the gene of interest is analyzed can be, e.g., a T-cell, such as a CD4+, CD25+ T-reg cell. A determination that the quantity of methylated cytosine residues in the FoxP3 or CD45 gene within the sample isolated from the subject after having received BCG treatment has decreased (e.g., by 1, 2, 3, 4, 5, 6, 7, 8, 9, 10, 15, 20, 30, 40, 50, 100, or more residues) relative to the quantity of methylated cytosine residues in a sample isolated from the subject before receiving BCG treatment indicates that the subject is responding well to the BCG therapy and additional doses may not be needed. Alternatively, a determination that the quantity of methylated cytosine residues in the gene of interest has stayed the same or has increased (e.g., e.g., by 1, 2, 3, 4, 5, 6, 7, 8, 9, 10, 15, 20, 30, 40, 50, 100, or more residues) indicates that the subject would likely benefit from one or more additional doses of BCG.

Additionally or alternatively, the efficacy of BCG in treating the allergy can be assessed by analyzing the level of one or more mRNA molecules, proteins, acetylated amino acids, and/or methylated metabolites in the subject before and after being administered BCG. For instance, a physician may withdraw a blood sample from the subject, e.g., about 1 week, 1 month, 1 year, 5 years, or 10 years after the initial administration of BCG and may determine the level of one or more mRNA molecules encoding a cytokine (such as IL-6, TNFα, or IFNγ) or lipolytic protein (such as acyl co-enzyme A oxidase, carnitine palmitoyltransferase, lipase, or uncoupling protein). Alternatively, a physician may directly measure the level of one or more of these proteins. The level(s) of mRNA molecules and/or proteins recorded for the sample isolated from the subject after having received BCG can then be compared to the level of the same mRNA molecule or protein in a sample that was isolated from the subject prior to the subject receiving BCG treatment. The sample that was isolated from the subject prior to receiving BCG may have been previously analyzed (e.g., a physician may have determined the level of the one or more mRNA molecules or proteins of interest immediately after isolating the sample from the subject), or the sample may have been preserved (e.g., cryopreserved) and analyzed at the same time as the sample that was withdrawn following BCG treatment. In either case, a determination that the level(s) of the one or more mRNA molecules and/or proteins has remained the same or has increased (e.g., by about 5%, 6%, 7%, 8%, 9%, 10%, 15%, 20%, 25%, 30%, 35%, 45%, 50%, 55%, 60%, 65%, 70%, 75%, 80%, 85%, 90%, 95%, 100%, or more, or by about 1.1-fold or more (e.g., about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, 1,000-fold, 10,000-fold, or more) following BCG treatment indicates that the patient would likely benefit from one or more additional doses of BCG.

If the determination is made that the patient would benefit from one or more additional dosages of BCG in order to treat the allergy, a physician of skill in the art can administer BCG to the patient, e.g., between 1 and 20 additional times, or more, as needed. The physician may administer BCG to the patient using a route of administration described herein, such as intradermally or intravenously. The physician may administer BCG to the patient, e.g., between about 1 and about 10 years following the initial BCG treatment.

Example 6

Diagnosing a Subject as Having a Disease by Assessing the Level of a Biomarker and Treating the Subject by Administering BCG A subject can be diagnosed with a disease, such as an autoimmune disease or neurological condition, such as type I diabetes, multiple sclerosis, premature ovarian failure, scleroderma, Sjögren's disease, vitiligo, alopecia, polyglandular failure, Grave's disease, hypothyroidism, polymyositis, pemphigus, Crohn's disease, colitis, autoimmune hepatitis, hypopituitarism, myocarditis, Addison's disease, an autoimmune skin disease, uveitis, pernicious anemia, hypoparathyroidism, and rheumatoid arthritis, using methods described herein. For instance, a subject can be assessed for the quantity of methylated cytosine residues in a nuclear gene, such as FoxP3 or CD45, or for the level of one or more mRNA molecules, proteins, acetylated amino acids, or metabolites described herein by a physician of skill in the art. If the physician determines that the subject has a particular disease, such as an autoimmune disease (e.g., type I diabetes), the subject can be treated by administration of BCG. For instance, a physician of skill in the art may diagnose a subject as having type I diabetes. To render the diagnosis, a physician of skill in the art may withdraw a blood sample from the subject and subsequently determine the quantity of methylated cytosine residues in a gene of interest within a cell from the blood sample, such as a gene encoding FoxP3 or CD45. This can be accomplished using methods known in the art, such as bisulfite-mediated DNA sequencing techniques described herein. This quantity may then have been compared to the quantity of methylated cytosine residues in the same gene of interest within the same cell type of a blood sample isolated from a healthy subject that does not have type I diabetes (e.g., a subject of the same age, sex, and/or weight). The cell from which the gene of interest is analyzed may be, e.g., a T-cell, such as a CD4+, CD25+ T-reg cell. A determination that the quantity of methylated cytosine residues in the FoxP3 or CD45 gene within the sample isolated from the subject that has type I diabetes is greater than the quantity of methylated cytosine residues in the sample isolated from the healthy subject (e.g., by 1, 2, 3, 4, 5, 6, 7, 8, 9, 10, 15, 20, 30, 40, 50, 100, or more residues) may indicate that the subject has the disease, such as type I diabetes. Optionally, this assessment can be confirmed through a variety of other procedures known in the art, such as by assessing the blood glucose level of the subject using standard glucose detection assays. The subject can subsequently be treated by a physician that administers BCG to the subject in a unit dosage form containing, e.g., between about $1.8 \times 10^6$ and about $3.9 \times 10^6$ cfu per 0.1 milligrams of BCG. The subject could then be assessed for potential re-dosing regimens, e.g., as described in Example 5.

Example 7

Case Study of the Effect of BCG on Human Serum Lipid Levels

In order to assess the therapeutic effect of BCG in human patients presenting with elevated serum lipid levels, a case study was conducted in which patients were administered BCG and the level of serum cholesterol in each patient was subsequently monitored at specific time intervals.

A first subject (hereinafter "Subject 1") presented with a serum cholesterol level of about 200 mg/dL prior to being administered BCG. The subject was subsequently administered BCG and the subject's level of serum cholesterol was assessed five years following this treatment. At this point, the subject exhibited a serum cholesterol level of about 150 mg/dL. In parallel, a control subject that was not administered BCG was evaluated at the same time points that were used for assessment of Subject 1. The control subject exhibited an initial cholesterol level of about 150 mg/dL. After five years, the control subject exhibited a cholesterol level of about 175 mg/dL.

Similarly, a second subject ("Subject 2") was initially observed as having a serum cholesterol level of about 175 mg/dL. Five years following administration of BCG to the subject, the subject exhibited a cholesterol level of about 150 mg/dL. A control subject assessed in parallel with Subject 2 exhibited an increase of from about 175 mg/dL to about 220 mg/dL over the same time period.

The third subject in this study ("Subject 3") was initially observed as having a serum cholesterol level of about 150 mg/dL. Five years following administration of BCG to the subject, the subject exhibited a cholesterol level of about 125 mg/dL. A control subject assessed in parallel with Subject 3 exhibited an increase of from about 175 mg/dL to about 220 mg/dL over the same time period.

Taken together, these observations demonstrate that BCG effectively lowers the concentration of serum cholesterol in patients presenting with elevated lipid levels, such as patients suffering from type I diabetes. Each of the subjects and controls described in this case study were previously diagnosed as having type I diabetes. However, the effects of BCG on serum lipid levels are not limited to patients with this disease, as BCG can be used to modulate cholesterol, LDL, HDL, and/or triglyceride levels in patients having elevated serum lipids.

Example 8

Administering BCG to a Subject Prone to the Onset of Hypercholesteremia in Order to Prevent the Development of Elevated Serum Cholesterol Levels BCG can be administered to a subject that is prone to develop elevated levels of serum cholesterol even though the patient may not currently exhibit elevated serum concentrations of these lipids. For instance, a subject that currently has a serum cholesterol level that is less than 129 mg/dL (e.g., about 100 mg/dL, 105 mg/dL, 110 mg/dL, 115 mg/dL, 120 mg/dL, or 125 mg/dL, or lower) and that currently has a serum cholesterol level that is within 25% of a previous measurement of the serum cholesterol level of the subject (e.g., a measurement that was recorded within the last 1 day to 20 years, such as a measurement that was recorded within the last 1-5 years) can be administered BCG by a physician of skill in the art in order to prevent the subject from developing an elevated serum cholesterol level in the future. The subject may be one that is prone to develop high cholesterol, e.g., as inferred by a prevalence of cases of elevated cholesterol in the subject's family. The administration of BCG may prevent the subject from developing an elevated serum cholesterol level, such that upon future examination of the subject, e.g., between about 1 day and 20 years, or more, following the administration (such as about 1 day, 1 week, 1 month, 6 months, 1 year, 2 years, 3 years, 4 years, 5 years, 10 years, 15 years, or 20 years, or more, following the administration of BCG), the subject may present serum cholesterol levels that are within 25% (e.g., within 10% or less) of the level of serum cholesterol exhibited by the subject at the time of BCG administration. The subject may additionally be assessed for elevated serum cholesterol or diseases associated therewith, such as hypercholesterolemia, hyperlipidemia, coronary heart disease, peripheral arterial disease (PAD), peripheral vascular disease, hypertension, stroke, diabetes, metabolic syndrome, obesity, and insulin resistance, before and/or after BCG therapy, by assessing the level of one or more biomarkers in a sample isolated from the subject. The biomarkers that are assessed may be one or more methylated cytosine residues in a nuclear gene of interest, such as a gene encoding CD45 or FoxP3. Additionally or alternatively, a physician of skill in the art may assess the subject's level of cholesterol or need for additional doses of BCG by analyzing the level of one or more cytokines (such as IL-6, TNFα, or IFNγ) or lipolytic proteins (such as acyl co-enzyme A oxidase, carnitine palmitoyltransferase, lipase, or uncoupling protein). Alternatively, a physician may directly measure the level of one or more of these proteins. A determination that the levels of these cytokines and/or lipolytic proteins, or the levels of mRNA transcripts encoding these proteins, are within 10% of the levels of these biomarkers previously measured in a sample isolated from the subject (e.g., within 5% or the same as those previously measured in a sample isolated from the subject) indicates that the subject has sustained the level of serum cholesterol exhibited prior to administration of BCG.

Example 9

Administration of BCG Induces a Shift from Oxidative Phosphorylation to Aerobic Glycolysis In order to assess the molecular effects of BCG in human patients and in cultured human blood cells, a series of experiments were conducted aimed at understanding how BCG modulates the metabolism of glucose and cholesterol. As shown in FIG. 7, human type-1 diabetes patients treated with BCG exhibited a sustained decrease in total cholesterol level over the course of an 8-year investigation. BCG administration was further shown to enhance NR1H3 expression at the mRNA level in vitro in cultured peripheral blood lymphocytes and in vivo in human type-1 diabetes patients (FIG. 7). Dissecting the effects of BCG administration further revealed that BCG promotes the expression of cholesterol-suppressing genes and attenuates the expression of glucose-elevating genes, providing a two-fold therapeutic effect of reducing total cholesterol and blood sugar level. The ability of BCG to modulate blood sugar is also manifest in the stabilizing effect on glycated hemoglobin levels observed upon administration of BCG to human type-1 diabetes patients (FIG. 8).

Surprisingly, I have discovered that BCG is capable of inducing a metabolic conversion from a state of oxidative phosphorylation to a state of aerobic glycolysis (FIG. 9). This conversion results in the rapid consumption of glucose. As shown in FIG. 9, the effect of BCG administration to type-1 diabetic patients on blood glucose is due to an increased flux through glycolysis and is independent of pancreas regeneration. The ability of BCG to induce a conversion from a state of oxidative phosphorylation to one of aerobic glycolysis is due to BCG's capacity to promote HIF1-α expression (FIG. 9).

In further evidence of the ability of BCG to induce a shift towards glycolysis, I have observed that BCG is capable of κp-regulating glucose transporters and early glycolytic enzymes while suppressing the expression of proteins involved in the Krebs cycle (FIG. 10).

Example 10

BCG Therapy can Treat Hyperglycemia in any Disease State, Regardless of the Underlying Etiology The physiological manifestations of the biochemical phenomena described in Example 9 were further investigated in hyperglycemic BALB/c mice. A state of hyperglycemia was induced in BALB/c mice by administration of streptozotocin, an agent that non-specifically elevates blood glucose. Hyperglycemic mice treated with BCG not only exhibited an improved ability to maintain weight, but also markedly reduced and stabilized blood sugar levels (FIG. 11). These effects are significant, as streptozotocin induces an increase in blood glucose in a disease-independent fashion. That BCG therapy was capable of promoting maintenance of weight and reduction in blood sugar levels in streptozotocin-treated mice indicates that BCG can reduce blood sugar in any disease state, regardless of the underlying etiology.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of reducing the level of cholesterol, low-density lipoprotein (LDL), or triglycerides in a subject in need thereof comprising:
   (i) intradermally or subcutaneously administering an initial dose of Bacillus Calmette-Guerin (BCG) to said subject; and
   (ii) intradermally or subcutaneously administering a subsequent dose of BCG to said subject,
   wherein the subsequent dose is administered at least one year after administration of the initial dose, and wherein the subject is not administered BCG during the time elapsed between administration of the initial dose and administration of the subsequent dose,
   wherein prior to administration of the initial dose of BCG, the subject has been identified as having, as a reference level, a total cholesterol level of about 100 mg/dL or greater, an LDL level of about 80 mg/dL or greater, and/or a triglyceride level of about 100 mg/dL or greater; and
   wherein administration of BCG in step (i) or (ii) reduces the level of cholesterol, LDL, or triglycerides in the subject to below the reference level.

2. The method of claim 1, wherein, prior to administration of the initial dose of BCG, said subject:
   a) has been identified as having, as a reference level, a high-density lipoprotein (HDL) level of about 40 mg/dL or below;
   b) has been identified as having, as a reference level, a ratio of total cholesterol level to HDL level of about 5 or greater;
   c) been identified as suffering from a disease associated with an elevated level of cholesterol;
   d) has been identified as having, as a reference level, a blood glucose level of about 100 mg/dL or greater; and/or
   e) been identified as suffering from a disease associated with an elevated blood glucose level.

3. The method of claim 2, wherein:
   a) said disease associated with an elevated level of cholesterol is selected from the group consisting of hypercholesterolemia, hyperlipidemia, coronary heart disease, peripheral arterial disease (PAD), peripheral vascular disease, hypertension, stroke, diabetes, metabolic syndrome, obesity, and insulin resistance; and/or
   b) said disease associated with an elevated blood glucose level is selected from the group consisting of type 2 diabetes, noninsulin-dependent diabetes mellitus (NIDDM), nonalcoholic steatohepatitis (NASH), metabolic syndrome, cystic fibrosis, drug induced hyperglycemia, insulin resistance syndromes, diseases caused by genetic mutations in the pancreas, cancer, infection, Leprechaunism, Rabson Mandenhall syndrome, lipoatrophic diabetes, pancreatitis, trauma, hemochromatoisis, fibrocalculous pancreatopathy, acromegaly, Cushings syndrome, glucagonoma, pheochromocytoma, hyperthyroism, somatostatinoma, aldosteroma, infections associated with beta cell destruction, Rubella, coxsachie virus B, mumps, cytomegatolovirus infection, adenovirus infection, a genetic syndrome, stiff person syndrome, anti-insulin receptor abnormalities, liver disease, and renal failure.

4. The method of claim 1, wherein said method further comprises administering to said subject a hypolipidemic agent.

5. The method of claim 4, wherein said hypolipidemic agent is selected from the group consisting of a HMG-CoA reductase inhibitor, niacin, a fibric acid derivative, a cholesterol absorption inhibitor, and a lipolytic agent.

6. The method of claim 1, wherein said method further comprises administering to said subject an additional therapeutic agent selected from the group consisting of tumor necrosis factor-alpha (TNFα), a tumor necrosis factor receptor 2 (TNFR2) agonist, an immunotherapy agent, and combinations thereof.

7. The method of claim 1, whereby said initial and subsequent doses of BCG promote:
a) demethylation of one or more cytosine deoxyribonucleotides in said subject, wherein said one or more deoxyribonucleotides are located within a gene that encodes FoxP3 or CD45;
b) an increase in the level of a cytokine or a lipolytic protein and/or an mRNA molecule encoding said cytokine or lipolytic protein, optionally wherein said cytokine is selected from the group consisting of interleukin-6 (IL-6), TNFα, and interferon-gamma (IFNγ) and/or said lipolytic protein is selected from the group consisting of acyl co-enzyme A oxidase, carnitine palmitoyltransferase, lipase, and uncoupling protein;
c) a decrease in the level of a lipogenic protein or an adiponectin receptor and/or an mRNA molecule encoding said lipogenic protein or adiponectin receptor, optionally wherein said lipogenic protein is selected from the group consisting of acetyl co-enzyme A carboxylase α, acetyl co-enzyme A carboxylase β, fatty acid synthase, glyceraldehydes-6-phosphate dehydrogenase, stearoyl-CoA saturase, malic enzyme, and glucose-6-phosphate dehydrogenase and/or said adiponectin receptor is selected from the group consisting of adiponectin receptor 1 and adiponectin receptor 2;
d) acetylation of one or more amino acids in said subject selected from the group consisting of alanine, aspartic acid, serine, threonine, histidine, 3-methylhistidine, valine, lysine, and methionine;
e) methylation of one or more metabolites in said subject selected from the group consisting of N-α-acetylhistidine, glutaconic acid, glutarylcarnitine, lysine, and cysteine;
f) demethylation of one or more metabolites in said subject selected from the group consisting of 4-methyl-2-oxopentanoic acid and 3-methyl-2-oxobutyric acid;
g) a decrease in the level of one or more lysine acetyltransferases (KATs) in said subject selected from the group consisting of KAT2A, KAT2B, KAT5, KAT6A, KAT6B, KAT7, and KAT8;
h) a decrease in the level of one or more histone acetyltransferases and/or one or more histone deacetylases (HDACs) in said subject selected from the group consisting of HDAC1, HDAC2, HDAC3, HDAC4, HDAC5, HDAC6, HDAC7, HDAC8, HDAC9, HDAC10, HDAC11, HDAC1P1, HDAC1P2, SIRT1, SIRT2, SIRT3, SIRT4, SIRT5, SIRT6, and SIRT7; and/or
i) a decrease in the level of one or more histones in said subject belonging to a family selected from the group consisting of H2A, H2B, H3, and H4.

8. The method of claim 1, wherein said subject is a mammal.

9. The method of claim 8, wherein said mammal is a human.

10. The method of claim 5, wherein:
a) said HMG-CoA reductase inhibitor is selected from the group consisting of atorvastatin, cerivastatin, fluvastatin, lovastatin, mevastatin, pitavastatin, pravastatin, rosuvastatin, simvastatin, and combinations thereof;
b) said fibric acid derivative is selected from the group consisting of fenofibrate and gemfibrozil;
c) said cholesterol absorption inhibitor is ezetimibe;
d) said lipolytic agent is selected from the group consisting of norepinephrine, isoproterenol, forskolin, bucladesine, and theophylline; and/or
e) said lipolytic agent is selected from the group consisting of norepinephrine, isoproterenol, forskolin, bucladesine, and theophylline.

11. The method of claim 1, wherein the initial dose of BCG comprises from about $1\times10^6$ colony-forming units (cfu) to about $6\times10^6$ cfu per 0.1 mg of BCG.

12. The method of claim 11, wherein the initial dose of BCG comprises from about $1.8\times10^6$ cfu to about $3.9\times10^6$ cfu per 0.1 mg of BCG.

13. The method of claim 1, wherein the subsequent dose of BCG comprises from about $1\times10^6$ cfu to about $6\times10^6$ cfu per 0.1 mg of BCG.

14. The method of claim 13, wherein the subsequent dose of BCG comprises from about $1.8\times10^6$ cfu to about $3.9\times10^6$ cfu per 0.1 mg of BCG.

15. The method of claim 1, wherein the subject's level of cholesterol, LDL, or triglycerides one year after administration of the initial dose of BCG is determined to be within 10% of the reference level of cholesterol, LDL, or triglycerides prior to administration of the initial dose of BCG.

16. The method of claim 1, wherein the subject's level of cholesterol, LDL, or triglycerides one year after administration of the initial dose of BCG is determined to be within 5% of the reference level of cholesterol, LDL, or triglycerides prior to administration of the initial dose of BCG.

17. The method of claim 1, wherein, following administration of the subsequent dose of BCG to the subject, the subject is administered one or more additional doses of BCG.

18. The method of claim 17, wherein the one or more additional doses of BCG are administered to the subject at a frequency of no greater than once per year.

19. The method of claim 1, wherein prior to administration of the initial dose of BCG, the subject has been identified as having a total cholesterol level of about 129 mg/dL or greater.

20. The method of claim 1, wherein, prior to administration of the initial dose of BCG, said subject has been identified as having a ratio of total cholesterol level to HDL level of between about 3 and about 10.

* * * * *

UNITED STATES PATENT AND TRADEMARK OFFICE
CERTIFICATE OF CORRECTION

PATENT NO.         : 11,266,730 B2
APPLICATION NO.    : 15/763967
DATED              : March 8, 2022
INVENTOR(S)        : Denise L. Faustman It is certified that error appears in the above-identified patent and that said Letters Patent is hereby corrected as shown below:

In the Claims

Column 64, Line 28, replace "c) been" with --c) has been--;
       Line 33, replace "e) been" with --e) has been--.

Column 64, Line 49, replace "Rabson Mandenhall" with --Rabson-Mendenhall--;
       Lines 50-51, replace "hemochromatoisis" with --hemochromatosis--;
       Line 53, replace "hyperthyroisim" with --hyperthyroidism--;
       Line 55, replace "cytomegatolovirus" with --cytomegalovirus--.

Signed and Sealed this
Fifth Day of July, 2022

Katherine Kelly Vidal
*Director of the United States Patent and Trademark Office*